US011180551B2

(12) United States Patent
Peters et al.

(10) Patent No.: US 11,180,551 B2
(45) Date of Patent: *Nov. 23, 2021

(54) HUMANIZED MONOCLONAL ANTIBODIES THAT TARGET VE-PTP (HPTP-BETA)

(71) Applicant: EyePoint Pharmaceuticals, Inc., Cincinnati, OH (US)

(72) Inventors: Kevin Peters, Cincinnati, OH (US); Michael Allen Flynn, Ann Arbor, MI (US)

(73) Assignee: EyePoint Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/851,420

(22) Filed: Apr. 17, 2020

(65) Prior Publication Data

US 2020/0270342 A1    Aug. 27, 2020

Related U.S. Application Data

(63) Continuation of application No. 16/775,860, filed on Jan. 29, 2020, which is a continuation of application No. 16/180,850, filed on Nov. 5, 2018, now Pat. No. 10,604,569, which is a continuation of application No. 15/654,289, filed on Jul. 19, 2017, now Pat. No. 10,253,094.

(60) Provisional application No. 62/377,072, filed on Aug. 19, 2016, provisional application No. 62/364,381, filed on Jul. 20, 2016.

(51) Int. Cl.
| | |
|---|---|
| *C07K 16/28* | (2006.01) |
| *A61K 39/395* | (2006.01) |
| *C07K 16/22* | (2006.01) |
| *A61K 39/00* | (2006.01) |

(52) U.S. Cl.
CPC .......... *C07K 16/28* (2013.01); *A61K 39/3955* (2013.01); *C07K 16/22* (2013.01); *C07K 16/2896* (2013.01); *A61K 2039/505* (2013.01); *A61K 2039/507* (2013.01); *A61K 2039/54* (2013.01); *A61K 2039/545* (2013.01); *C07K 2317/24* (2013.01); *C07K 2317/33* (2013.01); *C07K 2317/51* (2013.01); *C07K 2317/515* (2013.01); *C07K 2317/75* (2013.01); *C07K 2317/76* (2013.01); *C07K 2317/92* (2013.01)

(58) Field of Classification Search
CPC .... C07K 16/22; C07K 16/28; C07K 16/2896; C07K 2317/24; C07K 2317/33; C07K 2317/51; C07K 2317/515; C07K 2317/75; C07K 2317/76; C07K 2317/92; A61K 39/3955; A61K 2039/505; A61K 2039/507; A61K 2039/54; A61K 2039/545; A61K 2300/00; A61P 35/00

See application file for complete search history.

(56) References Cited

U.S. PATENT DOCUMENTS

| | | | |
|---|---|---|---|
| 6,455,035 B1 | 9/2002 | Suri et al. | |
| 7,226,755 B1 | 6/2007 | Peters et al. | |
| 7,507,568 B2 | 3/2009 | Evdokimov et al. | |
| 7,589,212 B2 | 9/2009 | Gray et al. | |
| 7,622,593 B2 | 11/2009 | Gray et al. | |
| 7,632,862 B2 | 12/2009 | Peters et al. | |
| 7,769,575 B2 | 8/2010 | Evdokimov et al. | |
| 7,795,444 B2 | 9/2010 | Gray et al. | |
| 7,973,142 B2 | 7/2011 | Rotello et al. | |
| 8,106,078 B2 | 1/2012 | Gray et al. | |
| 8,188,125 B2 | 5/2012 | Gray et al. | |
| 8,258,311 B2 | 9/2012 | Gray et al. | |
| 8,329,916 B2 | 12/2012 | Amarasinghe et al. | |
| 8,338,615 B2 | 12/2012 | Gray et al. | |
| 8,524,235 B2 | 9/2013 | Rotello et al. | |
| 8,569,348 B2 | 10/2013 | Shalwitz et al. | |
| 8,846,685 B2 | 9/2014 | Gray et al. | |
| 8,883,832 B2 | 11/2014 | Shalwitz et al. | |
| 8,895,563 B2 | 11/2014 | Gray et al. | |
| 8,946,232 B2 | 2/2015 | Gray et al. | |
| 8,999,325 B2 | 4/2015 | Peters et al. | |
| 9,096,555 B2 | 8/2015 | Shalwitz et al. | |
| 9,126,958 B2 | 9/2015 | Gray et al. | |
| 9,174,950 B2 | 11/2015 | Shalwitz et al. | |
| 9,284,285 B2 | 3/2016 | Gray et al. | |
| 9,440,963 B2 | 9/2016 | Peters et al. | |
| 9,458,211 B1 | 10/2016 | Bakker et al. | |
| 9,539,245 B2 | 1/2017 | Peters | |
| RE46,592 E | 10/2017 | Gray et al. | |
| 9,795,594 B2 | 10/2017 | Gray et al. | |
| 9,926,367 B2 | 3/2018 | Rotello et al. | |
| 9,949,956 B2 | 4/2018 | Shalwitz et al. | |

(Continued)

FOREIGN PATENT DOCUMENTS

| | | |
|---|---|---|
| EP | 1165115 B1 | 5/2003 |
| EP | 2004697 A2 | 12/2008 |

(Continued)

OTHER PUBLICATIONS

Amarasinghe, et al., Design and synthesis of potent, non-peptidic inhibitors of HPTPP, Bioorganic & Medicinal Chemistry Letters, 16 (2006) 4252-56.

(Continued)

*Primary Examiner* — Robert S Landsman

(74) *Attorney, Agent, or Firm* — Wilson Sonsini Goodrich & Rosati

(57) ABSTRACT

The disclosure provides compositions and methods for the treatment of ocular conditions associated with angiogenesis comprising administering an antibody that targets a tyrosine phosphatase inhibitor in a subject.

34 Claims, 25 Drawing Sheets

Specification includes a Sequence Listing.

(56) References Cited

U.S. PATENT DOCUMENTS

| | | |
|---|---|---|
| 9,968,674 B2 | 5/2018 | Ioffe et al. |
| 10,150,811 B2 | 12/2018 | Peters et al. |
| 10,220,048 B2 | 3/2019 | Peters et al. |
| 10,253,094 B2 | 4/2019 | Peters et al. |
| 10,329,357 B2 | 6/2019 | Peters et al. |
| 10,463,650 B2 | 11/2019 | Gray et al. |
| 10,597,452 B2 | 3/2020 | Peters et al. |
| 10,604,569 B2 | 3/2020 | Peters et al. |
| 2003/0055006 A1 | 3/2003 | Siemeister et al. |
| 2003/0215899 A1 | 11/2003 | Meng et al. |
| 2004/0077065 A1 | 4/2004 | Evdokimov et al. |
| 2004/0254197 A1 | 12/2004 | Tasaka et al. |
| 2005/0004056 A1 | 1/2005 | Meise et al. |
| 2005/0260132 A1 | 11/2005 | Chin et al. |
| 2006/0014204 A1 | 1/2006 | Gale et al. |
| 2007/0134234 A1 | 6/2007 | Smith et al. |
| 2007/0154482 A1 | 7/2007 | Sukhatme et al. |
| 2009/0246206 A1 | 10/2009 | Nielsen et al. |
| 2010/0016336 A1 | 1/2010 | Gray et al. |
| 2010/0056610 A1 | 3/2010 | Peters et al. |
| 2010/0111894 A1 | 5/2010 | Benny-Ratsaby et al. |
| 2011/0268656 A1 | 11/2011 | Ho et al. |
| 2011/0268694 A1 | 11/2011 | Shalwitz et al. |
| 2012/0129847 A1 | 5/2012 | Peters et al. |
| 2012/0207682 A1 | 8/2012 | Ashton |
| 2013/0023542 A1 | 1/2013 | Gray et al. |
| 2013/0095065 A1 | 4/2013 | Peters et al. |
| 2013/0331386 A1 | 12/2013 | Shalwitz et al. |
| 2014/0044707 A1 | 2/2014 | Rotello et al. |
| 2014/0066458 A1 | 3/2014 | Shalwitz et al. |
| 2014/0288134 A1 | 9/2014 | Peters et al. |
| 2015/0050277 A1 | 2/2015 | Peters et al. |
| 2015/0232575 A1 | 8/2015 | Peters et al. |
| 2015/0258120 A1 | 9/2015 | Zarnitsyn et al. |
| 2016/0000871 A1 | 1/2016 | Quaggin |
| 2016/0008327 A1 | 1/2016 | Shalwitz et al. |
| 2016/0038467 A1 | 2/2016 | Peters |
| 2016/0082129 A1 | 3/2016 | Peters |
| 2016/0130321 A1 | 5/2016 | Burian |
| 2016/0130337 A1 | 5/2016 | Gekkieva et al. |
| 2016/0137717 A1 | 5/2016 | Burian |
| 2016/0144025 A1 | 5/2016 | Vitti et al. |
| 2016/0159893 A1 | 6/2016 | Burian et al. |
| 2016/0168240 A1 | 6/2016 | Burian et al. |
| 2016/0220540 A1 | 8/2016 | Peters et al. |
| 2016/0220541 A1 | 8/2016 | Kevin et al. |
| 2016/0251421 A1 | 9/2016 | Brown et al. |
| 2016/0333090 A1 | 11/2016 | Horlick et al. |
| 2016/0374996 A1 | 12/2016 | Gray et al. |
| 2017/0079959 A1 | 3/2017 | Peters |
| 2017/0260265 A1 | 9/2017 | Duerr et al. |
| 2017/0275353 A1 | 9/2017 | Sheng et al. |
| 2017/0349649 A1 | 12/2017 | Rotello et al. |
| 2018/0016245 A1 | 1/2018 | Shalwitz et al. |
| 2018/0022741 A1 | 1/2018 | Peters et al. |
| 2018/0037579 A1 | 2/2018 | Peters et al. |
| 2018/0092883 A1 | 4/2018 | Peters et al. |
| 2018/0237430 A1 | 4/2018 | Peters et al. |
| 2018/0237429 A1 | 8/2018 | Peters et al. |
| 2018/0237431 A1 | 8/2018 | Peters et al. |
| 2018/0251457 A1 | 9/2018 | Peters et al. |
| 2018/0353614 A1 | 12/2018 | Peters |

FOREIGN PATENT DOCUMENTS

| | | |
|---|---|---|
| EP | 2142189 A1 | 1/2010 |
| EP | 2385763 A1 | 11/2011 |
| EP | 2451279 A1 | 5/2012 |
| EP | 2592072 A2 | 5/2013 |
| EP | 2592073 A2 | 5/2013 |
| EP | 2624916 A2 | 8/2013 |
| EP | 2766043 A1 | 8/2014 |
| EP | 2766044 A1 | 8/2014 |
| EP | 2041129 B1 | 9/2014 |
| EP | 2041102 B1 | 11/2014 |
| EP | 2803663 A1 | 11/2014 |
| EP | 2038265 B1 | 3/2015 |
| EP | 2967066 A1 | 1/2016 |
| EP | 3168234 A1 | 5/2017 |
| EP | 2371865 B1 | 7/2017 |
| WO | WO-9845331 A2 | 10/1998 |
| WO | WO-0057901 A1 | 10/2000 |
| WO | WO-0065085 A1 | 11/2000 |
| WO | WO-2007087457 A2 | 8/2007 |
| WO | WO-2007113648 A2 | 10/2007 |
| WO | WO-2007116360 A2 | 10/2007 |
| WO | WO-2008002569 A2 | 1/2008 |
| WO | WO-2008002570 B1 | 4/2008 |
| WO | WO-2008002571 B1 | 4/2008 |
| WO | WO-2010060748 A1 | 6/2010 |
| WO | WO-2010081172 A1 | 7/2010 |
| WO | WO-2010097800 A1 | 9/2010 |
| WO | WO-2011005330 A1 | 1/2011 |
| WO | WO-2011135067 A1 | 11/2011 |
| WO | WO-2012047966 A2 | 4/2012 |
| WO | WO-2013056233 A1 | 4/2013 |
| WO | WO-2013056240 A1 | 4/2013 |
| WO | WO-2014145068 A1 | 9/2014 |
| WO | WO-2015138882 A1 | 9/2015 |
| WO | WO-2016022813 A1 | 2/2016 |
| WO | WO-2016049183 A1 | 3/2016 |
| WO | WO-2017053566 A1 | 3/2017 |
| WO | WO-2018017714 A1 | 1/2018 |

OTHER PUBLICATIONS

Attwood. Genomics. The Babel of bioinformatics. Science. Oct. 20, 2000;290(5491):471-3.

Campbell Monoclonal Antibody Technology, 1984, Chapter 1, pp. 1-32.

Campochiaro, et al. Enhanced Benefit in Diabetic Macular Edema from AKB-9778 Tie2 Activation Combined with Vascular Endothelial Growth Factor Suppression. Ophthalmology. Aug. 2016;123(8):1722-30.

Colman et al., Effects of amino acid sequence changes on antibody-antigen interactions, Research in Immunology, 1994; 145(1):33-36.

Frye, et al. Interfering with VE-PTP stabilizes endothelial junctions in vivo via Tie-2 in the absence of VE-cadherin. Dec. 14, 2015;212(13):2267-87.

Golay, et al. Mechanism of action of therapeutic monoclonal antibodies: promises and pitfalls of in vitro and in vivo assays. Arch Biochem Biophys. Oct. 15, 2012;526(2):146-53. doi: 10.1016/j.abb.2012.02.011. Epub Feb. 25, 2012.

Gurnik S, et al. Angiopoietin-2-induced blood-brain barrier compromise and increased stroke size are rescued by VE-PTP-dependent restoration of Tie2 signaling. Acta Neuropathol. May 2016;131(5):753-73.

Houghten, et al. New Approaches to Immunization, Vaccines 86, Cold Spring Harbor Laboratory, p. 21-25, 1986.

International search report with written opinion dated Dec. 26, 2017 for PCT Application No. PCT/US2017/042855.

Jeansson, et al., Angiopoietin-1 is essential in mouse vasculature during development and in response to injury, The Journal of Clinical Investigation, Jun. 2011, 121(6):2278-89.

Jubala, et al. CD20 expression in normal canine B cells and in canine non-Hodgkin lymphoma. Vet Pathol. Jul. 2005;42(4):468-76.

Lederman et al. A single amino acid substitution in a common African allele of the CD4 molecule ablates binding of the monoclonal antibody, OKT4. Mol Immunol 28(11):1171-1181 (1991).

Li, et al. beta-Endorphin omission analogs: dissociation of immunoreactivity from other biological activities. Proc Natl Acad Sci U S A. Jun. 1980;77(6):3211-4.

Lip, et al. Plasma vascular endothelial growth factor, angiopoietin-2, and soluble angiopoietin receptor tie-2 in diabetic retinopathy: effects of laser photocoagulation and angiotensin receptor blockade. Br J Ophthalmol. Dec. 2004;88(12):1543-6.

Nawroth, et al. VE-PTP and VE-cadherin ectodomains interact to facilitate regulation of phosphorylation and cell contacts. EMBO J. Sep. 16, 2002;21(18):4885-95.

(56) References Cited

OTHER PUBLICATIONS

Nguyen, et al. Vascular endothelial growth factor is a critical stimulus for diabetic macular edema. Am J Ophthalmol. Dec. 2006;142(6):961-9. Epub Aug. 2, 2006.

Owens, et al. The genetic engineering of monoclonal antibodies. J Immunol Methods. Feb. 10, 1994;168(2):149-65.

Paul. Fundamental Immunology, 3rd Edition, Chapter 9, pp. 292-295 (1993).

Paul. Fundamental Immunology. Chapter 8 Immunogenicty and antigen structure., 3d ed., p. 242, 1993.

Riemer, et al. Matching of trastuzumab (Herceptin) epitope mimics onto the surface of Her-2/neu—a new method of epitope definition. Mol Immunol. May 2005;42(9):1121-4. Epub Jan. 8, 2005.

Rudikoff, et al. Single amino acid substitution altering antigen-binding specificity. Proc Natl Acad Sci U S A. Mar. 1982;79(6):1979-83.

Schindelholz, et al. Regulation of CNS and motor axon guidance in *Drosophila* by the receptor tyrosine phosphatase DPTP52F. Development. Nov. 2001;128(21):4371-82.

Shen, et al. Targeting VE-PTP activates TIE2 and stabilizes the ocular vasculature. J Clin Invest. Oct. 2014;124(10):4564-76.

Stancovski, et al. Mechanistic aspects of the opposing effects of monoclonal antibodies to the ERBB2 receptor on tumor growth. Proc Natl Acad Sci U S A. Oct. 1, 1991;88(19):8691-5.

Thomson, et al., A lymphatic defect causes ocular hypertension and glaucoma in mice, The Journal of Clinical Investigation, Oct. 2014, 124(10):4320-4.

U.S. Appl. No. 15/654,289 Notice of Allowance dated Nov. 30, 2018.

U.S. Appl. No. 15/654,289 Office Action dated Jul. 6, 2018.

U.S. Appl. No. 16/180,850 Office Action dated Aug. 30, 2019.

Van Der Flier, et al. Antibody neutralization of vascular endothelial growth factor (VEGF) fails to attenuate vascular permeability and brain edema in experimental pneumococcal meningitis. J Neuroimmunol. Mar. 2005;160(1-2):170-7.

Vestweber, et al., Molecular Mechanisms That Control Endothelial Cell Contacts, J. Pathol 2000, 190:281-91.

Winderlich, et al. VE-PTP controls blood vessel development by balancing Tie-2 activity. J Cell Biol. May 18, 2009;185(4):657-71. doi: 10.1083/jcb.200811159.

Witte, et al. Monoclonal antibodies targeting the VEGF receptor-2 (Flk1/KDR) as an anti-angiogenic therapeutic strategy. Cancer Metastasis Rev. Jun. 1998;17(2):155-61.

Yacyshyn, et al. Tyrosine phosphatase beta regulates angiopoietin-Tie2 signaling in human endothelial cells. Angiogenesis. 2009;12(1):25-33. doi: 10.1007/s10456-008-9126-0. Epub Jan. 1, 2009.

Yu, et al. Interaction between bevacizumab and murine VEGF-A: a reassessment. Invest Ophthalmol Vis Sci. Feb. 2008;49(2):522-7. doi: 10.1167/iovs.07-1175.

Non-Final Office Action dated Aug. 30, 2019 for U.S. Appl. No. 16/180,854.

U.S. Appl. No. 16/180,854 Office Action dated Aug. 30, 2019.

Notice of Allowance dated Jan. 15, 2020 for U.S. Appl. No. 16/180,850.

```
                        1                                                50
(SEQ ID NO: 50)  VH0  EVQLVETGGGLVQPKGSMKLSCAASGFTFNANAMNWIRQAPGKGLEWVAR
(SEQ ID NO:  9)  VH1  EVQLVESGGGLVQPGGSLKLSCAASGFTFNANAMNWVRQASGKGLEWVGR
(SEQ ID NO: 10)  VH2  EVQLVESGGGLVQPGGSLRLSCAASGFTFNANAMNWVRQAPGKGLEWVGR
(SEQ ID NO: 11)  VH3  EVQLVESGGGLVQPGRSLRLSCTASGFTFNANAMNWVRQAPGKGLEWVGR
(SEQ ID NO: 12)  VH4  LVQLVESGGGLVKPGGSLRLSCAASGFTFNANAMNWIRQAPGKGLEWVSR 51                                               100
(SEQ ID NO: 50)  VH0  IRTKSNNYATYYAGSVKDRFTISRDDAQNMLYLQMNDLKTEDTAMYYCVR
(SEQ ID NO:  9)  VH1  IRTKSNNYATYYAGSVKDRFTISRDDSKNTAYLQMNSLKTEDTAAYYCVR
(SEQ ID NO: 10)  VH2  IRTKSNNYATYYAGSVKDRFTISRDDSKNSLYLQMNSLKTEDTAVYYCVR
(SEQ ID NO: 11)  VH3  IRTKSNNYATYYAGSVKDRFTISRDDSKNIAYLQMNSLKTEDTAVYYCVR
(SEQ ID NO: 12)  VH4  IRTKSNNYATYYAGSVKDRFTISRDNAKNSLYLQMNSLRAEDTAVHYCVR 101            122
(SEQ ID NO: 50)  VH0  DYYGSSAWITYWGQGTLVTVSA
(SEQ ID NO:  9)  VH1  DYYGSSAWITYWGQGTLVTVSS
(SEQ ID NO: 10)  VH2  DYYGSSAWITYWGQGTLVTVSS
(SEQ ID NO: 11)  VH3  DYYGSSAWITYWGQGTLVTVSS
(SEQ ID NO: 12)  VH4  DYYGSSAWITYWGQGTLVTVSS
```

FIGURE 1

```
                      1                                                50
(SEQ ID NO: 51) VL0  DIVMTQSHKFMSTSVGDRVSITCKASQHVGTAVAWYQQKPDQSPKQLIYW
(SEQ ID NO: 20) VL1  DVVMTQSPSFLSASVGDRVTITCKASQHVGTAVAWYQQRPGKAPKLLIYW
(SEQ ID NO: 21) VL2  DIVMTQSPDSLAVSLGERATINCKASQHVGTAVAWYQQKPGQPPKLLIYW
(SEQ ID NO: 22) VL3  DIQMTQSPFSLSASVGDRVTITCKASQHVGTAVAWYQQKPGKAPKLLIYW
(SEQ ID NO: 23) VL4  DIVMTQSPDSLAVSLGERATINCKASQHVGTAVAWYQQKPEQPPKLLIYW 51                                               100
(SEQ ID NO: 51) VL0  ASTRHTGVPDRFTGSGSGTDFTLTISNVQSEDLADYFCQQYSSYPFTFGS
(SEQ ID NO: 20) VL1  ASTRHTGVPSRFSGSGSGTEFTLTISSLQPEDFATYFCQQYSSYPFTFGG
(SEQ ID NO: 21) VL2  ASTRHTGVPDRFSGSGSGTDFTLTISSLQAEDVAVYYCQQYSSYPFTFGQ
(SEQ ID NO: 22) VL3  ASTRHTGVPSRFSGSGSGTDFTLTISSLQPEDFATYFCQQYSSYPFTFGG
(SEQ ID NO: 23) VL4  ASTRHTGVPDRFSGSGSGTDFTLTISSLQAEDVAVYYCQQYSSYPFTFGG 101
(SEQ ID NO: 51) VL0  GTKLEIK
(SEQ ID NO: 20) VL1  GTKLEIK
(SEQ ID NO: 21) VL2  GTKLEIK
(SEQ ID NO: 22) VL3  GTKLEIK
(SEQ ID NO: 23) VL4  GTKVEIK
```

FIGURE 2

A Reducing SDS-PAGE
B Non-Reducing SDS-PAGE
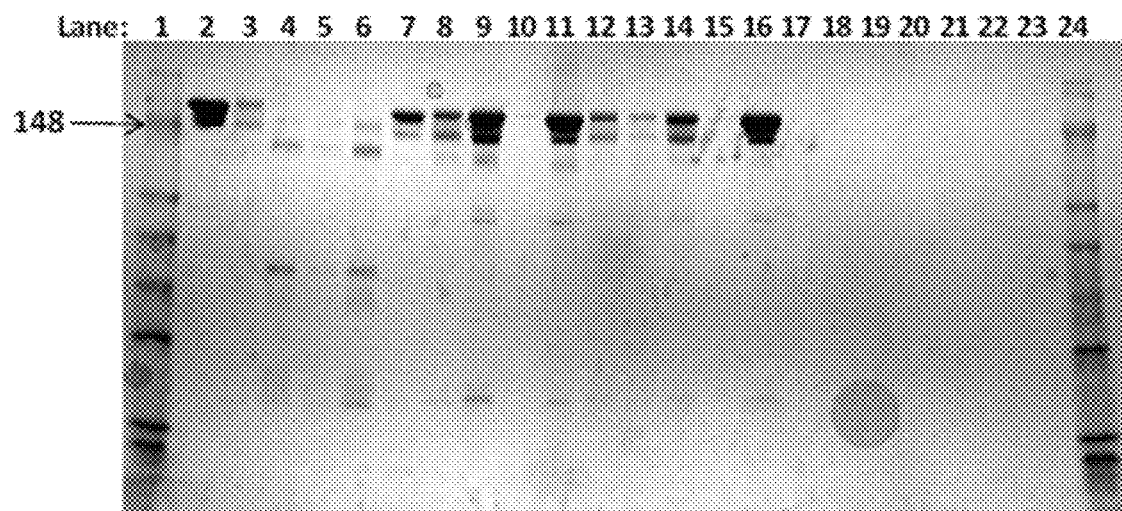
FIGURE 13

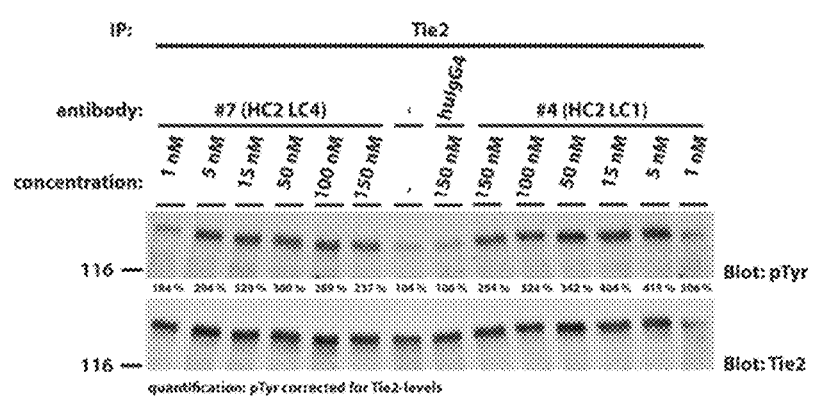
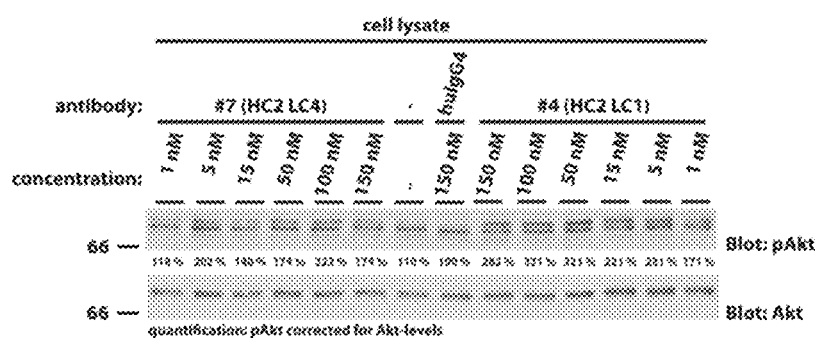
FIGURE 19

SEQUENCE LISTING

<160> NUMBER OF SEQ ID NOS: 59

<210> SEQ ID NO 1
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Phe Gly Leu Ser Trp Val Phe Phe Val Val Phe Tyr Gln Gly
1               5                   10                  15

Val His Cys Glu Val Gln Leu Val Glu Thr Gly Gly Gly Leu Val Gln
                20                  25                  30

Pro Lys Gly Ser Met Lys Leu Ser Cys Ala Ala Ser Gly Phe Thr Phe
            35                  40                  45

Asn Ala Asn Ala Met Asn Trp Ile Arg Gln Ala Pro Gly Lys Gly Leu
        50                  55                  60

Glu Trp Val Ala Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asp Ala
                85                  90                  95

Gln Asn Met Leu Tyr Leu Gln Met Asn Asp Leu Lys Thr Glu Asp Thr
            100                 105                 110

Ala Met Tyr Tyr Cys Val Arg Asp Tyr Tyr Gly Ser Ser Ala Trp Ile
        115                 120                 125

Thr Tyr Trp Gly Gln Gly Thr Leu Val Thr Val Ser Ala
    130                 135                 140

<210> SEQ ID NO 2
<211> LENGTH: 100
<212> TYPE: PRT
<213> ORGANISM: Homo sapiens

<400> SEQUENCE: 2

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
                20                  25                  30

Ala Met His Trp Val Arg Gln Ala Ser Gly Lys Gly Leu Glu Trp Val
            35                  40                  45

Gly Arg Ile Arg Ser Lys Ala Asn Ser Tyr Ala Thr Ala Tyr Ala Ala
        50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 3
<211> LENGTH: 100
<212> TYPE: PRT
<213> ORGANISM: Homo sapiens

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg
            100

<210> SEQ ID NO 4
<211> LENGTH: 98
<212> TYPE: PRT
<213> ORGANISM: Homo sapiens

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 5
<211> LENGTH: 122
<212> TYPE: PRT
<213> ORGANISM: Homo sapiens

<400> SEQUENCE: 5

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Asn Tyr Ala Thr Ala Tyr Ala Ala
50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Ala Tyr
                85                  90                  95

Tyr Cys Ile Arg Asp Tyr Tyr Gly Ala Thr Arg Gly Phe Gln His Trp
            100                 105                 110

Gly Gln Gly Thr Leu Val Thr Val Ser Ser
            115                 120

<210> SEQ ID NO 6
<211> LENGTH: 120
<212> TYPE: PRT
<213> ORGANISM: Homo sapiens

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Val Val Gly Ala Thr Leu Asp Tyr Trp Gly Gln
            100                 105                 110

Gly Thr Leu Val Thr Val Ser Ser
        115                 120

<210> SEQ ID NO 7
<211> LENGTH: 129
<212> TYPE: PRT
<213> ORGANISM: Homo sapiens

<400> SEQUENCE: 7

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp Tyr
            20                  25                  30

Ala Met Asn Trp Val Arg Gln Ala Pro Gly Lys Gly Leu Glu Trp Val
        35                  40                  45

Gly Phe Ile Arg Ser Lys Thr Tyr Gly Gly Thr Thr Glu Tyr Ala Ala
    50                  55                  60

Ser Val Lys Gly Arg Phe Thr Ile Ser Arg Asp Asp Ser Lys Asn Ile
65                  70                  75                  80

Ala Tyr Leu Gln Met Asn Ser Leu Lys Thr Glu Asp Thr Ala Val Tyr
                85                  90                  95

Tyr Cys Thr Arg Asp Pro Ala Asp Phe Tyr Tyr Ser Ser Gly Gln
            100                 105                 110

Thr Gly Trp Phe Asp Pro Trp Gly Gln Gly Thr Leu Val Thr Val Ser
        115                 120                 125

Ser

<210> SEQ ID NO 8
<211> LENGTH: 120
<212> TYPE: PRT
<213> ORGANISM: Homo sapiens

<400> SEQUENCE: 8

Leu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

-continued

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val His Tyr Cys
                85                  90                  95

Ala Arg Asp Gly Tyr Ser Ser Trp Tyr Val Asp Tyr Trp Gly Gln
            100                 105                 110

Gly Thr Leu Val Thr Val Ser Ser
            115                 120

<210> SEQ ID NO 9
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ala Asn
            20                  25                  30

Ala Met Asn Trp Val Arg Gln Ala Ser Gly Lys Gly Leu Glu Trp Val
            35                  40                  45

Gly Arg Ile Arg Thr Lys Ser Asn Asn Tyr Ala Thr Tyr Tyr Ala Gly
    50                  55                  60

Ser Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Ala Tyr
                85                  90                  95

Tyr Cys Val Arg Asp Tyr Tyr Gly Ser Ser Ala Trp Ile Thr Tyr Trp
            100                 105                 110

Gly Gln Gly Thr Leu Val Thr Val Ser Ser
            115                 120

<210> SEQ ID NO 10
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ala Asn
            20                  25                  30

Ala Met Asn Trp Val Arg Gln Ala Pro Gly Lys Gly Leu Glu Trp Val
            35                  40                  45

Gly Arg Ile Arg Thr Lys Ser Asn Asn Tyr Ala Thr Tyr Tyr Ala Gly
    50                  55                  60

Ser Val Lys Asp Arg Phe Thr Ile Ser Arg Asp Asp Ser Lys Asn Ser
65                  70                  75                  80

```
Leu Tyr Leu Gln Met Asn Ser Leu Lys Thr Glu Asp Thr Ala Val Tyr
                85                  90                  95

Tyr Cys Val Arg Asp Tyr Tyr Gly Ser Ser Ala Trp Ile Thr Tyr Trp
            100                 105                 110

Gly Gln Gly Thr Leu Val Thr Val Ser Ser
        115                 120

<210> SEQ ID NO 11
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Asn Ala Asn
            20                  25                  30

Ala Met Asn Trp Val Arg Gln Ala Pro Gly Lys Gly Leu Glu Trp Val
        35                  40                  45

Gly Arg Ile Arg Thr Lys Ser Asn Asn Tyr Ala Thr Tyr Tyr Ala Gly
    50                  55                  60

Ser Val Lys Asp Arg Phe Thr Ile Ser Arg Asp Ser Lys Asn Ile
65                  70                  75                  80

Ala Tyr Leu Gln Met Asn Ser Leu Lys Thr Glu Asp Thr Ala Val Tyr
                85                  90                  95

Tyr Cys Val Arg Asp Tyr Tyr Gly Ser Ser Ala Trp Ile Thr Tyr Trp
            100                 105                 110

Gly Gln Gly Thr Leu Val Thr Val Ser Ser
        115                 120

<210> SEQ ID NO 12
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Leu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Ala Asn
            20                  25                  30

Ala Met Asn Trp Ile Arg Gln Ala Pro Gly Lys Gly Leu Glu Trp Val
        35                  40                  45

Ser Arg Ile Arg Thr Lys Ser Asn Asn Tyr Ala Thr Tyr Tyr Ala Gly
    50                  55                  60

Ser Val Lys Asp Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val His
                85                  90                  95

Tyr Cys Val Arg Asp Tyr Tyr Gly Ser Ser Ala Trp Ile Thr Tyr Trp
            100                 105                 110

Gly Gln Gly Thr Leu Val Thr Val Ser Ser
        115                 120
```

<210> SEQ ID NO 13
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Glu Ser Gln Thr Gln Val Phe Val Tyr Met Leu Leu Trp Leu Ser
1               5                   10                  15

Gly Val Glu Gly Asp Ile Val Met Thr Gln Ser His Lys Phe Met Ser
            20                  25                  30

Thr Ser Val Gly Asp Arg Val Ser Ile Thr Cys Lys Ala Ser Gln His
        35                  40                  45

Val Gly Thr Ala Val Ala Trp Tyr Gln Gln Lys Pro Asp Gln Ser Pro
    50                  55                  60

Lys Gln Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Tyr Pro Phe Thr Phe Gly Ser Gly Thr Lys Leu Glu Ile Lys
        115                 120                 125

<210> SEQ ID NO 14
<211> LENGTH: 95
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 15
<211> LENGTH: 101
<212> TYPE: PRT
<213> ORGANISM: Homo sapiens

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

```
Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65              70                  75                      80

Ile Ser Ser Leu Gln Ala Glu Asp Val Ala Val Tyr Tyr Cys Gln Gln
                 85                  90                  95

Tyr Tyr Ser Thr Pro
            100
```

<210> SEQ ID NO 16
<211> LENGTH: 107
<212> TYPE: PRT
<213> ORGANISM: Homo sapiens

<400> SEQUENCE: 16

```
Asp Val Val Met Thr Gln Ser Pro Ser Phe Leu Ser Ala Ser Val Gly
 1               5                  10                  15

Asp Arg Val Thr Ile Thr Cys Arg Ala Ser Gln Gly Ile Ser Asn Tyr
             20                  25                  30

Leu Ala Trp Tyr Gln Gln Arg Pro Gly Lys Ala Pro Lys Leu Leu Ile
         35                  40                  45

Tyr Ala Ala Ser Thr Leu Gln Thr Gly Val Pro Ser Arg Phe Ser Gly
 50                  55                  60

Ser Gly Ser Gly Thr Glu Phe Thr Leu Thr Ile Ser Ser Leu Gln Pro
 65              70                  75                      80

Glu Asp Phe Ala Thr Tyr Phe Cys Gln Gln Leu Gly Gly Tyr Pro Leu
                 85                  90                  95

Thr Phe Gly Gly Gly Thr Lys Leu Glu Ile Lys
            100                 105
```

<210> SEQ ID NO 17
<211> LENGTH: 113
<212> TYPE: PRT
<213> ORGANISM: Homo sapiens

<400> SEQUENCE: 17

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65              70                  75                      80

Ile Ser Ser Leu Gln Ala Glu Asp Val Ala Val Tyr Tyr Cys Gln Gln
                 85                  90                  95

Tyr Tyr Ser Thr Pro Tyr Thr Phe Gly Gln Gly Thr Lys Leu Glu Ile
            100                 105                 110

Lys
```

<210> SEQ ID NO 18
<211> LENGTH: 107
<212> TYPE: PRT
<213> ORGANISM: Homo sapiens

<400> SEQUENCE: 18

-continued

Asp Ile Gln Met Thr Gln Ser Pro Phe Ser Leu Ser Ala Ser Val Gly
1               5                   10                  15

Asp Arg Val Thr Ile Thr Cys Arg Ala Ser Gln Gly Ile Gly Ser Ser
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Leu Gln His His Asp Tyr Pro Leu
                85                  90                  95

Thr Phe Gly Gly Gly Thr Lys Leu Glu Ile Lys
            100                 105

<210> SEQ ID NO 19
<211> LENGTH: 113
<212> TYPE: PRT
<213> ORGANISM: Homo sapiens

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Ser
            20                  25                  30

Ser Asn Asn Lys Asn Tyr Leu Ala Trp Tyr Gln Gln Lys Pro Glu Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Leu Thr Phe Gly Gly Gly Thr Lys Val Glu Ile
            100                 105                 110

Lys

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Val Val Met Thr Gln Ser Pro Ser Phe Leu Ser Ala Ser Val Gly
1               5                   10                  15

Asp Arg Val Thr Ile Thr Cys Lys Ala Ser Gln His Val Gly Thr Ala
            20                  25                  30

Val Ala Trp Tyr Gln Gln Arg Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Phe
            85                  90                  95

Thr Phe Gly Gly Gly Thr Lys Leu Glu Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr Ala
            20                  25                  30

Val Ala Trp Tyr Gln Gln Lys Pro Gly Gln Pro Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Ser Ser Tyr Pro Phe
            85                  90                  95

Thr Phe Gly Gln Gly Thr Lys Leu Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Phe Ser Leu Ser Ala Ser Val Gly
1               5                   10                  15

Asp Arg Val Thr Ile Thr Cys Lys Ala Ser Gln His Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Phe
            85                  90                  95

Thr Phe Gly Gly Gly Thr Lys Leu Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln His Val Gly Thr Ala
            20                  25                  30

Val Ala Trp Tyr Gln Gln Lys Pro Glu Gln Pro Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Ser Ser Tyr Pro Phe
                85                  90                  95

Thr Phe Gly Gly Gly Thr Lys Val Glu Ile Lys
            100                 105

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Gly Trp Thr Leu Val Phe Leu Phe Leu Leu Ser Val Thr Ala Gly
1               5                   10                  15

Val His Ser

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Val Ser Ser Ala Gln Phe Leu Gly Leu Leu Leu Leu Cys Phe Gln
1               5                   10                  15

Gly Thr Arg Cys
            20

<210> SEQ ID NO 26
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 27
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

```
Val Thr Lys Ser Phe Asn Arg Gly Glu Cys
            100                 105
```

<210> SEQ ID NO 28
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Gly Trp Thr Leu Val Phe Leu Phe Leu Ser Val Thr Ala Gly
1               5                   10                  15

Val His Ser Glu Val Gln Leu Val Glu Thr Gly Gly Gly Leu Val Gln
            20                  25                  30

Pro Lys Gly Ser Met Lys Leu Ser Cys Ala Ala Ser Gly Phe Thr Phe
            35                  40                  45

Asn Ala Asn Ala Met Asn Trp Ile Arg Gln Ala Pro Gly Lys Gly Leu
50                  55                  60

Glu Trp Val Ala Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asp Ala
                85                  90                  95

Gln Asn Met Leu Tyr Leu Gln Met Asn Asp Leu Lys Thr Glu Asp Thr
            100                 105                 110

Ala Met Tyr Tyr Cys Val Arg Asp Tyr Gly Ser Ser Ala Trp Ile
            115                 120                 125

Thr Tyr Trp Gly Gln Gly Thr Leu Val Thr Val Ser Ala Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Lys Thr Tyr Thr Cys
            210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

Gln Glu Asp Pro Glu Val Gln Phe Asn Trp Tyr Val Asp Gly Val Glu
290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
```

```
                    340                 345                 350
Ile Glu Lys Thr Ile Ser Lys Ala Lys Gly Gln Pro Arg Glu Pro Gln
            355                 360                 365

Val Tyr Thr Leu Pro Pro Ser Gln Glu Glu Met Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys
465

<210> SEQ ID NO 29
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Asn Ala Asn Ala Met Asn Trp Val Arg Gln Ala Ser Gly Lys Gly Leu
    50                  55                  60

Glu Trp Val Gly Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asp Ser
                85                  90                  95

Lys Asn Thr Ala Tyr Leu Gln Met Asn Ser Leu Lys Thr Glu Asp Thr
            100                 105                 110

Ala Ala Tyr Tyr Cys Val Arg Asp Tyr Tyr Gly Ser Ser Ala Trp Ile
        115                 120                 125

Thr Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220
```

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
            245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

Gln Glu Asp Pro Glu Val Gln Phe Asn Trp Tyr Val Asp Gly Val Glu
            290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Gln Glu Glu Met Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
            435                 440                 445

Met His Glu Ala Leu His Asn His Tyr Thr Gln Lys Ser Leu Ser Leu
450                 455                 460

Ser Leu Gly Lys
465

<210> SEQ ID NO 30
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Gly Trp Thr Leu Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
            35                  40                  45

Asn Ala Asn Ala Met Asn Trp Val Arg Gln Ala Pro Gly Lys Gly Leu
    50                  55                  60

Glu Trp Val Gly Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asp Ser
            85                  90                  95

Lys Asn Ser Leu Tyr Leu Gln Met Asn Ser Leu Lys Thr Glu Asp Thr
            100                 105                 110

Ala Val Tyr Tyr Cys Val Arg Asp Tyr Tyr Gly Ser Ser Ala Trp Ile
            115                 120                 125

Thr Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
                195                 200                 205

Val Val Thr Val Pro Ser Ser Ser Leu Gly Thr Lys Thr Tyr Thr Cys
            210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
            275                 280                 285

Gln Glu Asp Pro Glu Val Gln Phe Asn Trp Tyr Val Asp Gly Val Glu
            290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
                340                 345                 350

Ile Glu Lys Thr Ile Ser Lys Ala Lys Gly Gln Pro Arg Glu Pro Gln
            355                 360                 365

Val Tyr Thr Leu Pro Pro Ser Gln Glu Glu Met Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
                420                 425                 430

Val Asp Lys Ser Arg Trp Gln Glu Gly Asn Val Phe Ser Cys Ser Val
            435                 440                 445

Met His Glu Ala Leu His Asn His Tyr Thr Gln Lys Ser Leu Ser Leu
450                 455                 460

Ser Leu Gly Lys
465

<210> SEQ ID NO 31
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Gly Trp Thr Leu Val Phe Leu Phe Leu Ser Val Thr Ala Gly
1               5                   10                  15

Val His Ser Glu Val Gln Leu Val Glu Ser Gly Gly Gly Leu Val Gln
            20                  25                  30

Pro Gly Arg Ser Leu Arg Leu Ser Cys Thr Ala Ser Gly Phe Thr Phe
        35                  40                  45

Asn Ala Asn Ala Met Asn Trp Val Arg Gln Ala Pro Gly Lys Gly Leu
    50                  55                  60

Glu Trp Val Gly Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asp Ser
                85                  90                  95

Lys Asn Ile Ala Tyr Leu Gln Met Asn Ser Leu Lys Thr Glu Asp Thr
            100                 105                 110

Ala Val Tyr Tyr Cys Val Arg Asp Tyr Tyr Gly Ser Ala Trp Ile
        115                 120                 125

Thr Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

```
Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
            435                 440                 445

Met His Glu Ala Leu His Asn His Tyr Thr Gln Lys Ser Leu Ser Leu
450                 455                 460

Ser Leu Gly Lys
465

<210> SEQ ID NO 32
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Gly Trp Thr Leu Val Phe Leu Phe Leu Leu Ser Val Thr Ala Gly
1               5                   10                  15

Val His Ser Leu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Asn Ala Asn Ala Met Asn Trp Ile Arg Gln Ala Pro Gly Lys Gly Leu
    50                  55                  60

Glu Trp Val Ser Arg Ile Arg Thr Lys Ser Asn Asn Tyr Ala Thr Tyr
65                  70                  75                  80

Tyr Ala Gly Ser Val Lys Asp Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val His Tyr Cys Val Arg Asp Tyr Tyr Gly Ser Ser Ala Trp Ile
        115                 120                 125

Thr Tyr Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Pro Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
```

```
                  290                 295                 300
Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys
465

<210> SEQ ID NO 33
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Val Ser Ser Ala Gln Phe Leu Gly Leu Leu Leu Leu Cys Phe Gln
1               5                   10                  15

Gly Thr Arg Cys Asp Ile Val Met Thr Gln Ser His Lys Phe Met Ser
            20                  25                  30

Thr Ser Val Gly Asp Arg Val Ser Ile Thr Cys Lys Ala Ser Gln His
        35                  40                  45

Val Gly Thr Ala Val Ala Trp Tyr Gln Gln Lys Pro Asp Gln Ser Pro
    50                  55                  60

Lys Gln Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Tyr Pro Phe Thr Phe Gly Ser Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175
```

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 34
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Val Ser Ser Ala Gln Phe Leu Gly Leu Leu Leu Leu Cys Phe Gln
1               5                   10                  15

Gly Thr Arg Cys Asp Val Val Met Thr Gln Ser Pro Ser Phe Leu Ser
            20                  25                  30

Ala Ser Val Gly Asp Arg Val Thr Ile Thr Cys Lys Ala Ser Gln His
        35                  40                  45

Val Gly Thr Ala Val Ala Trp Tyr Gln Gln Arg Pro Gly Lys Ala Pro
    50                  55                  60

Lys Leu Leu Ile Tyr Trp Ala Ser Thr Arg His Thr Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Phe Cys Gln Gln Tyr Ser
            100                 105                 110

Ser Tyr Pro Phe Thr Phe Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 35
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Val Ser Ser Ala Gln Phe Leu Gly Leu Leu Leu Cys Phe Gln
1               5                   10                  15

Gly Thr Arg Cys Asp Ile Val Met Thr Gln Ser Pro Asp Ser Leu Ala
            20                  25                  30

Val Ser Leu Gly Glu Arg Ala Thr Ile Asn Cys Lys Ala Ser Gln His
        35                  40                  45

Val Gly Thr Ala Val Ala Trp Tyr Gln Gln Lys Pro Gly Gln Pro Pro
    50                  55                  60

Lys Leu Leu Ile Tyr Trp Ala Ser Thr Arg His Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Val Tyr Tyr Cys Gln Gln Tyr Ser
            100                 105                 110

Ser Tyr Pro Phe Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 36
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Val Ser Ser Ala Gln Phe Leu Gly Leu Leu Leu Cys Phe Gln
1               5                   10                  15

Gly Thr Arg Cys Asp Ile Gln Met Thr Gln Ser Pro Phe Ser Leu Ser
            20                  25                  30

Ala Ser Val Gly Asp Arg Val Thr Ile Thr Cys Lys Ala Ser Gln His
        35                  40                  45

Val Gly Thr Ala Val Ala Trp Tyr Gln Gln Lys Pro Gly Lys Ala Pro
    50                  55                  60

Lys Leu Leu Ile Tyr Trp Ala Ser Thr Arg His Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Phe Cys Gln Gln Tyr Ser
            100                 105                 110

Ser Tyr Pro Phe Thr Phe Gly Gly Gly Thr Lys Leu Glu Ile Lys Arg
        115                 120                 125

```
Thr Val Ala Ala Pro Ser Val Phe Ile Phe Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230
```

<210> SEQ ID NO 37
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Met Val Ser Ser Ala Gln Phe Leu Gly Leu Leu Leu Leu Cys Phe Gln
1               5                   10                  15

Gly Thr Arg Cys Asp Ile Val Met Thr Gln Ser Pro Asp Ser Leu Ala
                20                  25                  30

Val Ser Leu Gly Glu Arg Ala Thr Ile Asn Cys Lys Ala Ser Gln His
            35                  40                  45

Val Gly Thr Ala Val Ala Trp Tyr Gln Gln Lys Pro Glu Gln Pro Pro
        50                  55                  60

Lys Leu Leu Ile Tyr Trp Ala Ser Thr Arg His Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Val Tyr Tyr Cys Gln Gln Tyr Ser
                100                 105                 110

Ser Tyr Pro Phe Thr Phe Gly Gly Gly Thr Lys Val Glu Ile Lys Arg
            115                 120                 125

Thr Val Ala Ala Pro Ser Val Phe Ile Phe Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230
```

```
<210> SEQ ID NO 38
<211> LENGTH: 760
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Glu Trp Ser Trp Val Phe Leu Phe Phe Leu Ser Val Thr Thr Gly
1               5                   10                  15

Val His Ser Glu Pro Glu Arg Cys Asn Phe Thr Leu Ala Glu Ser Lys
            20                  25                  30

Ala Ser Ser His Ser Val Ser Ile Gln Trp Arg Ile Leu Gly Ser Pro
        35                  40                  45

Cys Asn Phe Ser Leu Ile Tyr Ser Ser Asp Thr Leu Gly Ala Ala Leu
    50                  55                  60

Cys Pro Thr Phe Arg Ile Asp Asn Thr Thr Tyr Gly Cys Asn Leu Gln
65                  70                  75                  80

Asp Leu Gln Ala Gly Thr Ile Tyr Asn Phe Lys Ile Ile Ser Leu Asp
                85                  90                  95

Glu Glu Arg Thr Val Val Leu Gln Thr Asp Pro Leu Pro Pro Ala Arg
            100                 105                 110

Phe Gly Val Ser Lys Glu Lys Thr Thr Ser Thr Gly Leu His Val Trp
        115                 120                 125

Trp Thr Pro Ser Ser Gly Lys Val Thr Ser Tyr Glu Val Gln Leu Phe
    130                 135                 140

Asp Glu Asn Asn Gln Lys Ile Gln Gly Val Gln Ile Gln Glu Ser Thr
145                 150                 155                 160

Ser Trp Asn Glu Tyr Thr Phe Phe Asn Leu Thr Ala Gly Ser Lys Tyr
                165                 170                 175

Asn Ile Ala Ile Thr Ala Val Ser Gly Gly Lys Arg Ser Phe Ser Val
            180                 185                 190

Tyr Thr Asn Gly Ser Thr Val Pro Ser Pro Val Lys Asp Ile Gly Ile
        195                 200                 205

Ser Thr Lys Ala Asn Ser Leu Leu Ile Ser Trp Ser His Gly Ser Gly
    210                 215                 220

Asn Val Glu Arg Tyr Arg Leu Met Leu Met Asp Lys Gly Ile Leu Val
225                 230                 235                 240

His Gly Gly Val Val Asp Lys His Ala Thr Ser Tyr Ala Phe His Gly
                245                 250                 255

Leu Thr Pro Gly Tyr Leu Tyr Asn Leu Thr Val Met Thr Glu Ala Ala
            260                 265                 270

Gly Leu Gln Asn Tyr Arg Trp Lys Leu Val Arg Thr Ala Pro Met Glu
        275                 280                 285

Val Ser Asn Leu Lys Val Thr Asn Asp Gly Ser Leu Thr Ser Leu Lys
    290                 295                 300

Val Lys Trp Gln Arg Pro Pro Gly Asn Val Asp Ser Tyr Asn Ile Thr
305                 310                 315                 320

Leu Ser His Lys Gly Thr Ile Lys Glu Ser Arg Val Leu Ala Pro Trp
                325                 330                 335

Ile Thr Glu Thr His Phe Lys Glu Leu Val Pro Gly Arg Leu Tyr Gln
            340                 345                 350

Val Thr Val Ser Cys Val Ser Gly Glu Leu Ser Ala Gln Lys Met Ala
        355                 360                 365
```

-continued

```
Val Gly Arg Thr Phe Pro Leu Ala Val Leu Gln Leu Arg Val Lys His
    370                 375                 380

Ala Asn Glu Thr Ser Leu Ser Ile Met Trp Gln Thr Pro Val Ala Glu
385                 390                 395                 400

Trp Glu Lys Tyr Ile Ile Ser Leu Ala Asp Arg Asp Leu Leu Leu Ile
                405                 410                 415

His Lys Ser Leu Ser Lys Asp Ala Lys Glu Phe Thr Phe Thr Asp Leu
            420                 425                 430

Val Pro Gly Arg Lys Tyr Met Ala Thr Val Thr Ser Ile Ser Gly Asp
        435                 440                 445

Leu Lys Asn Ser Ser Val Lys Gly Arg Thr Val Pro Ala Gln Val
    450                 455                 460

Thr Asp Leu His Val Ala Asn Gln Gly Met Thr Ser Ser Leu Phe Thr
465                 470                 475                 480

Asn Trp Thr Gln Ala Gln Gly Asp Val Glu Phe Tyr Gln Val Leu Leu
                485                 490                 495

Ile His Glu Asn Val Val Ile Lys Asn Glu Ser Ile Ser Ser Glu Thr
            500                 505                 510

Ser Arg Tyr Ser Phe His Ser Leu Lys Ser Gly Ser Leu Tyr Ser Val
        515                 520                 525

Val Val Thr Thr Val Ser Gly Gly Ile Ser Ser Arg Gln Val Val Val
    530                 535                 540

Glu Gly Arg Thr Val Pro Ser Ser Val Ser Gly Val Thr Val Asn Asn
545                 550                 555                 560

Ser Gly Arg Asn Asp Tyr Leu Ser Val Ser Trp Leu Leu Ala Pro Gly
                565                 570                 575

Asp Val Asp Asn Tyr Glu Val Thr Leu Ser His Asp Gly Lys Val Val
            580                 585                 590

Gln Ser Leu Val Ile Ala Lys Ser Val Arg Glu Cys Ser Phe Ser Ser
        595                 600                 605

Leu Thr Pro Gly Arg Leu Tyr Thr Val Thr Ile Thr Thr Arg Ser Gly
    610                 615                 620

Lys Tyr Glu Asn His Ser Phe Ser Gln Glu Arg Thr Val Pro Asp Lys
625                 630                 635                 640

Val Gln Gly Val Ser Val Ser Asn Ser Ala Arg Ser Asp Tyr Leu Arg
                645                 650                 655

Val Ser Trp Val His Ala Thr Gly Asp Phe Asp His Tyr Glu Val Thr
            660                 665                 670

Ile Lys Asn Lys Asn Asn Phe Ile Gln Thr Lys Ser Ile Pro Lys Ser
        675                 680                 685

Glu Asn Glu Cys Val Phe Val Gln Leu Val Pro Gly Arg Leu Tyr Ser
    690                 695                 700

Val Thr Val Thr Thr Lys Ser Gly Gln Tyr Glu Ala Asn Glu Gln Gly
705                 710                 715                 720

Asn Gly Arg Thr Ile Pro Glu Lys Gly Asn Ser Ala Asp Ile Gln His
                725                 730                 735

Ser Gly Gly Arg Ser Ser Leu Glu Gly Pro Arg Phe Glu Arg Thr Gly
            740                 745                 750

Gly Gly His His His His His
        755                 760

<210> SEQ ID NO 39
<211> LENGTH: 1997
<212> TYPE: PRT
```

<213> ORGANISM: Homo sapiens

<400> SEQUENCE: 39

```
Met Leu Ser His Gly Ala Gly Leu Ala Leu Trp Ile Thr Leu Ser Leu
1               5                   10                  15

Leu Gln Thr Gly Leu Ala Glu Pro Glu Arg Cys Asn Phe Thr Leu Ala
            20                  25                  30

Glu Ser Lys Ala Ser Ser His Ser Val Ser Ile Gln Trp Arg Ile Leu
        35                  40                  45

Gly Ser Pro Cys Asn Phe Ser Leu Ile Tyr Ser Ser Asp Thr Leu Gly
    50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Arg Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Ser Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190

Phe Ser Val Tyr Thr Asn Gly Ser Thr Val Pro Ser Pro Val Lys Asp
        195                 200                 205

Ile Gly Ile Ser Thr Lys Ala Asn Ser Leu Leu Ile Ser Trp Ser His
    210                 215                 220

Gly Ser Gly Asn Val Glu Arg Tyr Arg Leu Met Leu Met Asp Lys Gly
225                 230                 235                 240

Ile Leu Val His Gly Gly Val Val Asp Lys His Ala Thr Ser Tyr Ala
                245                 250                 255

Phe His Gly Leu Thr Pro Gly Tyr Leu Tyr Asn Leu Thr Val Met Thr
            260                 265                 270

Glu Ala Ala Gly Leu Gln Asn Tyr Arg Trp Lys Leu Val Arg Thr Ala
        275                 280                 285

Pro Met Glu Val Ser Asn Leu Lys Val Thr Asn Asp Gly Ser Leu Thr
    290                 295                 300

Ser Leu Lys Val Lys Trp Gln Arg Pro Pro Gly Asn Val Asp Ser Tyr
305                 310                 315                 320

Asn Ile Thr Leu Ser His Lys Gly Thr Ile Lys Glu Ser Arg Val Leu
                325                 330                 335

Ala Pro Trp Ile Thr Glu Thr His Phe Lys Glu Leu Val Pro Gly Arg
            340                 345                 350

Leu Tyr Gln Val Thr Val Ser Cys Val Ser Gly Glu Leu Ser Ala Gln
        355                 360                 365

Lys Met Ala Val Gly Arg Thr Phe Pro Asp Lys Val Ala Asn Leu Glu
    370                 375                 380

Ala Asn Asn Asn Gly Arg Met Arg Ser Leu Val Val Ser Trp Ser Pro
385                 390                 395                 400
```

```
Pro Ala Gly Asp Trp Glu Gln Tyr Arg Ile Leu Phe Asn Asp Ser
                405                 410                 415

Val Val Leu Leu Asn Ile Thr Val Gly Lys Glu Glu Thr Gln Tyr Val
        420                 425                 430

Met Asp Asp Thr Gly Leu Val Pro Gly Arg Gln Tyr Glu Val Glu Val
        435                 440                 445

Ile Val Glu Ser Gly Asn Leu Lys Asn Ser Glu Arg Cys Gln Gly Arg
    450                 455                 460

Thr Val Pro Leu Ala Val Leu Gln Leu Arg Val Lys His Ala Asn Glu
465                 470                 475                 480

Thr Ser Leu Ser Ile Met Trp Gln Thr Pro Val Ala Glu Trp Glu Lys
                485                 490                 495

Tyr Ile Ile Ser Leu Ala Asp Arg Asp Leu Leu Ile His Lys Ser
                500                 505                 510

Leu Ser Lys Asp Ala Lys Glu Phe Thr Phe Thr Asp Leu Val Pro Gly
        515                 520                 525

Arg Lys Tyr Met Ala Thr Val Thr Ser Ile Ser Gly Asp Leu Lys Asn
        530                 535                 540

Ser Ser Ser Val Lys Gly Arg Thr Val Pro Ala Gln Val Thr Asp Leu
545                 550                 555                 560

His Val Ala Asn Gln Gly Met Thr Ser Ser Leu Phe Thr Asn Trp Thr
                565                 570                 575

Gln Ala Gln Gly Asp Val Glu Phe Tyr Gln Val Leu Leu Ile His Glu
                580                 585                 590

Asn Val Val Ile Lys Asn Glu Ser Ile Ser Ser Glu Thr Ser Arg Tyr
            595                 600                 605

Ser Phe His Ser Leu Lys Ser Gly Ser Leu Tyr Ser Val Val Thr
        610                 615                 620

Thr Val Ser Gly Gly Ile Ser Ser Arg Gln Val Val Glu Gly Arg
625                 630                 635                 640

Thr Val Pro Ser Ser Val Ser Gly Val Thr Val Asn Asn Ser Gly Arg
                645                 650                 655

Asn Asp Tyr Leu Ser Val Ser Trp Leu Leu Ala Pro Gly Asp Val Asp
            660                 665                 670

Asn Tyr Glu Val Thr Leu Ser His Asp Gly Lys Val Val Gln Ser Leu
        675                 680                 685

Val Ile Ala Lys Ser Val Arg Glu Cys Ser Phe Ser Ser Leu Thr Pro
    690                 695                 700

Gly Arg Leu Tyr Thr Val Thr Ile Thr Thr Arg Ser Gly Lys Tyr Glu
705                 710                 715                 720

Asn His Ser Phe Ser Gln Glu Arg Thr Val Pro Asp Lys Val Gln Gly
                725                 730                 735

Val Ser Val Ser Asn Ser Ala Arg Ser Asp Tyr Leu Arg Val Ser Trp
                740                 745                 750

Val His Ala Thr Gly Asp Phe Asp His Tyr Glu Val Thr Ile Lys Asn
        755                 760                 765

Lys Asn Asn Phe Ile Gln Thr Lys Ser Ile Pro Lys Ser Glu Asn Glu
        770                 775                 780

Cys Val Phe Val Gln Leu Val Pro Gly Arg Leu Tyr Ser Val Thr Val
785                 790                 795                 800

Thr Thr Lys Ser Gly Gln Tyr Glu Ala Asn Glu Gln Gly Asn Gly Arg
                805                 810                 815

Thr Ile Pro Glu Pro Val Lys Asp Leu Thr Leu Arg Asn Arg Ser Thr
```

```
                820             825             830
Glu Asp Leu His Val Thr Trp Ser Gly Ala Asn Gly Asp Val Asp Gln
            835             840             845
Tyr Glu Ile Gln Leu Leu Phe Asn Asp Met Lys Val Phe Pro Pro Phe
        850             855             860
His Leu Val Asn Thr Ala Thr Glu Tyr Arg Phe Thr Ser Leu Thr Pro
865             870             875             880
Gly Arg Gln Tyr Lys Ile Leu Val Leu Thr Ile Ser Gly Asp Val Gln
                885             890             895
Gln Ser Ala Phe Ile Glu Gly Phe Thr Val Pro Ser Ala Val Lys Asn
            900             905             910
Ile His Ile Ser Pro Asn Gly Ala Thr Asp Ser Leu Thr Val Asn Trp
        915             920             925
Thr Pro Gly Gly Gly Asp Val Asp Ser Tyr Thr Val Ser Ala Phe Arg
        930             935             940
His Ser Gln Lys Val Asp Ser Gln Thr Ile Pro Lys His Val Phe Glu
945             950             955             960
His Thr Phe His Arg Leu Glu Ala Gly Glu Gln Tyr Gln Ile Met Ile
                965             970             975
Ala Ser Val Ser Gly Ser Leu Lys Asn Gln Ile Asn Val Val Gly Arg
            980             985             990
Thr Val Pro Ala Ser Val Gln Gly  Val Ile Ala Asp Asn  Ala Tyr Ser
        995             1000            1005
Ser Tyr  Ser Leu Ile Val Ser  Trp Gln Lys Ala Ala  Gly Val Ala
    1010            1015            1020
Glu Arg  Tyr Asp Ile Leu Leu  Leu Thr Glu Asn Gly  Ile Leu Leu
    1025            1030            1035
Arg Asn  Thr Ser Glu Pro Ala  Thr Thr Lys Gln His  Lys Phe Glu
    1040            1045            1050
Asp Leu  Thr Pro Gly Lys Lys  Tyr Lys Ile Gln Ile  Leu Thr Val
    1055            1060            1065
Ser Gly  Gly Leu Phe Ser Lys  Glu Ala Gln Thr Glu  Gly Arg Thr
    1070            1075            1080
Val Pro  Ala Ala Val Thr Asp  Leu Arg Ile Thr Glu  Asn Ser Thr
    1085            1090            1095
Arg His  Leu Ser Phe Arg Trp  Thr Ala Ser Glu Gly  Glu Leu Ser
    1100            1105            1110
Trp Tyr  Asn Ile Phe Leu Tyr  Asn Pro Asp Gly Asn  Leu Gln Glu
    1115            1120            1125
Arg Ala  Gln Val Asp Pro Leu  Val Gln Ser Phe Ser  Phe Gln Asn
    1130            1135            1140
Leu Leu  Gln Gly Arg Met Tyr  Lys Met Val Ile Val  Thr His Ser
    1145            1150            1155
Gly Glu  Leu Ser Asn Glu Ser  Phe Ile Phe Gly Arg  Thr Val Pro
    1160            1165            1170
Ala Ser  Val Ser His Leu Arg  Gly Ser Asn Arg Asn  Thr Thr Asp
    1175            1180            1185
Ser Leu  Trp Phe Asn Trp Ser  Pro Ala Ser Gly Asp  Phe Asp Phe
    1190            1195            1200
Tyr Glu  Leu Ile Leu Tyr Asn  Pro Asn Gly Thr Lys  Lys Glu Asn
    1205            1210            1215
Trp Lys  Asp Lys Asp Leu Thr  Glu Trp Arg Phe Gln  Gly Leu Val
    1220            1225            1230
```

```
Pro Gly Arg Lys Tyr Val Leu Trp Val Val Thr His Ser Gly Asp
    1235            1240            1245

Leu Ser Asn Lys Val Thr Ala Glu Ser Arg Thr Ala Pro Ser Pro
    1250            1255            1260

Pro Ser Leu Met Ser Phe Ala Asp Ile Ala Asn Thr Ser Leu Ala
    1265            1270            1275

Ile Thr Trp Lys Gly Pro Pro Asp Trp Thr Asp Tyr Asn Asp Phe
    1280            1285            1290

Glu Leu Gln Trp Leu Pro Arg Asp Ala Leu Thr Val Phe Asn Pro
    1295            1300            1305

Tyr Asn Asn Arg Lys Ser Glu Gly Arg Ile Val Tyr Gly Leu Arg
    1310            1315            1320

Pro Gly Arg Ser Tyr Gln Phe Asn Val Lys Thr Val Ser Gly Asp
    1325            1330            1335

Ser Trp Lys Thr Tyr Ser Lys Pro Ile Phe Gly Ser Val Arg Thr
    1340            1345            1350

Lys Pro Asp Lys Ile Gln Asn Leu His Cys Arg Pro Gln Asn Ser
    1355            1360            1365

Thr Ala Ile Ala Cys Ser Trp Ile Pro Pro Asp Ser Asp Phe Asp
    1370            1375            1380

Gly Tyr Ser Ile Glu Cys Arg Lys Met Asp Thr Gln Glu Val Glu
    1385            1390            1395

Phe Ser Arg Lys Leu Glu Lys Glu Lys Ser Leu Leu Asn Ile Met
    1400            1405            1410

Met Leu Val Pro His Lys Arg Tyr Leu Val Ser Ile Lys Val Gln
    1415            1420            1425

Ser Ala Gly Met Thr Ser Glu Val Val Glu Asp Ser Thr Ile Thr
    1430            1435            1440

Met Ile Asp Arg Pro Pro Pro Pro Pro Pro His Ile Arg Val Asn
    1445            1450            1455

Glu Lys Asp Val Leu Ile Ser Lys Ser Ser Ile Asn Phe Thr Val
    1460            1465            1470

Asn Cys Ser Trp Phe Ser Asp Thr Asn Gly Ala Val Lys Tyr Phe
    1475            1480            1485

Thr Val Val Val Arg Glu Ala Asp Gly Ser Asp Glu Leu Lys Pro
    1490            1495            1500

Glu Gln Gln His Pro Leu Pro Ser Tyr Leu Glu Tyr Arg His Asn
    1505            1510            1515

Ala Ser Ile Arg Val Tyr Gln Thr Asn Tyr Phe Ala Ser Lys Cys
    1520            1525            1530

Ala Glu Asn Pro Asn Ser Asn Ser Lys Ser Phe Asn Ile Lys Leu
    1535            1540            1545

Gly Ala Glu Met Glu Ser Leu Gly Gly Lys Cys Asp Pro Thr Gln
    1550            1555            1560

Gln Lys Phe Cys Asp Gly Pro Leu Lys Pro His Thr Ala Tyr Arg
    1565            1570            1575

Ile Ser Ile Arg Ala Phe Thr Gln Leu Phe Asp Glu Asp Leu Lys
    1580            1585            1590

Glu Phe Thr Lys Pro Leu Tyr Ser Asp Thr Phe Phe Ser Leu Pro
    1595            1600            1605

Ile Thr Thr Glu Ser Glu Pro Leu Phe Gly Ala Ile Glu Gly Val
    1610            1615            1620
```

```
Ser Ala Gly Leu Phe Leu Ile Gly Met Leu Val Ala Val Val Ala
1625                1630                1635

Leu Leu Ile Cys Arg Gln Lys Val Ser His Gly Arg Glu Arg Pro
1640                1645                1650

Ser Ala Arg Leu Ser Ile Arg Arg Asp Arg Pro Leu Ser Val His
1655                1660                1665

Leu Asn Leu Gly Gln Lys Gly Asn Arg Lys Thr Ser Cys Pro Ile
1670                1675                1680

Lys Ile Asn Gln Phe Glu Gly His Phe Met Lys Leu Gln Ala Asp
1685                1690                1695

Ser Asn Tyr Leu Leu Ser Lys Glu Tyr Glu Leu Lys Asp Val
1700                1705                1710

Gly Arg Asn Gln Ser Cys Asp Ile Ala Leu Leu Pro Glu Asn Arg
1715                1720                1725

Gly Lys Asn Arg Tyr Asn Asn Ile Leu Pro Tyr Asp Ala Thr Arg
1730                1735                1740

Val Lys Leu Ser Asn Val Asp Asp Pro Cys Ser Asp Tyr Ile
1745                1750                1755

Asn Ala Ser Tyr Ile Pro Gly Asn Asn Phe Arg Arg Glu Tyr Ile
1760                1765                1770

Val Thr Gln Gly Pro Leu Pro Gly Thr Lys Asp Asp Phe Trp Lys
1775                1780                1785

Met Val Trp Glu Gln Asn Val His Asn Ile Val Met Val Thr Gln
1790                1795                1800

Cys Val Glu Lys Gly Arg Val Lys Cys Asp His Tyr Trp Pro Ala
1805                1810                1815

Asp Gln Asp Ser Leu Tyr Tyr Gly Asp Leu Ile Leu Gln Met Leu
1820                1825                1830

Ser Glu Ser Val Leu Pro Glu Trp Thr Ile Arg Glu Phe Lys Ile
1835                1840                1845

Cys Gly Glu Glu Gln Leu Asp Ala His Arg Leu Ile Arg His Phe
1850                1855                1860

His Tyr Thr Val Trp Pro Asp His Gly Val Pro Glu Thr Thr Gln
1865                1870                1875

Ser Leu Ile Gln Phe Val Arg Thr Val Arg Asp Tyr Ile Asn Arg
1880                1885                1890

Ser Pro Gly Ala Gly Pro Thr Val Val His Cys Ser Ala Gly Val
1895                1900                1905

Gly Arg Thr Gly Thr Phe Ile Ala Leu Asp Arg Ile Leu Gln Gln
1910                1915                1920

Leu Asp Ser Lys Asp Ser Val Asp Ile Tyr Gly Ala Val His Asp
1925                1930                1935

Leu Arg Leu His Arg Val His Met Val Gln Thr Glu Cys Gln Tyr
1940                1945                1950

Val Tyr Leu His Gln Cys Val Arg Asp Val Leu Arg Ala Arg Lys
1955                1960                1965

Leu Arg Ser Glu Gln Glu Asn Pro Leu Phe Pro Ile Tyr Glu Asn
1970                1975                1980

Val Asn Pro Glu Tyr His Arg Asp Pro Val Tyr Ser Arg His
1985                1990                1995

<210> SEQ ID NO 40
<211> LENGTH: 2283
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 40

```
atggaatgga gctgggtctt tctcttcttc ctgtcagtaa cgactggtgt ccactccgag      60
cccgagagat gcaacttcac cctggccgag tccaaggcct cctcccactc cgtgtctatc     120
cagtggcgga tcctgggctc ccctgcaac ttctctctga tctactcctc cgacaccctg      180
ggcgctgccc tgtgccctac cttcagaatc gacaacacca cctacggctg caacctgcag     240
gatctgcagg ccggcaccat ctacaacttc aagatcatct ccctggacga ggaacggacc     300
gtggtgctgc agaccgatcc tctgcctcct gccagattcg gcgtgtccaa agaaaagacc     360
acctccaccg gactgcacgt gtggtggacc ccttccagcg gcaaagtgac ctcctacgag     420
gtgcagctgt tcgacgagaa caaccagaaa atccagggcg tgcagatcca ggaatccacc     480
tcctggaacg agtacacctt cttcaacctg accgccggct ccaagtacaa tatcgccatc     540
accgccgtgt ccggcggcaa gagatccttc tccgtgtaca ccaacggctc caccgtgccc     600
agccccgtga aggacatcgg catctccacc aaggccaact ccctgctgat ctcctggtcc     660
cacggctccg gcaacgtgga acggtacaga ctgatgctga tggacaaggg catcctggtg     720
cacggcggcg tggtggataa gcacgccacc tcttacgcct ccacggcct gaccctggc      780
tacctgtaca atctgaccgt gatgaccgag gccgctggac tgcagaacta ccggtggaag     840
ctcgtgcgga ccgcccccat ggaagtgtcc aacctgaaag tgaccaacga cggctccctg     900
acctctctga agtgaagtg gcagaggccc cctggcaatg tggactccta acatcacc      960
ctgtcccaca gggcaccat caagaatcc cgggtgctgg ccccttggat caccgagaca     1020
cacttcaaag aactggtgcc tggccggctg taccaagtga ccgtgtcctg tgtgtctggc     1080
gagctgtccg cccagaaaat ggccgtgggc agaaccttcc ctctggccgt gctgcagctg     1140
agagtgaagc acgctaacga acatccctg tccatcatgt ggcagacccc cgtggccgag     1200
tgggagaagt acatcatcag cctggccgac cgggacctgc tgctgatcca aagtccctg     1260
agcaaggacg ccaaagagtt caccttcacc gacctggtgc ccggcagaaa gtacatggcc     1320
accgtgacct ccatctccgg cgacctgaag aactcctcca gcgtgaaggg caggaccgtg     1380
cctgcccaag tgacagacct gcacgtggcc aaccagggca tgacctcctc cctgttcacc     1440
aactggaccc aggctcaggg cgacgtggaa ttctaccagg tgctgctgat tcatgagaac     1500
gtcgtgatca agaacgagtc catctcctcc gagacaagcc ggtactcctt ccactccctg     1560
aagtccggca gcctgtactc cgtggtcgtg accacagtgt ccggggcat ctcctctaga     1620
caggtggtgg tggaaggccg caccgtgcct agttcagtgt caggcgtgac cgtgaacaac     1680
agcggccgga acgactacct gtccgtgtct ggctgctgg ctcctgggga cgtggacaac     1740
tacgaagtga ccctgagcca cgacggcaag gtggtgcagt ctctcgtgat cgccaagtcc     1800
gtgcgcgagt gctccttcag ctctctgaca cctggcagac tgtataccgt gaccatcacc     1860
accagatccg ggaagtacga gaaccacagc ttctcccagg aacgcacagt gcccgacaag     1920
gtgcagggcg tgtcagtgtc taactccgcc agatctgact acctgcgggt gtcctgggtg     1980
cacgctaccg gcgacttcga ccattatgaa gtgacaatca agaacaagaa caacttcatc     2040
cagaccaagt ccatccccaa gtccgagaac gagtgcgtgt tcgtgcagct ggtgccaggc     2100
agactgtact ctgtgacagt gaccaccaag tccggccagt acgaggccaa cgagcagggc     2160
```

```
aacggcagga ccatccctga aagggcaac tccgccgaca tccagcactc tggcggcaga    2220
tcctctctgg aaggccccag attcgagaga accggcggag ccaccacca tcatcaccat    2280 tga                                                                  2283
```

<210> SEQ ID NO 41
<211> LENGTH: 736
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Met Glu Trp Ser Trp Val Phe Leu Phe Phe Leu Ser Val Thr Thr Gly
1               5                   10                  15

Val His Ser Glu Arg Cys Asn Phe Thr Leu Ala Glu Ser Lys Ala Ser
            20                  25                  30

Ser His Ser Val Ser Ile Arg Trp Arg Ile Trp Gly Ser Pro Cys Asn
        35                  40                  45

Phe Asn Leu Thr Tyr Ser Ser Asp Thr Leu Gly Ala Ala Ser Cys Pro
    50                  55                  60

Pro Phe Arg Leu Asp Asn Thr Thr Tyr Gly Cys Asn Leu Gln Asp Leu
65                  70                  75                  80

Gln Ala Gly Thr Ile Tyr Asn Phe Arg Ile Val Ser Leu Asp Gly Glu
                85                  90                  95

Glu Arg Thr Val Val Leu Gln Thr Asp Pro Leu Pro Pro Ala Arg Phe
            100                 105                 110

Gly Val Ser Lys Glu Lys Thr Thr Ser Thr Ser Leu His Val Trp Trp
        115                 120                 125

Thr Pro Ser Pro Gly Lys Val Thr Ser Tyr Glu Val Gln Leu Phe Asp
    130                 135                 140

Glu Asn Asn Gln Lys Ile Gln Gly Val Gln Ile Gln Glu Ser Thr Ser
145                 150                 155                 160

Trp Asn Lys Tyr Thr Phe Phe Asn Leu Thr Ala Gly Ser Lys Tyr Asn
                165                 170                 175

Ile Thr Ile Thr Ala Val Ser Gly Gly Lys Arg Ser Ser Ser Val Tyr
            180                 185                 190

Thr Asn Gly Ser Thr Val Pro Ser Pro Val Lys Asp Ile Gly Ile Ser
        195                 200                 205

Thr Lys Ala Asn Ser Leu Leu Val Ser Trp Ser His Gly Ser Gly Asn
    210                 215                 220

Val Glu Arg Tyr Arg Leu Met Leu Met Asp Lys Gly Ile Leu Val His
225                 230                 235                 240

Gly Ser Val Val Asp Arg Gln Ala Thr Ser Tyr Thr Phe Asn Gly Leu
                245                 250                 255

Thr Pro Gly Tyr Leu Tyr Asn Leu Thr Val Thr Glu Ala Ala Gly
            260                 265                 270 Gly

Leu Gln Asn Tyr Lys Trp Lys Leu Val Arg Thr Ala Pro Met Glu Val
        275                 280                 285

Ser Asn Leu Lys Val Thr Asn Asp Gly Ser Leu Thr Ser Leu Lys Val
    290                 295                 300

Lys Trp Gln Arg Pro Pro Gly Asn Val Asp Ser Tyr Asn Ile Thr Leu
305                 310                 315                 320

Ser His Lys Gly Thr Ile Lys Glu Ser Arg Val Leu Ala Pro Arg Val
                325                 330                 335
```

```
Thr Glu Thr His Phe Lys Glu Leu Thr Pro Gly Arg Leu Tyr Gln Val
            340                 345                 350

Thr Val Ser Cys Val Ser Gly Glu Leu Ser Ala Gln Arg Met Ala Val
            355                 360                 365

Gly Arg Thr Phe Pro Leu Pro Val Leu Gln Leu Arg Val Lys His Ala
370                 375                 380

Asn Glu Thr Ser Leu Ser Ile Ile Trp Gln Pro Pro Val Ala Glu Trp
385                 390                 395                 400

Glu Glu Tyr Ile Ile Ser Leu Ala Asp Arg Asp Leu Arg Leu Ile His
            405                 410                 415

Lys Ser Leu Ser Lys Asp Ala Lys Glu Phe Thr Phe Thr Asp Leu Val
            420                 425                 430

Pro Gly Arg Lys Tyr Met Ala Thr Val Thr Ser Ile Ser Gly Asp Leu
            435                 440                 445

Lys Asn Ser Ser Ser Val Lys Gly Arg Thr Val Pro Ala Gln Val Thr
450                 455                 460

Asp Leu His Val Ala Asn Gln Gly Met Thr Ser Ser Leu Phe Thr Asn
465                 470                 475                 480

Trp Thr Gln Ala Gln Gly Asp Val Glu Phe Tyr Gln Val Leu Leu Ile
            485                 490                 495

His Glu Asn Val Val Ile Lys Asn Glu Ser Ile Pro Ser Glu Thr Ser
            500                 505                 510

Gly Tyr Asn Phe His Phe Leu Lys Ser Gly Ser Leu Tyr Ser Val Val
            515                 520                 525

Val Thr Thr Val Ser Gly Gly Ile Ser Ser Arg Gln Val Val Val Glu
            530                 535                 540

Gly Arg Thr Val Pro Ser Ser Val Ser Gly Val Thr Val Asn Asn Ser
545                 550                 555                 560

Gly Arg Asn Asp Tyr Leu Ser Val Ser Trp Leu Pro Ala Pro Gly Asp
                565                 570                 575

Val Asp Asn Tyr Glu Val Thr Leu Ser His Asp Gly Arg Val Val Gln
                580                 585                 590

Ser Leu Val Ile Ala Lys Ser Val Arg Glu Cys Ser Phe Ser Ser Leu
            595                 600                 605

Thr Pro Gly Arg Leu Tyr Thr Val Thr Ile Thr Thr Arg Ser Gly Lys
610                 615                 620

Tyr Glu Asn His Ser Phe Ser Gln Glu Arg Thr Val Pro Asp Lys Val
625                 630                 635                 640

Gln Gly Val Ser Val Ser Asn Ser Ala Arg Ser Asp Tyr Leu Arg Val
                645                 650                 655

Ser Trp Val His Ala Thr Gly Asp Phe Asp His Tyr Glu Val Thr Ile
                660                 665                 670

Lys Asn Lys Asn Asn Phe Ile Glu Thr Lys Ser Ile Pro Lys Ser Glu
            675                 680                 685

Asn Glu Cys Val Phe Val Gln Leu Val Pro Gly Arg Leu Tyr Ser Val
            690                 695                 700

Thr Val Thr Thr Lys Ser Gly Gln Tyr Glu Ala Ser Glu Gln Gly Asn
705                 710                 715                 720

Gly Arg Thr Gly Gly Gly His His His His His His His
                725                 730                 735

<210> SEQ ID NO 42
<211> LENGTH: 2210
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atggaatgga gctgggtctt tctcttcttc ctgtcagtaa cgactggtgt ccactccgag      60
cggtgcaact ttaccctggc cgagtccaag gcctcctccc actccgtgtc tatccggtgg     120
cggatctggg gctcccctg caacttcaac ctgacctact cctccgatac cctgggcgct     180
gcctcctgtc ctcctttccg gctggacaac accacctacg ctgcaacct gcaggatctg     240
caggccggca ccatctacaa cttccggatc gtgtccctgg acggcgagga acggacagtg     300
gtgctgcaga ccgatcctct gccccctgcc agattcggcg tgtccaaaga aaagaccacc     360
tccacctccc tgcacgtgtg gtgacccct agccctggca aagtgacctc ctacgaggtg     420
cagctgttcg acgagaacaa ccagaaaatc cagggcgtgc agatccagga atccacctcc     480
tggaacaagt acaccttctt caatctgacc gccggctcca gtacaacat caccatcacc     540
gccgtgtccg cggcaagag atcctcctcc gtgtacacca cggctccac cgtgcccagc     600
cccgtgaagg acatcggcat ctccaccaag gccaactccc tgctggtgtc ctggtcccac     660
ggctccggca acgtggaacg gtacagactg atgctgatgg acaagggcat cctggtgcac     720
ggcagcgtgg tggatagaca ggccacctcc tacaccttca acggcctgac ccccggctac     780
ctgtataacc tgaccgtcgt gaccgaggcc gctggactgc agaactacaa gtggaagctc     840
gtgcggaccg cccccatgga agtgtccaac ctgaaagtga ccaacgacgg ctccctgacc     900
tctctgaaag tgaagtggca gaggcccct ggcaatgtgg acagctacaa tatcaccctg     960
tcccacaagg gcaccatcaa gaatcccgg gtgctggccc ccagagtgac cgagacacac    1020
ttcaaagagc tgaccctgg ccggctgtac caagtgaccg tgtcctgtgt gtctggcgag    1080
ctgtctgccc agagaatggc cgtgggcaga accttccctc tgcccgtgct gcagctgaga    1140
gtgaagcacg ccaacgagac atccctgtcc atcatctggc agccccctgt ggccgagtgg    1200
gaagagtaca tcatcagcct ggccgaccgg gacctgcggc tgatccacaa gtccctgagc    1260
aaggacgcca aagagttcac cttcaccgac ctggtgcctg gccggaagta catggccacc    1320
gtgacctcca tctccggcga cctgaagaac tcctccagcg tgaagggcag gaccgtgcct    1380
gcccaagtga cagacctgca tgtggccaac cagggcatga cctccagcct gttcaccaac    1440
tggacccagg ctcagggcga cgtggaattc taccaggtgc tgctgatcca tgagaacgtc    1500
gtgatcaaga acgagtccat cccctccgag acaagcggct acaactttca cttcctgaag    1560
tccggcagcc tgtactccgt ggtcgtgacc acagtgtccg ggggcatctc ctctagaagg    1620
tggtggtgga aggccgcacc gtgcctagtt cagtgtcagg cgtgaccgtg aacaacagcg    1680
gccgaacga ctacctgtcc gtgtcttggc tgcctgcccc tggggacgtg gacaactacg    1740
aagtgaccct gtctcacgac ggccgggtgg tgcagtctct cgtgatcgct aagtccgtgc    1800
gcgagtgctc cttcagcagc ctgacacctg gcagactgta accgtgacc atcaccacca    1860
gatccgggaa gtacgagaac acagcttct cccaggaacg aaccgtgccc acaaggtgc     1920
agggcgtgtc agtgtctaac tccgccagat ctgactacct gagagtgtcc tgggtgcacg    1980
ccaccggcga cttcgaccat tatgaagtga caatcaagaa caagaacaac ttcatcgaga    2040
caaagagcat ccccaagtcc gagaacgagt gcgtgttcgt gcagctggtg ccaggcaggc    2100
tgtattctgt gacagtgacc accaagtccg gccagtacga ggcctctgag cagggcaatg    2160
```
gcagaaccgg cggtggacac caccatcatc accatcacca ccatcactag            2210

<210> SEQ ID NO 43
<211> LENGTH: 971
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Met Glu Trp Ser Trp Val Phe Leu Phe Phe Leu Ser Val Thr Thr Gly
1               5                   10                  15

Val His Ser Ala Gly Gly Thr Pro Ser Pro Ile Pro Asp Pro Ser Val
            20                  25                  30

Ala Thr Val Ala Thr Gly Glu Asn Gly Ile Thr Gln Ile Ser Ser Thr
        35                  40                  45

Ala Glu Ser Phe His Lys Gln Asn Gly Thr Gly Thr Pro Gln Val Glu
    50                  55                  60

Thr Asn Thr Ser Glu Asp Gly Glu Ser Ser Gly Ala Asn Asp Ser Leu
65                  70                  75                  80

Arg Thr Pro Glu Gln Gly Ser Asn Gly Thr Asp Gly Ala Ser Gln Lys
                85                  90                  95

Thr Pro Ser Ser Thr Gly Pro Ser Pro Val Phe Asp Ile Lys Ala Val
            100                 105                 110

Ser Ile Ser Pro Thr Asn Val Ile Leu Thr Trp Lys Ser Asn Asp Thr
        115                 120                 125

Ala Ala Ser Glu Tyr Lys Tyr Val Val Lys His Lys Met Glu Asn Glu
    130                 135                 140

Lys Thr Ile Thr Val Val His Gln Pro Trp Cys Asn Ile Thr Gly Leu
145                 150                 155                 160

Arg Pro Ala Thr Ser Tyr Val Phe Ser Ile Thr Pro Gly Ile Gly Asn
                165                 170                 175

Glu Thr Trp Gly Asp Pro Arg Val Ile Lys Val Ile Thr Glu Pro Ile
            180                 185                 190

Pro Val Ser Asp Leu Arg Val Ala Leu Thr Gly Val Arg Lys Ala Ala
        195                 200                 205

Leu Ser Trp Ser Asn Gly Asn Gly Thr Ala Ser Cys Arg Val Leu Leu
    210                 215                 220

Glu Ser Ile Gly Ser His Glu Glu Leu Thr Gln Asp Ser Arg Leu Gln
225                 230                 235                 240

Val Asn Ile Ser Gly Leu Lys Pro Gly Val Gln Tyr Asn Ile Asn Pro
                245                 250                 255

Tyr Leu Leu Gln Ser Asn Lys Thr Lys Gly Asp Pro Leu Gly Thr Glu
            260                 265                 270

Gly Gly Leu Asp Ala Ser Asn Thr Glu Arg Ser Arg Ala Gly Ser Pro
        275                 280                 285

Thr Ala Pro Val His Asp Glu Ser Leu Val Gly Pro Val Asp Pro Ser
    290                 295                 300

Ser Gly Gln Gln Ser Arg Asp Thr Glu Val Leu Leu Val Gly Leu Glu
305                 310                 315                 320

Pro Gly Thr Arg Tyr Asn Ala Thr Val Tyr Ser Gln Ala Ala Asn Gly
                325                 330                 335

Thr Glu Gly Gln Pro Gln Ala Ile Glu Phe Arg Thr Asn Ala Ile Gln
            340                 345                 350
```

```
Val Phe Asp Val Thr Ala Val Asn Ile Ser Ala Thr Ser Leu Thr Leu
            355                 360                 365

Ile Trp Lys Val Ser Asp Asn Glu Ser Ser Asn Tyr Thr Tyr Lys
    370                 375                 380

Ile His Val Ala Gly Glu Thr Asp Ser Ser Asn Leu Asn Val Ser Glu
385                 390                 395                 400

Pro Arg Ala Val Ile Pro Gly Leu Arg Ser Ser Thr Phe Tyr Asn Ile
                405                 410                 415

Thr Val Cys Pro Val Leu Gly Asp Ile Glu Gly Thr Pro Gly Phe Leu
            420                 425                 430

Gln Val His Thr Pro Pro Val Pro Val Ser Asp Phe Arg Val Thr Val
            435                 440                 445

Val Ser Thr Thr Glu Ile Gly Leu Ala Trp Ser Ser His Asp Ala Glu
        450                 455                 460

Ser Phe Gln Met His Ile Thr Gln Glu Gly Ala Gly Asn Ser Arg Val
465                 470                 475                 480

Glu Ile Thr Thr Asn Gln Ser Ile Ile Gly Gly Leu Phe Pro Gly
                485                 490                 495

Thr Lys Tyr Cys Phe Glu Ile Val Pro Lys Gly Pro Asn Gly Thr Glu
            500                 505                 510

Gly Ala Ser Arg Thr Val Cys Asn Arg Thr Val Pro Ser Ala Val Phe
            515                 520                 525

Asp Ile His Val Val Tyr Val Thr Thr Thr Glu Met Trp Leu Asp Trp
            530                 535                 540

Lys Ser Pro Asp Gly Ala Ser Glu Tyr Val Tyr His Leu Val Ile Glu
545                 550                 555                 560

Ser Lys His Gly Ser Asn His Thr Ser Thr Tyr Asp Lys Ala Ile Thr
                565                 570                 575

Leu Gln Gly Leu Ile Pro Gly Thr Leu Tyr Asn Ile Thr Ile Ser Pro
            580                 585                 590

Glu Val Asp His Val Trp Gly Asp Pro Asn Ser Thr Ala Gln Tyr Thr
            595                 600                 605

Arg Pro Ser Asn Val Ser Asn Ile Asp Val Ser Thr Asn Thr Thr Ala
            610                 615                 620

Ala Thr Leu Ser Trp Gln Asn Phe Asp Asp Ala Ser Pro Thr Tyr Ser
625                 630                 635                 640

Tyr Cys Leu Leu Ile Glu Lys Ala Gly Asn Ser Ser Asn Ala Thr Gln
                645                 650                 655

Val Val Thr Asp Ile Gly Ile Thr Asp Ala Thr Val Thr Glu Leu Ile
            660                 665                 670

Pro Gly Ser Ser Tyr Thr Val Glu Ile Phe Ala Gln Val Gly Asp Gly
            675                 680                 685

Ile Lys Ser Leu Glu Pro Gly Arg Lys Ser Phe Cys Thr Asp Pro Ala
    690                 695                 700

Ser Met Ala Ser Phe Asp Cys Glu Val Val Pro Lys Glu Pro Ala Leu
705                 710                 715                 720

Val Leu Lys Trp Thr Cys Pro Pro Gly Ala Asn Ala Gly Phe Glu Leu
                725                 730                 735

Glu Val Ser Ser Gly Ala Trp Asn Asn Ala Thr His Leu Glu Ser Cys
            740                 745                 750

Ser Ser Glu Asn Gly Thr Glu Tyr Arg Thr Glu Val Thr Tyr Leu Asn
            755                 760                 765
```

| | | | | | | | | | | | | | | |
|---|---|---|---|---|---|---|---|---|---|---|---|---|---|---|
|Phe|Ser|Thr|Ser|Tyr|Asn|Ile|Ser|Ile|Thr|Thr|Val|Ser|Cys|Gly|Lys|
| |770| | | |775| | | |780| | | | | | |

Phe Ser Thr Ser Tyr Asn Ile Ser Ile Thr Thr Val Ser Cys Gly Lys
    770                  775              780

Met Ala Ala Pro Thr Arg Asn Thr Cys Thr Thr Gly Ile Thr Asp Pro
785                790              795              800

Pro Pro Pro Asp Gly Ser Pro Asn Ile Thr Ser Val Ser His Asn Ser
        805                810              815

Val Lys Val Lys Phe Ser Gly Phe Glu Ala Ser His Gly Pro Ile Lys
        820                825              830

Ala Tyr Ala Val Ile Leu Thr Thr Gly Glu Ala Gly His Pro Ser Ala
        835                840              845

Asp Val Leu Lys Tyr Thr Tyr Glu Asp Phe Lys Lys Gly Ala Ser Asp
850                855              860

Thr Tyr Val Thr Tyr Leu Ile Arg Thr Glu Glu Lys Gly Arg Ser Gln
865                870              875              880

Ser Leu Ser Glu Val Leu Lys Tyr Glu Ile Asp Val Gly Asn Glu Ser
        885                890              895

Thr Thr Leu Gly Tyr Tyr Asn Gly Lys Leu Glu Pro Leu Gly Ser Tyr
            900              905              910

Arg Ala Cys Val Ala Gly Phe Thr Asn Ile Thr Phe His Pro Gln Asn
        915                920              925

Lys Gly Leu Ile Asp Gly Ala Glu Ser Tyr Val Ser Phe Ser Arg Tyr
            930              935              940

Ser Asp Ala Val Ser Leu Pro Gln Asp Pro Gly Val Ile Cys Gly Gly
945                950              955              960

Gly His His His His His His His His His
            965              970

<210> SEQ ID NO 44
<211> LENGTH: 2916
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 44

```
atggaatgga gctgggtctt tctcttcttc ctgtcagtaa cgactggtgt ccactccgca      60
ggtggcaccc ctagtccaat tcctgaccct tcagtagcaa ctgttgccac agggaaaat     120
ggcataacgc agatcagcag tacagcagaa ccttttcata acagaatgg aactggaaca     180
cctcaggtgg aaacaaacac cagtgaggat ggtgaaagct ctggagccaa cgatagttta     240
agaacacctg aacaaggatc taatgggact gatggggcat ctcaaaaaac tcccagtagc     300
actgggccca gtcctgtgtt tgacattaaa gctgtttcca tcagtccaac caatgtgatc     360
ttaacttgga aagtaatga cacagctgct tctgagtaca gtatgtagt aaagcataag     420
atggaaaatg agaagacaat tactgttgtg catcaaccat ggtgtaacat cacaggctta     480
cgtccagcga cttcatatgt attctccatc actccaggaa taggcaatga acttgggga     540
gatcccagag tcataaaagt catcacagag ccgatcccag tttctgatct ccgtgttgcc     600
ctcacgggtg tgaggaaggc tgctctctcc tggagcaatg caatggcac tgcctcctgc     660
cgggttcttc ttgaaagcat tggaagccat gaggagttga ctcaagactc aagacttcag     720
gtcaatatct cggcctgaa gccaggggtt caatacaaca tcaacccgta tcttctacaa     780
tcaaataaga caagggaga ccccttgggc acagaaggtg cttggatgc cagcaataca     840
gagagaagcc gggcagggag ccccaccgcc cctgtgcatg atgagtccct cgtgggacct     900
```

```
gtggacccat cctccggcca gcagtcccga gacacggaag tcctgcttgt cgggttagag    960
cctggcaccc gatacaatgc caccgtttat tcccaagcag cgaatggcac agaaggacag   1020
ccccaggcca tagagttcag gacaaatgct attcaggttt ttgacgtcac cgctgtgaac   1080
atcagtgcca caagcctgac cctgatctgg aaagtcagcg ataacgagtc gtcatctaac   1140
tatacctaca agatacatgt ggcggggggag acagattctt ccaatctcaa cgtcagtgag   1200
cctcgcgctg tcatccccgg actccgctcc agcaccttct acaacatcac agtgtgtcct   1260
gtcctaggtg acatcgaggg cacgccgggc ttcctccaag tgcacacccc ccctgttcca   1320
gtttctgact ccgagtgac agtggtcagc acgacggaga tcggcttagc atggagcagc   1380
catgatgcag aatcatttca gatgcatatc acacaggagg gagctggcaa ttctcgggta   1440
gaaataacca ccaaccaaag tattatcatt ggtggcttgt tccctggaac caagtattgc   1500
tttgaaatag ttccaaaagg accaaatggg actgaagggg catctcggac agtttgcaat   1560
agaactgttc ccagtgcagt gtttgacatc acgtggtct acgtcaccac cacgagatg   1620 tggctggact ggaagagccc tgacggtgct tccgagtatg tctaccattt agtcatagag   1680
tccaagcatg gctctaacca cacaagcacg tatgacaaag cgattactct ccagggcctg   1740
attccgggca ccttatataa catcaccatc tctccagaag tggaccacgt ctgggggggac   1800 cccaactcca ctgcacagta cacacggccc agcaatgtgt ccaacattga tgtaagtacc   1860
aacaccacag cagcaacttt aagttggcag aactttgatg acgcctctcc cacgtactcc   1920
tactgccttc ttattgagaa ggctggaaat tccagcaacg caacacaagt agtcacggac   1980
attggaatta ctgacgctac agtcactgaa ttaatacctg gctcatcata cacagtggag   2040
atctttgcac aagtagggga tgggatcaag tcactggaac ctggccggaa gtcattctgt   2100
acagatcctg cgtccatggc ctccttcgac tgcgaagtgg tccccaaaga gccagccctg   2160
gttctcaaat ggacctgccc tcctggcgcc aatgcaggct ttgagctgga ggtcagcagt   2220
ggagcctgga acaatgcgac ccacctggag agctgctcct ctgagaatgg cactgagtat   2280
agaacggaag tcacgtattt gaattttct acctcgtaca acatcagcat caccactgtg   2340
tcctgtggaa agatggcagc ccccacccgg aacacctgca ctactggcat cacagatccc   2400
cctcctccag atggatcccc taatattaca tctgtcagtc acaattcagt aaaggtcaag   2460
ttcagtggat ttgaagccag ccacggaccc atcaaagcct atgctgtcat tctcaccacc   2520
ggggaagctg gtcacccttc tgcagatgtc ctgaaataca cgtatgagga tttcaaaaag   2580
ggagcctcag atacttatgt gacataccatc ataagaacag aagaaaaggg acgttctcag   2640
agcttgtctg aagttttgaa atatgaaatt gacgttggga atgagtcaac cacacttggt   2700
tattacaatg ggaagctgga acctctgggc tcctaccggg cttgtgtggc tggcttcacc   2760
aacattacct tccaccctca aaacaagggg ctcattgatg gggctgagag ctatgtgtcc   2820
ttcagtcgct actcagatgc tgtttccttg ccccaggatc caggtgtcat ctgtggcggt   2880
ggacaccacc atcatcacca tcaccaccat cactag                             2916
```

<210> SEQ ID NO 45
<211> LENGTH: 1621
<212> TYPE: PRT
<213> ORGANISM: Homo sapiens

<400> SEQUENCE: 45

```
Met Leu Ser His Gly Ala Gly Leu Ala Leu Trp Ile Thr Leu Ser Leu
1               5                  10                  15
```

```
Leu Gln Thr Gly Leu Ala Glu Pro Glu Arg Cys Asn Phe Thr Leu Ala
        20                  25                  30

Glu Ser Lys Ala Ser Ser His Ser Val Ser Ile Gln Trp Arg Ile Leu
    35                  40                  45

Gly Ser Pro Cys Asn Phe Ser Leu Ile Tyr Ser Ser Asp Thr Leu Gly
50                  55                  60

Ala Ala Leu Cys Pro Thr Phe Arg Ile Asp Asn Thr Thr Tyr Gly Cys
65                  70                  75                  80

Asn Leu Gln Asp Leu Gln Ala Gly Thr Ile Tyr Asn Phe Arg Ile Ile
                85                  90                  95

Ser Leu Asp Glu Glu Arg Thr Val Val Leu Gln Thr Asp Pro Leu Pro
            100                 105                 110

Pro Ala Arg Phe Gly Val Ser Lys Glu Lys Thr Thr Ser Thr Ser Leu
        115                 120                 125

His Val Trp Trp Thr Pro Ser Ser Gly Lys Val Thr Ser Tyr Glu Val
    130                 135                 140

Gln Leu Phe Asp Glu Asn Asn Gln Lys Ile Gln Gly Val Gln Ile Gln
145                 150                 155                 160

Glu Ser Thr Ser Trp Asn Glu Tyr Thr Phe Phe Asn Leu Thr Ala Gly
                165                 170                 175

Ser Lys Tyr Asn Ile Ala Ile Thr Ala Val Ser Gly Gly Lys Arg Ser
            180                 185                 190

Phe Ser Val Tyr Thr Asn Gly Ser Thr Val Pro Ser Pro Val Lys Asp
        195                 200                 205

Ile Gly Ile Ser Thr Lys Ala Asn Ser Leu Leu Ile Ser Trp Ser His
    210                 215                 220

Gly Ser Gly Asn Val Glu Arg Tyr Arg Leu Met Leu Met Asp Lys Gly
225                 230                 235                 240

Ile Leu Val His Gly Gly Val Val Asp Lys His Ala Thr Ser Tyr Ala
                245                 250                 255

Phe His Gly Leu Thr Pro Gly Tyr Leu Tyr Asn Leu Thr Val Met Thr
            260                 265                 270

Glu Ala Ala Gly Leu Gln Asn Tyr Arg Trp Lys Leu Val Arg Thr Ala
        275                 280                 285

Pro Met Glu Val Ser Asn Leu Lys Val Thr Asn Asp Gly Ser Leu Thr
    290                 295                 300

Ser Leu Lys Val Lys Trp Gln Arg Pro Pro Gly Asn Val Asp Ser Tyr
305                 310                 315                 320

Asn Ile Thr Leu Ser His Lys Gly Thr Ile Lys Glu Ser Arg Val Leu
                325                 330                 335

Ala Pro Trp Ile Thr Glu Thr His Phe Lys Glu Leu Val Pro Gly Arg
            340                 345                 350

Leu Tyr Gln Val Thr Val Ser Cys Val Ser Gly Glu Leu Ser Ala Gln
        355                 360                 365

Lys Met Ala Val Gly Arg Thr Phe Pro Asp Lys Val Ala Asn Leu Glu
    370                 375                 380

Ala Asn Asn Asn Gly Arg Met Arg Ser Leu Val Val Ser Trp Ser Pro
385                 390                 395                 400

Pro Ala Gly Asp Trp Glu Gln Tyr Arg Ile Leu Leu Phe Asn Asp Ser
                405                 410                 415

Val Val Leu Leu Asn Ile Thr Val Gly Lys Glu Glu Thr Gln Tyr Val
            420                 425                 430
```

```
Met Asp Asp Thr Gly Leu Val Pro Gly Arg Gln Tyr Glu Val
            435                 440                 445
Ile Val Glu Ser Gly Asn Leu Lys Asn Ser Glu Arg Cys Gln Gly Arg
    450                 455                 460
Thr Val Pro Leu Ala Val Leu Gln Leu Arg Val Lys His Ala Asn Glu
465                 470                 475                 480
Thr Ser Leu Ser Ile Met Trp Gln Thr Pro Val Ala Glu Trp Glu Lys
                485                 490                 495
Tyr Ile Ile Ser Leu Ala Asp Arg Asp Leu Leu Ile His Lys Ser
                500                 505             510
Leu Ser Lys Asp Ala Lys Glu Phe Thr Phe Thr Asp Leu Val Pro Gly
            515                 520                 525
Arg Lys Tyr Met Ala Thr Val Thr Ser Ile Ser Gly Asp Leu Lys Asn
    530                 535                 540
Ser Ser Ser Val Lys Gly Arg Thr Val Pro Ala Gln Val Thr Asp Leu
545                 550                 555                 560
His Val Ala Asn Gln Gly Met Thr Ser Ser Leu Phe Thr Asn Trp Thr
                565                 570                 575
Gln Ala Gln Gly Asp Val Glu Phe Tyr Gln Val Leu Leu Ile His Glu
            580                 585                 590
Asn Val Val Ile Lys Asn Glu Ser Ile Ser Ser Glu Thr Ser Arg Tyr
    595                 600                 605
Ser Phe His Ser Leu Lys Ser Gly Ser Leu Tyr Ser Val Val Val Thr
                610                 615                 620
Thr Val Ser Gly Gly Ile Ser Ser Arg Gln Val Val Glu Gly Arg
625                 630                 635                 640
Thr Val Pro Ser Val Ser Gly Val Thr Val Asn Asn Ser Gly Arg
                645                 650                 655
Asn Asp Tyr Leu Ser Val Ser Trp Leu Leu Ala Pro Gly Asp Val Asp
            660                 665                 670
Asn Tyr Glu Val Thr Leu Ser His Asp Gly Lys Val Val Gln Ser Leu
    675                 680                 685
Val Ile Ala Lys Ser Val Arg Glu Cys Ser Phe Ser Ser Leu Thr Pro
690                 695                 700
Gly Arg Leu Tyr Thr Val Thr Ile Thr Thr Arg Ser Gly Lys Tyr Glu
705                 710                 715                 720
Asn His Ser Phe Ser Gln Glu Arg Thr Val Pro Asp Lys Val Gln Gly
                725                 730                 735
Val Ser Val Ser Asn Ser Ala Arg Ser Asp Tyr Leu Arg Val Ser Trp
            740                 745                 750
Val His Ala Thr Gly Asp Phe Asp His Tyr Glu Val Thr Ile Lys Asn
    755                 760                 765
Lys Asn Asn Phe Ile Gln Thr Lys Ser Ile Pro Lys Ser Glu Asn Glu
770                 775                 780
Cys Val Phe Val Gln Leu Val Pro Gly Arg Leu Tyr Ser Val Thr Val
785                 790                 795                 800
Thr Thr Lys Ser Gly Gln Tyr Glu Ala Asn Glu Gln Gly Asn Gly Arg
                805                 810                 815
Thr Ile Pro Glu Pro Val Lys Asp Leu Thr Leu Arg Asn Arg Ser Thr
            820                 825                 830
Glu Asp Leu His Val Thr Trp Ser Gly Ala Asn Gly Asp Val Asp Gln
    835                 840                 845
Tyr Glu Ile Gln Leu Leu Phe Asn Asp Met Lys Val Phe Pro Pro Phe
```

```
                850             855             860
His Leu Val Asn Thr Ala Thr Glu Tyr Arg Phe Thr Ser Leu Thr Pro
865                 870                 875                 880

Gly Arg Gln Tyr Lys Ile Leu Val Leu Thr Ile Ser Gly Asp Val Gln
                885                 890                 895

Gln Ser Ala Phe Ile Glu Gly Phe Thr Val Pro Ser Ala Val Lys Asn
            900                 905                 910

Ile His Ile Ser Pro Asn Gly Ala Thr Asp Ser Leu Thr Val Asn Trp
        915                 920                 925

Thr Pro Gly Gly Gly Asp Val Asp Ser Tyr Thr Val Ser Ala Phe Arg
    930                 935                 940

His Ser Gln Lys Val Asp Ser Gln Thr Ile Pro Lys His Val Phe Glu
945                 950                 955                 960

His Thr Phe His Arg Leu Glu Ala Gly Glu Gln Tyr Gln Ile Met Ile
                965                 970                 975

Ala Ser Val Ser Gly Ser Leu Lys Asn Gln Ile Asn Val Val Gly Arg
                980                 985                 990

Thr Val Pro Ala Ser Val Gln Gly  Val Ile Ala Asp Asn  Ala Tyr Ser
            995                 1000                1005

Ser Tyr  Ser Leu Ile Val Ser  Trp Gln Lys Ala Ala  Gly Val Ala
    1010                1015                1020

Glu Arg  Tyr Asp Ile Leu Leu  Leu Thr Glu Asn Gly  Ile Leu Leu
    1025                1030                1035

Arg Asn  Thr Ser Glu Pro Ala  Thr Thr Lys Gln His  Lys Phe Glu
    1040                1045                1050

Asp Leu  Thr Pro Gly Lys Lys  Tyr Lys Ile Gln Ile  Leu Thr Val
    1055                1060                1065

Ser Gly  Gly Leu Phe Ser Lys  Glu Ala Gln Thr Glu  Gly Arg Thr
    1070                1075                1080

Val Pro  Ala Ala Val Thr Asp  Leu Arg Ile Thr Glu  Asn Ser Thr
    1085                1090                1095

Arg His  Leu Ser Phe Arg Trp  Thr Ala Ser Glu Gly  Glu Leu Ser
    1100                1105                1110

Trp Tyr  Asn Ile Phe Leu Tyr  Asn Pro Asp Gly Asn  Leu Gln Glu
    1115                1120                1125

Arg Ala  Gln Val Asp Pro Leu  Val Gln Ser Phe Ser  Phe Gln Asn
    1130                1135                1140

Leu Leu  Gln Gly Arg Met Tyr  Lys Met Val Ile Val  Thr His Ser
    1145                1150                1155

Gly Glu  Leu Ser Asn Glu Ser  Phe Ile Phe Gly Arg  Thr Val Pro
    1160                1165                1170

Ala Ser  Val Ser His Leu Arg  Gly Ser Asn Arg Asn  Thr Thr Asp
    1175                1180                1185

Ser Leu  Trp Phe Asn Trp Ser  Pro Ala Ser Gly Asp  Phe Asp Phe
    1190                1195                1200

Tyr Glu  Leu Ile Leu Tyr Asn  Pro Asn Gly Thr Lys  Lys Glu Asn
    1205                1210                1215

Trp Lys  Asp Lys Asp Leu Thr  Glu Trp Arg Phe Gln  Gly Leu Val
    1220                1225                1230

Pro Gly  Arg Lys Tyr Val Leu  Trp Val Val Thr His  Ser Gly Asp
    1235                1240                1245

Leu Ser  Asn Lys Val Thr Ala  Glu Ser Arg Thr Ala  Pro Ser Pro
    1250                1255                1260
```

```
Pro Ser Leu Met Ser Phe Ala Asp Ile Ala Asn Thr Ser Leu Ala
    1265            1270            1275

Ile Thr Trp Lys Gly Pro Asp Trp Thr Asp Tyr Asn Asp Phe
    1280            1285            1290

Glu Leu Gln Trp Leu Pro Arg Asp Ala Leu Thr Val Phe Asn Pro
    1295            1300            1305

Tyr Asn Asn Arg Lys Ser Glu Gly Arg Ile Val Tyr Gly Leu Arg
    1310            1315            1320

Pro Gly Arg Ser Tyr Gln Phe Asn Val Lys Thr Val Ser Gly Asp
    1325            1330            1335

Ser Trp Lys Thr Tyr Ser Lys Pro Ile Phe Gly Ser Val Arg Thr
    1340            1345            1350

Lys Pro Asp Lys Ile Gln Asn Leu His Cys Arg Pro Gln Asn Ser
    1355            1360            1365

Thr Ala Ile Ala Cys Ser Trp Ile Pro Pro Asp Ser Asp Phe Asp
    1370            1375            1380

Gly Tyr Ser Ile Glu Cys Arg Lys Met Asp Thr Gln Glu Val Glu
    1385            1390            1395

Phe Ser Arg Lys Leu Glu Lys Glu Lys Ser Leu Leu Asn Ile Met
    1400            1405            1410

Met Leu Val Pro His Lys Arg Tyr Leu Val Ser Ile Lys Val Gln
    1415            1420            1425

Ser Ala Gly Met Thr Ser Glu Val Val Glu Asp Ser Thr Ile Thr
    1430            1435            1440

Met Ile Asp Arg Pro Pro Pro Pro Pro His Ile Arg Val Asn
    1445            1450            1455

Glu Lys Asp Val Leu Ile Ser Lys Ser Ser Ile Asn Phe Thr Val
    1460            1465            1470

Asn Cys Ser Trp Phe Ser Asp Thr Asn Gly Ala Val Lys Tyr Phe
    1475            1480            1485

Thr Val Val Val Arg Glu Ala Asp Gly Ser Asp Glu Leu Lys Pro
    1490            1495            1500

Glu Gln Gln His Pro Leu Pro Ser Tyr Leu Glu Tyr Arg His Asn
    1505            1510            1515

Ala Ser Ile Arg Val Tyr Gln Thr Asn Tyr Phe Ala Ser Lys Cys
    1520            1525            1530

Ala Glu Asn Pro Asn Ser Asn Ser Lys Ser Phe Asn Ile Lys Leu
    1535            1540            1545

Gly Ala Glu Met Glu Ser Leu Gly Gly Lys Cys Asp Pro Thr Gln
    1550            1555            1560

Gln Lys Phe Cys Asp Gly Pro Leu Lys Pro His Thr Ala Tyr Arg
    1565            1570            1575

Ile Ser Ile Arg Ala Phe Thr Gln Leu Phe Asp Glu Asp Leu Lys
    1580            1585            1590

Glu Phe Thr Lys Pro Leu Tyr Ser Asp Thr Phe Phe Ser Leu Pro
    1595            1600            1605

Ile Thr Thr Glu Ser Glu Pro Leu Phe Gly Ala Ile Glu
    1610            1615            1620

<210> SEQ ID NO 46
<211> LENGTH: 89
<212> TYPE: PRT
<213> ORGANISM: Homo sapiens
```

<400> SEQUENCE: 46

Leu Ala Glu Pro Glu Arg Cys Asn Phe Thr Leu Ala Glu Ser Lys Ala
1               5                   10                  15

Ser Ser His Ser Val Ser Ile Gln Trp Arg Ile Leu Gly Ser Pro Cys
            20                  25                  30

Asn Phe Ser Leu Ile Tyr Ser Ser Asp Thr Leu Gly Ala Ala Leu Cys
        35                  40                  45

Pro Thr Phe Arg Ile Asp Asn Thr Thr Tyr Gly Cys Asn Leu Gln Asp
    50                  55                  60

Leu Gln Ala Gly Thr Ile Tyr Asn Phe Arg Ile Ile Ser Leu Asp Glu
65                  70                  75                  80

Glu Arg Thr Val Val Leu Gln Thr Asp
                85

<210> SEQ ID NO 47
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Thr Gly Gly Gly Leu Val Gln Pro Lys Gly
1               5                   10                  15

Ser Met Lys Leu Ser Cys Ala Ala Ser Gly Phe Thr Phe Asn Ala Asn
            20                  25                  30

Ala Met Asn Trp Ile Arg Gln Ala Pro Gly Lys Gly Leu Glu Trp Val
        35                  40                  45

Ala Arg Ile Arg Thr Lys Ser Asn Asn Tyr Ala Thr Tyr Tyr Ala Gly
    50                  55                  60

Ser Val Lys Asp Arg Phe Thr Ile Ser Arg Asp Asp Ala Gln Asn Met
65                  70                  75                  80

Leu Tyr Leu Gln Met Asn Asp Leu Lys Thr Glu Asp Thr Ala Met Tyr
                85                  90                  95

Tyr Cys Val Arg Asp Tyr Gly Ser Ser Ala Trp Ile Thr Tyr Trp
            100                 105                 110

Gly Gln Gly Thr Leu Val Thr Val Ser Ala
        115                 120

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Val Met Thr Gln Ser His Lys Phe Met Ser Thr Ser Val Gly
1               5                   10                  15

Asp Arg Val Ser Ile Thr Cys Lys Ala Ser Gln His Val Gly Thr Ala
            20                  25                  30

Val Ala Trp Tyr Gln Gln Lys Pro Asp Gln Ser Pro Lys Gln Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser

```
                65                  70                  75                  80
Glu Asp Leu Ala Asp Tyr Phe Cys Gln Gln Tyr Ser Ser Tyr Pro Phe
                    85                  90                  95

Thr Phe Gly Ser Gly Thr Lys Leu Glu Ile Lys
            100                 105
```

<210> SEQ ID NO 49

<400> SEQUENCE: 49

000

<210> SEQ ID NO 50
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Glu Val Gln Leu Val Glu Thr Gly Gly Gly Leu Val Gln Pro Lys Gly
1               5                   10                  15

Ser Met Lys Leu Ser Cys Ala Ala Ser Gly Phe Thr Phe Asn Ala Asn
                20                  25                  30

Ala Met Asn Trp Ile Arg Gln Ala Pro Gly Lys Gly Leu Glu Trp Val
            35                  40                  45

Ala Arg Ile Arg Thr Lys Ser Asn Asn Tyr Ala Thr Tyr Tyr Ala Gly
        50                  55                  60

Ser Val Lys Asp Arg Phe Thr Ile Ser Arg Asp Asp Ala Gln Asn Met
65                  70                  75                  80

Leu Tyr Leu Gln Met Asn Asp Leu Lys Thr Glu Asp Thr Ala Met Tyr
                85                  90                  95

Tyr Cys Val Arg Asp Tyr Tyr Gly Ser Ser Ala Trp Ile Thr Tyr Trp
            100                 105                 110

Gly Gln Gly Thr Leu Val Thr Val Ser Ala
        115                 120
```

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Asp Ile Val Met Thr Gln Ser His Lys Phe Met Ser Thr Ser Val Gly
1               5                   10                  15

Asp Arg Val Ser Ile Thr Cys Lys Ala Ser Gln His Val Gly Thr Ala
                20                  25                  30

Val Ala Trp Tyr Gln Gln Lys Pro Asp Gln Ser Pro Lys Gln Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Phe
                85                  90                  95
```

Thr Phe Gly Ser Gly Thr Lys Leu Glu Ile Lys
            100                 105

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 52

His His His His His His
1               5

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 53

His His His His His His His His His His
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Phe Thr Phe Asn Ala Asn Ala Met Asn
1               5                   10

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ile Arg Thr Lys Ser Asn Asn Tyr Ala Thr Tyr Tyr Ala Gly Ser
1               5                   10                  15

Val Lys Asp

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Val Arg Asp Tyr Tyr Gly Ser Ser Ala Trp Ile Thr Tyr
1               5                   10

<210> SEQ ID NO 57
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 57

Lys Ala Ser Gln His Val Gly Thr Ala Val Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Ala Ser Thr Arg His Thr
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Gln Tyr Ser Ser Tyr Pro Phe Thr
1               5
```

HUMANIZED MONOCLONAL ANTIBODIES THAT TARGET VE-PTP (HPTP-BETA)

CROSS REFERENCE

This application is a continuation of U.S. application Ser. No. 16/775,860 filed on Jan. 29, 2020, which is a continuation of U.S. application Ser. No. 16/180,850, filed on Nov. 5, 2018, now U.S. Pat. No. 10,604,569 issued on Mar. 31, 2020, which is a continuation of U.S. application Ser. No. 15/654,289, filed on Jul. 19, 2017, now U.S. Pat. No. 10,253,094, issued on Apr. 9, 2019, which claims the benefit of U.S. Provisional Application No. 62/364,381, filed Jul. 20, 2016, and U.S. Provisional Application No. 62/377,072, filed Aug. 19, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 7, 2020, is named 45725724304_SL.txt and is 131,626 bytes in size.

BACKGROUND OF THE INVENTION

Monoclonal antibodies generated from non-human organisms can elicit an immune response when administered to humans. Segments of these non-human monoclonal antibodies can be replaced with humanized sequences through a humanization process to reduce the likelihood of drug immunogenicity while preserving target specificity.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention provides a compound comprising a sequence that is at least 80% identical to SEQ ID NO: 9, SEQ ID NO: 10, SEQ ID NO: 11, or SEQ ID NO: 12.

In some embodiments, the invention provides a compound comprising a sequence that is at least 80% identical to SEQ ID NO: 20, SEQ ID NO: 21, SEQ ID NO: 22, or SEQ ID NO: 23.

In some embodiments, the invention provides a compound comprising: a) a heavy chain that comprises a sequence that is at least 80% identical to SEQ ID NO: 30; and b) a light chain that comprises a sequence that is at least 80% identical to SEQ ID NO: 34.

In some embodiments, the invention provides a compound comprising: a) a heavy chain that comprises a sequence that is at least 80% identical to SEQ ID NO: 29; and b) a light chain that comprises a sequence that is at least 80% identical to SEQ ID NO: 35.

In some embodiments, the invention provides a compound comprising: a) a heavy chain that comprises a sequence that is at least 80% identical to SEQ ID NO: 30; and b) a light chain that comprises a sequence that is at least 80% identical to SEQ ID NO: 37.

BRIEF DESCRIPTION OF THE FIGURES

FIG. 1 shows a sequence alignment of the murine $V_H$ sequence (truncated $V_{H0}$; SEQ ID NO: 47) with the four humanized variants SEQ ID NO: 9 ($V_{H1}$), SEQ ID NO: 10 ($V_{H2}$), SEQ ID NO: 11 ($V_{H3}$), and SEQ ID NO: 12 ($V_{H4}$).

FIG. 2 shows a sequence alignment of the murine $V_L$, sequence (truncated $V_{L0}$; SEQ ID NO: 48) with the four humanized $V_L$ variants SEQ ID NO: 20 ($V_{L1}$), SEQ ID NO: 21 ($V_{L2}$), SEQ ID NO: 22 ($V_{L3}$), and SEQ ID NO: 23 ($V_{L4}$).

FIG. 13 depicts a reducing (panel A) and a non-reducing (panel B) SDS-PAGE of anti-human VE-PTP (anti-HPTP-β) humanized variants of R15E6.

FIG. 19 illustrates concentration-dependent Tie2 activation (top panel) and Akt activation (bottom panel) in the absence of ligands by HC2LC4 and HC2LC1 as determined by western blot.

DETAILED DESCRIPTION OF THE INVENTION

Figure 3:
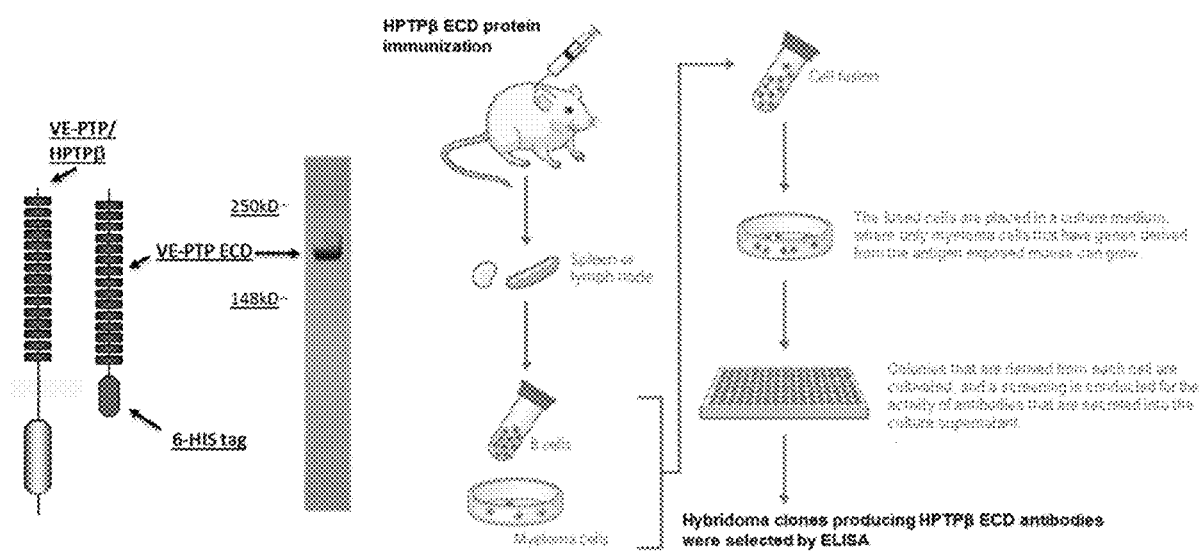
FIG. 3 summarizes the hybridoma technology used to generate monoclonal antibodies against the HPTP-β extracellular domain (human VE-PTP/HPTP-β ECD). The 6-HIS tag disclosed in FIG. 3 is SEQ ID NO: 52.

The present disclosure provides compositions and methods for targeting vascular endothelial protein tyrosine phosphatase (VE-PTP or VEPTP) or human protein tyrosine phosphatase-beta (HPTP-β) for the treatment of ocular disorders that are characterized by, for example, vascular instability, angiogenesis, neovascularization, vascular leakage, and edema. Compositions disclosed herein can activate Tie2 signaling by promoting protein phosphorylation, such as phosphorylation of the Tie2 protein.

VE-PTP is a member of the receptor-like family of the protein tyrosine phosphatases (PTPases). VE-PTP is a transmembrane protein found primarily in vascular endothelial cells that displays structural and functional similarity to cell adhesion molecules. VE-PTP is found in various species including, for example, zebrafish, chicken, dog, mouse, marmoset, monkey, and human. The human orthologue of VE-PTP is HPTP-β.

Tie2 (tyrosine kinase with immunoglobulin and epidermal growth factor homology domains 2) is a membrane receptor tyrosine kinase expressed primarily in vascular endothelial cells throughout development. The principle regulators of Tie2 phosphorylation are angiopoietin 1 (Ang1) and angiopoietin 2 (Ang2). Ang1 is an agonist of Tie2, and binding of Ang1 to Tie2 promotes receptor phosphorylation. Ang2 acts in a context-dependent antagonist or agonist of Tie2. Binding of Ang1 to Tie2 increases the level of endogenous Tie2 receptor phosphorylation and initiates downstream signaling to induce vascular stabilization through highly organized angiogenesis, tightening of the endothelial cell junctions (endothelial cell proximity), enhanced endothelial cell viability, reduced endothelial inflammation and improved endothelial function. During angiogenesis, Ang2 acts as a negative regulator of Ang1-Tie2 signaling.

Under physiological conditions, the duration of Tie2 phosphorylation is regulated by VE-PTP (HPP-β), which removes the phosphate from the Tie2 receptor. By inhibiting VE-PTP (HPP-β), the level of Tie2 phosphorylation substantially increases, restoring vascular stability. A VE-PTP (HPP-β) inhibitor, for example, an antibody that binds VE-PTP (HPP-β), can activate Tie2 downstream signaling by inhibiting VE-PTP (HPP-β). Inhibition of VE-PTP (HPP-β) by the inhibitor can provide vascular stability in subjects with ocular disorders described herein.

A VE-PTP (HPP-β) inhibitor of the disclosure can comprise the murine monoclonal antibody R15E6 produced by hybridoma cell line ATCC No. PTA-7580, which is immunoreactive to the extracellular domain of human VE-PTP (HPP-β) (SEQ ID NO. 45), is immunoreactive to the first FN3 repeat of human VE-PTP (HPP-β) (SEQ ID NO. 46). The VE-PTP (HPP-β) inhibitor can comprise an antibody having the same or substantially the same biological characteristics of R15E6, an antibody fragment of R15E6, wherein the fragment comprises one or both of the heavy and light chain variable regions, a F(ab')2 of R15E6, dimers or trimers of a Fab, Fv, scFv, and dia-, tria-, or tetrabodies derived from R15E6. In some embodiments, a fragment of a compound described herein can be assayed for any biological activity described herein. In some embodiments, a fragment of a compound described herein can activate Tie2, or provide the biological activity of the corresponding intact antibody at an equipotent, increased, or decreased level.

```
Extracellular domain of human VE-PTP (HPTP-β)
(SEQ ID NO: 45):
MLSHGAGLALWITLSLLQTGLAEPERCNFTLAESKASSHSVSIQWRILGS

PCNFSLIYSSDTLGAALCPTFRIDNTTYGCNLQDLQAGTIYNFRIISLDE

ERTVVLQTDPLPPARFGVSKEKTTSTSLHVWWTPSSGKVTSYEVQLFDEN

NQKIQGVQIQESTSWNEYTFFNLTAGSKYNIAITAVSGGKRSFSVYTNGS

TVPSPVKDIGISTKANSLLISWSHGSGNVERYRLMLMDKGILVHGGVVDK

HATSYAFHGLTPGYLYNLTVMTEAAGLQNYRWKLVRTAPMEVSNLKVTND

GSLTSLKVKWQRPPGNVDSYNITLSHKGTIKESRVLAPWITETHFKELVP

GRLYQVTVSCVSGELSAQKMAVGRTFPDKVANLEANNNGRMRSLVVSWSP

PAGDWEQYRILLFNDSVVLLNITVGKEETQYVMDDTGLVPGRQYEVEVIV

ESGNLKNSERCQGRTVPLAVLQLRVKHANETSLSIMWQTPVAEWEKYIIS

LADRDLLLIHKSLSKDAKEFTFTDLVPGRKYMATVTSISGDLKNSSSVKG

RTVPAQVTDLHVANQGMTSSLFTNWTQAQGDVEFYQVLLIHENVVIKNES

ISSETSRYSFHSLKSGSLYSVVVTTVSGGISSRQVVVEGRTVPSSVSGVT

VNNSGRNDYLSVSWLLAPGDVDNYEVTLSHDGKVVQSLVIAKSVRECSFS

SLTPGRLYTVTITTRSGKYENHSFSQERTVPDKVQGVSVSNSARSDYLRV

SWVHATGDFDHYEVTIKNKNNFIQTKSIPKSENECVFVQLVPGRLYSVTV

TTKSGQYEANEQGNGRTIPEPVKDLTLRNRSTEDLHVTWSGANGDVDQYE

IQLLFNDMKVFPPFHLVNTATEYRFTSLTPGRQYKILVLTISGDVQQSAF

IEGFTVPSAVKNIHISPNGATDSLTVNWTPGGGDVDSYTVSAFRHSQKVD

SQTIPKHVFEHTFHRLEAGEQYQIMIASVSGSLKNQINVVGRTVPASVQG

VIADNAYSSYSLIVSWQKAAGVAERYDILLLTENGILLRNTSEPATTKQH

KFEDLTPGKKYKIQILTVSGGLFSKEAQTEGRTVPAAVTDLRITENSTRH
```

-continued

LSFRWTASEGELSWYNIFLYNPDGNLQERAQVDPLVQSFSFQNLLQGRMY

KMVIVTHSGELSNESFIFGRTVPASVSHLRGSNRNTTDSLWFNWSPASGD

FDFYELILYNPNGTKKENWKDKDLTEWRFQGLVPGRKYVLWVVTHSGDLS

NKVTAESRTAPSPPSLMSFADIANTSLAITWKGPPDWTDYNDFELQWLPR

DALTVFNPYNNRKSEGRIVYGLRPGRSYQFNVKTVSGDSWKTYSKPIFGS

VRTKPDKIQNLHCRPQNSTAIACSWIPPDSDFDGYSIECRKMDTQEVEFS

RKLEKEKSLLNIMMLVPHKRYLVSIKVQSAGMTSEVVEDSTITMIDRPPP

PPPHIRVNEKDVLISKSSINFTVNCSWFSDTNGAVKYFTVVVREADGSDE

LKPEQQHPLPSYLEYRHNASIRVYQTNYFASKCAENPNSNSKSFNIKLGA

EMESLGGKCDPTQQKFCDGPLKPHTAYRISIRAFTQLFDEDLKEFTKPLY

SDTFFSLPITTESEPLFGAIE

First FN3 repeat of human VE-PTP (HPTP-β)
(SEQ ID NO: 46):
LAEPERCNFTLAESKASSHSVSIQWRILGSPCNFSLIYSSDTLGAALCPT

FRIDNTTYGCNLQDLQAGTIYNFRIISLDEERTVVLQTD

A VE-PTP (HPP-β) inhibitor of the disclosure can include an antibody, or an antibody fragment, variant, or derivative thereof, either alone or in combination with other amino acid sequences. The inhibitor can undergo modifications, for example, enzymatic cleavage, and posttranslational modifications.

A VE-PTP (HPP-β) inhibitor of the disclosure can bind a dominant-negative isoform of VE-PTP (HPP-β). In some embodiments, this dominant-negative isoform can correspond to a form of VE-PTP (HPP-β) deficient in phosphatase activity that can compete with endogenous VE-PTP (HPP-β). Functional assessment of dominant-negative VE-PTP (HPP-β) can occur via delivery of the transgene and determination of the effect on Tie2 phosphorylation.

A VE-PTP (HPP-β) inhibitor of the disclosure can comprise a plurality of VE-PTP (HPP-β) binding sites. In some embodiments, a VE-PTP (HPP-β) inhibitor can bind to two VE-PTP (HPP-β) molecules simultaneously, thereby bringing the two VE-PTP (HPP-β) molecules into close proximity. A VE-PTP (HPP-β) inhibitor can bind to three VE-PTP (HPP-β) molecules simultaneously, thereby bringing the three VE-PTP (HPP-β) molecules into close proximity.

A VE-PTP (HPP-β) inhibitor of the disclosure can be covalently or non-covalently conjugated to another moiety or vehicle. A moiety or vehicle can, for example, inhibit degradation, increase half-life, increase absorption, reduce toxicity, reduce immunogenicity, and/or increase biological activity of the inhibitor. Non-limiting examples of the moiety include Fc domains of immunoglobulins, polymers such as polyethylene glycol (PEG), polylysine, and dextran, lipids, cholesterol groups such as steroids, carbohydrates, dendrimers, oligosaccharides, and peptides.

The compounds of the present invention can be used for targeting VE-PTP (HPP-β) to restore Tie2 activity and initiate downstream signaling cascades including, for example, Akt/PI3-K signaling, Rac1 signaling, MAPK/Ras signaling. In some embodiments, compounds of the present invention can inhibit NF-κB signaling. The activation of Tie2 can lead to vascular stabilization, which can be beneficial for the treatment of diabetes-related conditions and ocular conditions including, for example, retinopathy, diabetic retinopathy, retinal perfusion, ocular neovascularization, ocular vascular leak, ocular edema, intraocular pressure, ocular hypertension, ocular inflammation, glaucoma, and ocular hemorrhage. The compounds can also be effective for the treatment of peripheral artery disease including, for example, wound healing, destabilized blood flow, cardiac fibrosis, erectile dysfunction, cardiomyopathy, ischemic injury, cardiac hypertrophy, interstitial fibrosis, nephropathy, albuminuria, glomerulosclerosis, renal fibrosis, neuropathy, and neuronal inflammation.

Antibodies

Antibodies comprise of two identical heavy chain (H) polypeptide sequences and two identical light chain (L) polypeptide sequences. Each of the heavy chains comprises one N-terminal variable ($V_H$) region and three C-terminal constant ($C_H1$, $C_H2$, and $C_H3$) regions. Each of the light chains comprises one N-terminal variable ($V_L$) region and one C-terminal constant ($C_L$) region. The light chain variable region is aligned with the heavy chain variable region and the light chain constant region is aligned with heavy chain constant region $C_H1$. The pairing of a heavy chain variable region and light chain variable region together forms a single antigen-binding site. Each light chain is linked to a heavy chain by one covalent disulfide bond. The two heavy chains are linked to each other by one or more disulfide bonds depending on the heavy chain isotype. Each heavy and light chain also comprises regularly-spaced intrachain disulfide bridges.

The light chain from any vertebrate species can be designated kappa or lambda based on the amino acid sequences of the constant region. Depending on the amino acid sequence of the constant region of the heavy chains, immunoglobulins can be categorized into five classes of immunoglobulins (IgA, IgD, IgE, IgG, and IgM), each having heavy chains designated alpha, delta, epsilon, gamma, and mu, respectively. The alpha and gamma classes are further divided into subclasses on the basis of differences in the sequence and function of the heavy chain constant region. Subclasses of IgA and IgG expressed by humans include IgG1, IgG2, IgG3, IgG4, IgA1 and IgA2.

A variable (V) region comprises segments that can differ extensively in sequence among antibodies. The variable region mediates antigen-binding and defines specificity of a particular antibody for its antigen. However, the variability is not evenly distributed across the span of the variable regions. Instead, the variable regions consist of relatively invariant stretches called framework regions (FR) of 15-30 amino acids separated by shorter regions of extreme variability called hypervariable regions that are each 9-12 amino acids long. The variable regions of native heavy and light chains each comprise four framework regions, largely adopting a β-sheet configuration, connected by three hypervariable regions, which form loops connecting, and in some cases forming a part of, the β-sheet structure. The hypervariable regions in each chain are held together in close proximity by the framework regions and, with the hypervariable regions from the other chain, contribute to the formation of the antigen-binding site of antibodies. The constant domains are not involved directly in binding an antibody to an antigen, but exhibit various effector functions, such as participation of the antibody in antibody dependent cellular cytotoxicity (ADCC).

A hypervariable region can comprise amino acid residues from a complementarity determining region (CDR), for example, around about residues 24-34 (L1), 50-56 (L2), and 89-97 (L3) in the light chain variable region, and around about 1-35 (H1), 50-65 (H2), and 95-102 (H3) in the heavy chain variable region, and/or residues from a hypervariable loop.

A monoclonal antibody can be obtained from a population of substantially homogeneous antibodies, i.e., the individual antibodies comprising the population are identical except for possible naturally occurring mutations that can be present in minor amounts. In contrast to polyclonal antibody preparations, which include different antibodies directed against different epitopes, each monoclonal antibody is directed against a single epitope. In addition to the specificity, the monoclonal antibodies are advantageous in that each can be synthesized uncontaminated by other antibodies.

The monoclonal antibodies used herein can be, for example, chimeric antibodies wherein a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as antigen-binding fragments of such antibodies.

An antibody fragment can comprise a portion of a multimeric antibody, for example, the antigen-binding or variable region of the intact antibody. Non-limiting examples of antibody fragments include Fab, Fab', F(ab')$_2$, dimers, and trimers of Fab conjugates, Fv, scFv, minibodies, dia-, tria-, and tetrabodies, and linear antibodies.

Non-limiting examples of epitopes include amino acids, sugars, lipids, phosphoryl, and sulfonyl groups. An epitope can have specific three-dimensional structural characteristics, and/or specific charge characteristics. Epitopes can be conformational or linear.

Humanized Monoclonal Antibodies

Suitable antibodies that target VE-PTP can be identified using a variety of techniques. For example, candidate agents can be screened for binding to VE-PTP. Agents that bind to VE-PTP can be screened for activity, for example, inhibition of VE-PTP-mediated dephosphorylation of Tie2. In some embodiments, the candidate agents are first screened in vivo for activity.

The selection of a suitable assay for use in identification of a specific inhibitor depends on the nature of the candidate agent to be screened. For example, where the candidates are antibodies or peptibodies, which comprise an Fc moiety, fluorescence-activated cell sorting (FACS) analysis allows the candidate agent to be selected based on the ability to bind to a cell that expresses VE-PTP. The cell can endogenously express VE-PTP or can be genetically engineered to express VE-PTP. For other candidate agents such as aptamers, other techniques can be utilized. For example, aptamers that specifically bind to VE-PTP can be selected using systematic evolution of ligands by exponential enrichment (SELEX), which selects specific aptamers through repeated rounds of in vitro selection.

VE-PTP inhibitors can be screened for VE-PTP-mediated activity, for example, inhibition of Tie2 dephosphorylation. In one suitable assay based on western blotting, human umbilical vein endothelial cells (HUVEC) are cultured in serum free media in the presence or absence of various concentrations of candidate agent, and lysates of the cells are prepared, immunoprecipitated with a Tie2 antibody, resolved by polyacrylamide gel electrophoresis (SDS-PAGE), and transferred to a polyvinylidene difluoride (PVDF) membrane. Membrane-bound immunoprecipitated proteins are then serially western blotted with an anti-phosphotyrosine antibody to quantify Tie2 phosphorylation followed by a Tie2 antibody to quantify total Tie2. Tie2 phosphorylation is expressed as the ratio of the anti-phosphotyrosine signal over the total Tie2 signal. Greater levels of the anti-phosphotyrosine signal indicate greater VE-PTP inhibition by the candidate agent.

Hybridoma technology is a method for producing large numbers of a monoclonal antibody targeting a specific antigen. Hybridoma development begins by injecting a mammalian host, such as a mouse (murine) or rabbit, with an antigen that provokes an immune response. In response to the antigen, B-lymphocytes (B-cells) in the host produce antibodies that bind to the antigen. The B-cells are then harvested from the host and fused with immortal B cell cancer cells (myeloma cells) to produce a hybrid cell line known as a hybridoma. The hybridoma retains both the antibody-producing ability of the B cell and the exaggerated longevity and reproductivity of the myeloma. The hybridomas can be grown in culture starting with one viable hybridoma cell to produce new cultures consisting of genetically identical hybridomas that, in turn, produce one antibody per culture (monoclonal) or mixtures of different antibodies (polyclonal). The myeloma cell line used in this process is selected for the ability to grow in tissue culture and for the inability to synthesize antibodies. After culturing, a primary screening process is performed to identify and select the hybridomas that produce antibodies with highest specificity. Non-limiting examples of antibody screening techniques include ELISA and immunocytochemical screening. The lead hybridomas identified from screening can then be characterized for reactivity, binding affinity, specificity, and cross-reactivity.

In some embodiments, the binding affinity ($K_D$) HPTP-β of a compound of the disclosure is from about 70 pM to about 70 nM, 1 nM to about 70 nM, or at least as strong as about 1 nM. In some embodiments, the binding affinity ($K_D$) to HPTP-β of a compound of the disclosure is from about 4 nM to about 70 nM.

Other recombinant antibody engineering techniques involve the use of viruses or yeast rather than mammals. These techniques rely on rapid cloning of immunoglobulin gene segments to create antibody libraries with slightly different amino acid sequences from which antibodies with desired specificities can be selected. Antibody libraries can be used to enhance specificity to target antigens, stability in various environmental conditions, therapeutic efficacy, and detectability in diagnostic applications.

For human administration, monoclonal antibodies generated from non-human species can be further optimized by a humanization process to reduce the likelihood of immunogenicity while preserving target specificity. Humanization processes involve the incorporation of human DNA to the genetic sequence of the genes that produce the isolated antibodies. The recombinant DNA is then cloned and expressed in cells for large-scale production of the newly humanized antibodies.

An example of a humanized antibody is a modified chimeric antibody. A chimeric antibody is generated as described above. The chimeric antibody is further mutated outside of the CDRs to substitute non-human sequences in the variable regions with the homologous human sequences. Another example of a humanized antibody is a CDR-grafted antibody, in which non-human CDR sequences are introduced into the human heavy and light chain variable sequences of a human antibody scaffold to replace the corresponding human CDR sequences.

A humanized antibody can be produced in mammalian cells, bioreactors, or transgenic animals, such as mice, chicken, sheep, goat, pig, and marmoset. The transgenic animal can have a substantial portion of the human antibody-producing genome inserted into the genome of the animal.

A fully human monoclonal antibody corresponds to an antibody whose antigen-binding residues are fully derived from the human immunoglobulin sequence or fragments thereof undergoing selection. In some embodiments, this selection can occur using phage display techniques in which a series of variable antibody domain is expressed on a filamentous phage coat protein and enriched for binding to a target antigen. In some embodiments, this selection can occur using transgenic animals, for example, mice, rats, or rabbits, in which the entire set of endogenous immunoglobulin genes are replaced with the entire set of human immunoglobulin genes. In some embodiments, the entire set of human immunoglobulin genes can be introduced into the genome of the animal and endogenous antibody production is rendered deficient in the production of antibodies.

Humanized Monoclonal Antibodies that Target VE-PTP (HPTP-β)

The humanization process of a murine monoclonal antibody that targets VE-PTP (HPTP-β) described herein utilizes a combination of CDR-grafting technologies coupled with antibody structure and a database of mature human IgG sequences. Human framework sequences were used as acceptor frameworks for the CDR sequences. These acceptor sequences all originated from mature Human IgG from a human source and not from phage display.

Four humanized variants were designed for the heavy chain and light chain variable domains of a murine monoclonal antibody raised against the recombinant extracellular domain of human VE-PTP (HPTP-β). The designs were based on factors including homology, T-cell epitopes, key residues, and predicted structures.

The sequences disclosed herein were identified using antibody numbering systems from IMGT and Kabat. These two numbering systems identified different residues of the murine antibodies as belonging to the CDR, and a combined IMGT/Kabat CDR sequence was used for optimal retention of CDR-loop conformation.

Heavy Chain Sequences

SEQ ID NO: 1 is the $V_H$ domain of a murine monoclonal antibody R15E6 ($V_{H0}$) that targets human VE-PTP (HPP-β), which includes the murine signal peptide sequence (underlined). SEQ ID NO: 47 is a truncated sequence of the $V_H$ domain of R15E6 without the murine signal peptide sequence. SEQ ID NO: 2 is the closest human germline gene V-region, *Homo sapiens* IGHV3-73, to the murine $V_H$ domain of R15E6. SEQ ID NO: 3 and SEQ ID NO: 4 are *Homo sapiens* IGHV3-72 and *Homo sapiens* IGHV3-48, respectively, that are additional germline V-regions that are similar to SEQ ID NO: 2. The peptide sequences of SEQ ID NO: 1-4 are presented in TABLE 1.

TABLE 1

| SEQ ID NO: | Name | Amino acid sequence |
|---|---|---|
| 1 | $V_{H0}$ | MDFGLSWVFFVVFYQGVHCEVQLVETGGGLVQPKGSMKLSCAASGFTFNANAMNWIRQAPGKGLEWVARIRTKSNNYATYYAGSVKDRFTISRDDAQNMLYLQMNDLKTEDTAMYYCVRDYYGSSAWITYWGQGTLVTVSA |

TABLE 1-continued

| SEQ ID NO: | Name | Amino acid sequence |
|---|---|---|
| 47 | Truncated $V_{H0}$ | EVQLVETGGGLVQPKGSMKLSCAASGFTFNANAMNWIRQAPGKGLEWVARIRTKSNNYATYYAGSVKDRFTISRDDAQNMLYLQMNDLKTEDTAMYYCVRDYYGSSAWITYWGQGTLVTVSA |
| 2 | IGHV3-73 | EVQLVESGGGLVQPGGSLKLSCAASGFTFSGSAMHWVRQASGKGLEWVGRIRSKANSYATAYAASVKGRFTISRDDSKNTAYLQMNSLKTEDTAVYYCTR |
| 3 | IGHV3-72 | EVQLVESGGGLVQPGGSLRLSCAASGFTFSDHYMDWVRQAPGKGLEWVGRTRNKANSYTTEYAASVKGRFTISRDDSKNSLYLQMNSLKTEDTAVYYCAR |
| 4 | IGHV3-48 | EVQLVESGGGLVQPGGSLRLSCAASGFTFSSYSMNWVRQAPGKGLEWVSYISSSSSTIYYADSVKGRFTISRDNAKNSLYLQMNSLRAEDTAVYYCAR |

Online databases of Human IgG sequences were searched for comparison to the murine $V_H$ domain using BLAST search algorithms, and candidate human variable domains were selected from the top 200 BLAST results. The coordinate human variable domains were reduced to four candidates based on a combination of framework homology, maintaining framework residues, and canonical loop structures. TABLE 2 lists the four selected acceptor frameworks, SEQ ID NO: 5-8. SEQ ID NO: 5 is AEX29600, SEQ ID NO: 6 is AAC51024, SEQ ID NO: 7 is AEX29289, and SEQ ID NO: 8 is ABA26204.

TABLE 2

| SEQ ID NO: | Name | Amino acid sequence |
|---|---|---|
| 5 | AEX29600 | EVQLVESGGGLVQPGGSLKLSCAASGFTFSGSAMHWVRQASGKGLEWVGRIRSKANNYATAYAASVKGRFTISRDDSKNTAYLQMNSLKTEDTAAYYCIRDYYGATRGFQHWGQGTLVTVSS |
| 6 | AAC51024 | EVQLVESGGGLVQPGGSLRLSCAASGFTFSDHYMDWVRQAPGKGLEWVGRTRNKANSYTTEYAASVKGRFTISRDDSKNSLYLQMNSLKTEDTAVYYCARYVVGATLDYWGQGTLVTVSS |
| 7 | AEX29289 | EVQLVESGGGLVQPGRSLRLSCTASGFSFGDYAMNWVRQAPGKGLEWVGFIRSKTYGGTTEYAASVKGRFTISRDDSKNIAYLQMNSLKTEDTAVYYCTRDPADFYYYSSGQTGWFDPWGQGTLVTVSS |
| 8 | ABA26204 | LVQLVESGGGLVKPGGSLRLSCAASGFTFSDYYMSWIRQAPGKGLEWVSYISSSGSTIYYADSVKGRFTISRDNAKNSLYLQMNSLRAEDTAVHYCARDGYSSSWYVDYWGQGTLVTVSS |

Grafting the CDRs of the murine $V_H$ into the acceptor frameworks (SEQ ID NO: 5-8) converted these sequences to humanized variants, which are shown in TABLE 3. SEQ ID NO: 9 is $V_{H1}$, SEQ ID NO: 10 is $V_{H2}$, SEQ ID NO: 11 is $V_{H3}$, and SEQ ID NO: 12 is $V_{H4}$.

TABLE 3

| SEQ ID NO: | Name | Amino acid sequence |
|---|---|---|
| 9 | $V_{H1}$ | EVQLVESGGGLVQPGGSLKLSCAASGFTFNANAMNWVRQAS GKGLEWVGRIRTKSNNYATYYAGSVKDRFTISRDDSKNTAY LQMNSLKTEDTAAYYCVRDYYGSSAWITYWGQGTLVTVSS |
| 10 | $V_{H2}$ | EVQLVESGGGLVQPGGSLRLSCAASGFTFNANAMNWVRQAP GKGLEWVGRIRTKSNNYATYYAGSVKDRFTISRDDSKNSLY LQMNSLKTEDTAVYYCVRDYYGSSAWITYWGQGTLVTVSS |
| 11 | $V_{H3}$ | EVQLVESGGGLVQPGRSLRLSCTASGFTFNANAMNWVRQAP GKGLEWVGRIRTKSNNYATYYAGSVKDRFTISRDDSKNIAY LQMNSLKTEDTAVYYCVRDYYGSSAWITYWGQGTLVTVSS |
| 12 | $V_{H4}$ | LVQLVESGGGLVKPGGSLRLSCAASGFTFNANAMNWIRQAP GKGLEWVSRIRTKSNNYATYYAGSVKDRFTISRDNAKNSLY LQMNSLRAEDTAVHYCVRDYYGSSAWITYWGQGTLVTVSS |

FIG. 1 shows a sequence alignment of the murine $V_H$ sequence (truncated $V_{H0}$; SEQ ID NO: 47) with four humanized variants SEQ ID NO: 9 ($V_{H1}$), SEQ ID NO: 10 ($V_{H2}$), SEQ ID NO: 11 ($V_{H3}$), and SEQ ID NO: 12 ($V_{H4}$). Residues important for the $V_H/V_K$ interface and canonical loop structure were preserved.

The percent homologies of the humanized variants to murine $V_H$ are presented in TABLE 4. The ranked order of homology of the humanized variants is $V_{H2}>V_{H1}>V_{H3}>V_{H4}$.

TABLE 4

| Humanized variant | Identical amino acids | Consensus amino acids |
|---|---|---|
| $V_{H1}$ (SEQ ID NO: 9) | 89.3% | 94.3% |
| $V_{H2}$ (SEQ ID NO: 10) | 90.2% | 96.7% |
| $V_{H3}$ (SEQ ID NO: 11) | 87.7% | 95.1% |
| $V_{H4}$ (SEQ ID NO: 12) | 86.9% | 93.4% |

Light Chain Sequences

In TABLE 5 below, SEQ ID NO: 13 is the murine $V_L$ domain of R15E6 ($V_{L0}$), which includes the murine signal peptide sequence (underlined). SEQ ID NO: 48 is a truncated sequence of the $V_L$ domain of R15E6 without the murine signal peptide sequence. SEQ ID NO: 14 is the closest human germline gene V-region, *Homo sapiens* IGKV1-16, to the murine $V_L$ domain of R15E6. SEQ ID NO: 15 is IGKV4-1 and is very similar to IGKV1-16.

TABLE 5

| SEQ ID NO: | Name | Amino acid sequence |
|---|---|---|
| 13 | $V_{L0}$ | MESQTQVFVYMLLWLSGVEGDIVMTQSHKFMSTSVGDR VSITCKASQHVGTAVAWYQQKPDQSPKQLIYWASTRHT GVPDRFTGSGSGTDFTLTISNVQSEDLADYFCQQYSSY PFTFGSGTKLEIK |
| 48 | Truncated $V_{L0}$ | DIVMTQSHKFMSTSVGDRVSITCKASQHVGTAVAWYQQ KPDQSPKQLIYWASTRHTGVPDRFTGSGSGTDFTLTIS NVQSEDLADYFCQQYSSYPFTFGSGTKLEIK |
| 14 | IGKV1-16 | DIQMTQSPSSLSASVGDRVTITCRASQGISNYLAWFQQ KPGKAPKSLIYAASSLQSGVPSRFSGSGSGTDFTLTIS SLQPEDFATYYCQQYNSYP |
| 15 | IGKV4-1 | DIVMTQSPDSLAVSLGERATINCKSSQSVLYSSNNKNY LAWYQQKPGQPPKLLIYWASTRESGVPDRFSGSGSGTD FTLTISSLQAEDVAVYYCQQYYSTP |

Online databases of Human IgK sequences were searched for comparison to the murine $V_L$ domain using BLAST search algorithms, and candidate human variable domains were selected from the top 200 BLAST results. These coordinate human variable domains were reduced to four candidates based on a combination of framework homology, maintaining framework residues and canonical loop structure. TABLE 6 lists the four selected acceptor frameworks. SEQ ID NO: 16 is AF234256_1, SEQ ID NO: 17 is AAD03722, SEQ ID NO: 18 is AAY33352, and SEQ ID NO: 19 is AAZ09113.

TABLE 6

| SEQ ID NO: | Name | Amino acid sequence |
|---|---|---|
| 16 | AF234256_1 | DVVMTQSPSFLSASVGDRVTITCRASQGIS- NYLAWYQ QRPGKAPKLLI- YAASTLQTGVPSRFSGSGSGTEFTLT ISSLQPEDFATYFCQQLGGYPLTFGGGTKLEIK |
| 17 | AAD03722 | DIVMTQSPDSLAVSLGERATINCK- SSQSVLYSSNNKN YLAWYQQKPGQPPKLLIYWAST- RESGVPDRFSGSGSG TDFTLTISSLQAEDVAVYYCQQYYSTPY- TFGQGTKLE IK |
| 18 | AAY33352 | DIQMTQSPFSLSASVGDRVTITCRASQ- GIGSSLAWYQ QKPGKAPKLLI- YAASSLQSGVPSRFSGSGSGTDFTLT ISSLQPEDFATYFCLQHHDYPLTFGGGTKLEIK |
| 19 | AAZ09113 | DIVMTQSPDSLAVSLGERATINCK- SSQSVFYSSNNKN YLAWYQQKPEQPPKLLIYWAST- RESGVPDRFSGSGSG TDFTLTISSLQAEDVA- VYYCQQYYSSPLTFGGGTKVE IK |

Grafting the CDRs of the murine $V_L$ into these acceptor frameworks converted these sequences to humanized variants, which are shown in TABLE 7. SEQ ID NO: 20 is $V_{L1}$, SEQ ID NO: 21 is $V_{L2}$, SEQ ID NO: 22 is $V_{L3}$, and SEQ ID NO: 23 is $V_{L4}$.

TABLE 7

| SEQ ID NO: | Name | Amino acid sequence |
|---|---|---|
| 20 | $V_{L1}$ | DVVMTQSPSFLSASVGDRVTITCKASQHVGTAVAWYQQRPGK APKLLIYWASTRHTGVPSRFSGSGSGTEFTLTISSLQPEDFA TYFCQQYSSYPFTFGGGTKLEIK |
| 21 | $V_{L2}$ | DIVMTQSPDSLAVSLGERATINCKASQHVGTAVAWYQQKPGQ PPKLLIYWASTRHTGVPDRFSGSGSGTDFTLTISSLQAEDVA VYYCQQYSSYPFTFGQGTKLEIK |
| 22 | $V_{L3}$ | DIQMTQSPFSLSASVGDRVTITCKASQHVGTAVAWYQQKPGK APKLLIYWASTRHTGVPSRFSGSGSGTDFTLTISSLQPEDFA TYFCQQYSSYPFTFGGGTKLEIK |
| 23 | $V_{L4}$ | DIVMTQSPDSLAVSLGERATINCKASQHVGTAVAWYQQKPEQ PPKLLIYWASTRHTGVPDRFSGSGSGTDFTLTISSLQAEDVA VYYCQQYSSYPFTFGGGTKVEIK |

FIG. 2 shows a sequence alignment of the murine $V_L$ sequence (truncated $V_{L0}$; SEQ ID NO: 48) with four humanized $V_L$ variants SEQ ID NO: 20 ($V_{L1}$), SEQ ID NO: 21

(V$_{L2}$), SEQ ID NO: 22 (V$_{L3}$), and SEQ ID NO: 23 (V$_{L4}$). Residues important for the V$_L$/V$_K$ interface and canonical loop structure were preserved.

The percent homologies of the humanized variants to murine V$_L$ are presented in TABLE 8. The rank order of homology of the humanized variants is V$_{L3}$>V$_{L1}$>V$_{L2}$>V$_{L4}$.

TABLE 8

| Humanized variant | Identical amino acids | Consensus amino acids |
|---|---|---|
| V$_{L1}$ (SEQ ID NO: 20) | 81.3% | 88.8% |
| V$_{L2}$ (SEQ ID NO: 21) | 79.4% | 88.8% |
| V$_{L3}$ (SEQ ID NO: 22) | 82.2% | 86.9% |
| V$_{L4}$ (SEQ ID NO: 23) | 78.5% | 89.7% |

Design of Humanized Antibodies: Combination of 4 V$_H$ and 4 V$_L$ Chains

Mouse variable chains were humanized by grafting the murine CDR sequences onto suitable human antibody donor sequences as described above in the context of the IgG4 heavy chain for the expression of intact antibody proteins. A panel of full length humanized antibodies was then codon-optimized for expression in the Chinese hamster ovary (CHO) cell line. The four variants designed for each variable chain using different human donor sequences produced a matrix of 16 human antibodies for expression, the heavy chain and light chain pairings of which are shown in TABLE 9. A chimeric variant with full mouse variable domains (V$_{H0}$-V$_{L0}$) grafted to human IgG4 constant domains was created as a positive control in binding and functional assays.

TABLE 9

| | | | | |
|---|---|---|---|---|
| V$_{H1}$-V$_{L1}$ | SEQ ID NO: 9-SEQ ID NO: 20 | V$_{H3}$-V$_{L1}$ | SEQ ID NO: 11-SEQ ID NO: 20 |
| V$_{H1}$-V$_{L2}$ | SEQ ID NO: 9-SEQ ID NO: 21 | V$_{H3}$-V$_{L2}$ | SEQ ID NO: 11-SEQ ID NO: 21 |
| V$_{H1}$-V$_{L3}$ | SEQ ID NO: 9-SEQ ID NO: 22 | V$_{H3}$-V$_{L3}$ | SEQ ID NO: 11-SEQ ID NO: 22 |
| V$_{H1}$-V$_{L4}$ | SEQ ID NO: 9-SEQ ID NO: 23 | V$_{H3}$-V$_{L4}$ | SEQ ID NO: 11-SEQ ID NO: 23 |
| V$_{H2}$-V$_{L1}$ | SEQ ID NO: 10-SEQ ID NO: 20 | V$_{H4}$-V$_{L1}$ | SEQ ID NO: 12-SEQ ID NO: 20 |
| V$_{H2}$-V$_{L2}$ | SEQ ID NO: 10-SEQ ID NO: 21 | V$_{H4}$-V$_{L2}$ | SEQ ID NO: 12-SEQ ID NO: 21 |
| V$_{H2}$-V$_{L3}$ | SEQ ID NO: 10-SEQ ID NO: 22 | V$_{H4}$-V$_{L3}$ | SEQ ID NO: 12-SEQ ID NO: 22 |
| V$_{H2}$-V$_{L4}$ | SEQ ID NO: 10-SEQ ID NO: 23 | V$_{H4}$-V$_{L4}$ | SEQ ID NO: 12-SEQ ID NO: 23 |

T-Cell Epitope Screen
Heavy Chain.

The presentation of peptide sequences in the groove of MHC Class II molecules leads to activation of CD8+ T-cells and an immunogenic response. To reduce this response, therapeutic proteins can be designed to avoid the incorporation of T-cell epitopes that can activate T-cells by reducing the affinity of binding to the MHC Class II molecules.

The murine antibody V$_H$ and V$_L$ and the humanized variant sequences were screened for MHC II binding peptides to determine that the humanization process had removed peptide sequences with high affinity using in silico algorithms. TABLE 10 shows the results of the screen, with high affinity T-cell epitope cores in bold (IC$_{50}$<50 nM). The human germline sequences ICHV3-73, ICHV3-72, and ICHV3-48 were also analyzed for comparison. Any potential T-cell epitopes present in the germline sequence and matched in the humanized variants are italicized. CDRs are underlined.

TABLE 10

| SEQ ID NO: | Name | Amino acid sequence |
|---|---|---|
| 2 | IGHV3-73 | EVQLVESGGGLVQPGGSLKLSCAASGFTFSGSAMHWV RQASGKGLEWVGRIRSKA*NSYATAYAASVK*GRFTISR DD*SKNTAYLQMNSLKT*EDTAVYYCTR |
| 3 | IGHV3-72 | EVQLVESGGGLVQPGGSLRLSCAASGFTFSDHYMDWV RQAPGKGLEWVGRTRNKA*NSYTTEYAASVK*GRFTISR DD*SKNSLYLQMNSLKT*EDTAVYYCAR |
| 4 | IGHV3-48 | EVQLVESGGGLVQPGGSLRLSCAASGFTFSSYSMNWV RQAPGK*GLEWVSYISSSSSTI*YYADSVKGRFTISRD*N AKNSLYLQMNSLRA*EDTAVYYCAR |
| 47 | Truncated V$_{H0}$ | EVQLVETGGGLVQPKGSMKLSCAASGFTFNANAMNWI RQAPGKGLEWVA*RIRTKSNNYATYYAGSVK*DRFTISR DDAQNMLYLQMNDLKTEDTAMYYC*VRDYYGSSAWITY* WGQGTLVTVSA |
| 9 | V$_{H1}$ | EVQLVESGGGLVQPGGSLKLSCAASGFTFNANAMNWV RQASGKGLEWVG*RIRTKSNNYATYYAGSVK*DRFTISR DD*SKNTAYLQMNSLKT*EDTAAYYC*VRDYYGSSAWITY* WGQGTLVTVSS |
| 10 | V$_{H2}$ | EVQLVESGGGLVQPGGSLRLSCAASGFTFNANAMNWV RQAPGKGLEWVG*RIRTKSNNYATYYAGSVK*DRFTISR DD*SKNSLYLQMNSLKT*EDTAVYYC*VRDYYGSSAWITY* WGQGTLVTVSS |
| 11 | V$_{H3}$ | EVQLVESGGGLVQPGRSLRLSCTASGFTFNANAMNWV RQAPGKGLEWVG*RIRTKSNNYATYYAGSVK*DRFTISR DD*SKNIAYLQMNSLKT*EDTAVYYC*VRDYYGSSAWITY* WGQGTLVTVSS |
| 12 | V$_{H4}$ | LVQLVESGGGLVKPGGSLRLSCAASGFTFNANAMNWI RQAPGKGLEWVS*RIRTKSNNYATYYAGSVK*DRFTISR DN*AKNSLYLQMNSTRA*EDTAVHYC*VRDYYGSSAWITY* WGQGTLVTVSS |
| 54 | Heavy chain CDR1 | GFTFNANAMN |
| 55 | Heavy chain CDR2 | RIRTKSNNYATYYAGSVKD |
| 56 | Heavy chain CDR3 | VRDYYGSSAWITY |

TABLE 11 shows the results of the screen, with high affinity T-cell epitope cores in bold (IC$_{50}$<50 nM). The human germline sequences IGKV1-16 and IGKV4-1 were also analyzed for comparison, and any potential T-cell epitopes present in the germline sequence and matched in the humanized variants, are italicized. The CDRs are underlined.

TABLE 11

| SEQ ID NO: | Name | Amino acid sequence |
|---|---|---|
| 14 | IGKV1-16 | DIQMTQSPSSLSASVGDRVTITC*RASQGISNY LAWFQQKPGKA*PKSLIYAASSLQ*SGVPSRFSG SGSGTDFTLTISSLQPEDFATYYC*QQYNSYP |
| 15 | IGKV4-1 | DIVMTQSPDSLAVSLGERATINC*KSSQSVLYS SNNKNYLA*WYQQKPGQPPKLLIYWASTRESGV PDRFSGSGSGTD*FTLTISSLQAEDV*AVYYC*QQ YYSTP |
| 48 | Truncated V$_{L0}$ | DIVMTQSHKFMSTSVGDRVSITC*KASQHVGTA VA*WYQQKPDQSPKQLIY*WASTRHTG*VPDRFTG SGSGTDFTLTISNVQSEDLADYFCQQYSSYPF TFGSGTKLEIK |

TABLE 11-continued

| SEQ ID NO: | Name | Amino acid sequence |
|---|---|---|
| 20 | V_L1 | DVVMTQSPSFLSASVGDRVTITC<u>KASQHVGTA VA</u>WYQQRPGKAPKLLI<u>YWASTRHT</u>GVPSRFSG SGSGTEFTLTISSLQPEDFATYFC<u>QQYSSYPF TFGGGTKLE</u>IK |
| 21 | V_L2 | DIVMTQSPDSLAVSLGERATINC<u>KASQHVGTA VA</u>WYQQKPGQPPKLLI<u>YWASTRHT</u>GVPDRFSG SGSGTD*FTLTISSLQAED*VAVYYC<u>QQYSSYPF TFGQGTKLE</u>IK |
| 22 | V_L3 | DIQMTQSPFSLSASVGDRVTITC<u>KASQHVGTA VA</u>WYQQKPGKAPKLLI<u>YWASTRHT</u>GVPSRFSG SGSGTDFTLTISSLQPEDFATYFC<u>QQYSSYPF TFGGGTKLE</u>IK |
| 23 | V_L4 | DIVMTQSPDSLAVSLGERATINC<u>KASQHVGTA VA</u>WYQQKPEQPPKLLI<u>YWASTRHT</u>GVPDRFSG SGSGTD*FTLTISSLQAED*VAVYYC<u>QQYSSYPF TFGGGTKVE</u>IK |
| 57 | Light chain CDR1 | KASQHVGTAVA |
| 58 | Light chain CDR2 | WASTRHT |
| 59 | Light chain CDR3 | QQYSSYPFT |

The murine $V_{LO}$ contains a T-cell epitope within the CDR3/framework 4 region of the light chain, which is not present in 3 of the humanized variants.

Post-Translational Modifications

Fv Glycosylation.

The N-linked glycosylation motif is NXS/T, where X is any amino acid except proline. This motif was not present in the murine or humanized variants of R15E6 $V_H$ or $V_L$.

Deamidation.

The amino acid motifs SNG, ENN, LNG, and LNN can be prone to deamidation of asparagine to provide aspartic acid. None of these four motifs were present in the murine or humanized variants of R15E6 $V_H$ or $V_L$.

Signal Peptides.

Murine antibody signal peptides can result in higher levels of expression in CHO cells. The following signal peptides can be incorporated into the humanized variants.

Heavy chain signal peptide (SEQ ID NO: 24):
MGWTLVFLFLLSVTAGVHS

Light chain signal peptide (SEQ ID NO: 25):
MVSSAQFLGLLLLCFQGTRC

Each of the $V_H$ domains can be synthesized in-frame with a human IgG4 isotype constant domain sequence, with a stabilizing S228P mutation. The entire heavy chain sequence can be codon optimized, and the DNA sequence can be verified. The amino acid sequence of the IgG4 constant domain with S228P mutation (SEQ ID NO: 26) is:

ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFELYSRLTVDKSRWQEG

NVFSCSVMHEALHNHYTQKSLSLSLGK

Each of the $V_L$ domains can be synthesized in-frame with a human IgK isotype constant domain sequence. The entire light chain sequence can then be codon optimized, and the DNA sequence can be verified. The amino acid sequence of the IgK constant domain (SEQ ID NO: 27) is:

TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC

Each of the variant chains can be verified by DNA sequencing analysis. Then, transient transfection and expression of each of the humanized antibodies can be pursued. One chimeric antibody can be expressed for use as a positive control and can have the murine variable domains, the human Ig constant domains. The 16 humanized variants only have humanized variable domains and human Ig constant domains. TABLE 12 shows the heavy chain and light chain parings that provide the 16 humanized variants with humanized variable domains and human Ig constant domains.

TABLE 12

| Chimeric Antibody | HC0-LC0 | | | |
|---|---|---|---|---|
| Humanized Variants | HC1-LC1 | HC1-LC2 | HC1-LC3 | HC1-LC4 |
| | HC2-LC1 | HC2-LC2 | HC2-LC3 | HC2-LC4 |
| | HC3-LC1 | HC3-LC2 | HC3-LC3 | HC3-LC4 |
| | HC4-LC1 | HC4-LC2 | HC4-LC3 | HC4-LC4 |

TABLE 13 and TABLE 14 list the full amino acid sequences of each humanized heavy and light chain.

TABLE 13

| SEQ ID NO: | Name | Amino acid sequence |
|---|---|---|
| 28 | HC0 | MGWTLVFLFLLSVTAGVHSEVQLVETGG-GLVQPKGSMKL SCAASGFTFNANAMNWIRQAPGKGLEWVARIRTKSN-NYA TYYAGSVKDRFTISRDDAQNMLYLQMNDLKTED-TAMYYC VRDYYGSSAWITWGQGTLVTVSAASTKGPSVF-PLAPCSR STSESTAALGCLVKDYFPEPVTVSWNSGALT-SGVHTFPA VLQSSGLYS-LSSVVTVPSSSLGTKTYTCNVDHKPSNTKV DKRVESKYGPPCPPCPAPE-FLGGPSVFLFPPKPKDTLMI SRTPEVTCVVVDVSQEDPE-VQFNWYVDGVEVHNAKTKPR EEQFN-STYRVVSVLTVLHQDWLNGKEYKCKVSNKGLPSS IEKTISKAKGQPREPQVYTLPPSQEEMTKNQVSLT-CLVK GFYPSDIAVEWESNGQPENNYKTTPPVLDSDGSFF-LYSR LTVDKSRWQEGNVFSCSVMHEALHNHYTQKSLSLSLGK |

TABLE 13-continued

| SEQ ID NO: | Name | Amino acid sequence |
|---|---|---|
| 29 | HC1 | MGWTLVFLFLLSVTAGVHSEVQLVESGG-GLVQPGGSLKL SCAASGFTFNANAMNWVRQASGKGLEWVGRIRTKSN-NYA TYYAGSVKDRFTISRDDSKNTAYLQMNSLKTED-TAAYYC VRDYYGSSAWITYWGQGTLVTVSSASTKGPSVF-PLAPCS RSTSESTAALGCLVKDYFPEPVTVSWNSGALT-SGVHTFP AVLQSSGLYS-LSSVVTVPSSSLGTKTYTCNVDHKPSNTK VDKRVESKYGPPCPPCPAPE-FLGGPSVFLFPPKPKDTLM ISRTPEVTCVVVDVSQEDPE-VQFNWYVDGVEVHNAKTKP REEQFN-STYRVVSVLTVLHQDWLNGKEYKCKVSNKGLPS SIEKTISKAKGQPREPQVYTLPPSQEEMTKNQVSLT-CLV KGFYPSDIAVEWESNGQPENNYKTTPPVLDSDGSFF-LYS RLTVDKSRWQEGNVFSCSVMHEALHN-HYTQKSLSLSLGK |
| 30 | HC2 | MGWTLVFLFLLSVTAGVHSEVQLVESGG-GLVQPGGSLRL SCAASGFTFNANAMNWVRQAPGKGLEWVGRIRTKSN-NYA TYYAGSVKDRFTISRDDSKNSLYLQMNSLKTED-TAVYYC VRDYYGSSAWITYWGQGTLVTVSSASTKGPSVF-PLAPCS RSTSESTAALGCLVKDYFPEPVTVSWNSGALT-SGVHTFP AVLQSSGLYS-LSSVVTVPSSSLGTKTYTCNVDHKPSNTK VDKRVESKYGPPCPPCPAPE-FLGGPSVFLFPPKPKDTLM ISRTPEVTCVVVDVSQEDPE-VQFNWYVDGVEVHNAKTKP REEQFN-STYRVVSVLTVLHQDWLNGKEYKCKVSNKGLPS SIEKTISKAKGQPREPQVYTLPPSQEEMTKNQVSLT-CLV KGFYPSDIAVEWESNGQPENNYKTTPPVLDSDGSFF-LYS RLTVDKSRWQEGNVFSCSVMHEALHN-HYTQKSLSLSLGK |
| 31 | HC3 | MGWTLVFLFLLSVTAGVHSEVQLVESGG-GLVQPGRSLRL SCTASGFTFNANAMNWVRQAPGKGLEWVGRIRTKSN-NYA TYYAGSVKDRFTISRDDSKNIAYLQMNSLKTED-TAVYYC VRDYYGSSAWITYWGQGTLVTVSSASTKGPSVF-PLAPCS RSTSESTAALGCLVKDYFPEPVTVSWNSGALT-SGVHTFP AVLQSSGLYS-LSSVVTVPSSSLGTKTYTCNVDHKPSNTK VDKRVESKYGPPCPPCPAPE-FLGGPSVFLFPPKPKDTLM ISRTPEVTCVVVDVSQEDPE-VQFNWYVDGVEVHNAKTKP REEQFN-STYRVVSVLTVLHQDWLNGKEYKCKVSNKGLPS SIEKTISKAKGQPREPQVYTLPPSQEEMTKNQVSLT-CLV KGFYPSDIAVEWESNGQPENNYKTTPPVLDSDGSFF-LYS RLTVDKSRWQEGNVFSCSVMHEALHN-HYTQKSLSLSLGK |
| 32 | HC4 | MGWTLVFLFLLSVTAGVHSLVQLVESGG-GLVKPGGSLRL SCAASGFTFNANAMNWIRQAPGKGLEWVSRIRTKSN-NYA TYYAGSVKDRFTISRDNAKNSLYLQMNSLRAED-TAVHYC VRDYYGSSAWITYWGQGTLVTVSSASTKGPSVF-PLAPCS RSTSESTAALGCLVKDYFPEPVTVSWNSGALT-SGVHTFP AVLQSSGLYS-LSSVVTVPSSSLGTKTYTCNVDHKPSNTK VDKRVESKYGPPCPPCPAPE-FLGGPSVFLFPPKPKDTLM ISRTPEVTCVVVDVSQEDPE-VQFNWYVDGVEVHNAKTKP REEQFN-STYRVVSVLTVLHQDWLNGKEYKCKVSNKGLPS SIEKTISKAKGQPREPQVYTLPPSQEEMTKNQVSLT-CLV KGFYPSDIAVEWESNGQPENNYKTTPPVLDSDGSFF-LYS RLTVDKSRWQEGNVFSCSVMHEALHN-HYTQKSLSLSLGK |

TABLE 14

| SEQ ID NO: | Name | Amino acid sequence |
|---|---|---|
| 33 | LC0 | MVSSAQFLGLLLLCFQGTRCDI-VMTQSHKFMSTSVGDRV SITCKASQHVGTAVAWYQQKPDQSPKQLIYWAST-RHTGV PDRFTGSGSGTDFTLTISNVQSEDLA-DYFCQQYSSYPFT FGSGTKLEIKRTVAAPSVFIFPPSDEQLKSG-TASVVCLL NNFYPREAKVQWKVDNALQSGNSQESVTEQDSKDS-TYSL SSTLTLSKADYEKHKVYACE-VTHQGLSSPVTKSFNRGEC |
| 34 | LC1 | MVSSAQFLGLLLLCFQGTRCDVVMTQSPSFL-SASVGDRV TITCKASQHVGTAVAWYQQRPGKAPKLLIYWAST-RHTGV PSRFSGSGSGTEFTLTISSLQPEDFA-TYFCQQYSSYPFT FGGGTKLEIKRTVAAPSVFIFPPSDEQLKSG-TASVVCLL NNFYPREAKVQWKVDNALQSGNSQESVTEQDSKDS-TYSL SSTLTLSKADYEKHKVYACE-VTHQGLSSPVTKSFNRGEC |
| 35 | LC2 | MVSSAQFLGLLLLCFQGTRCDIVMTQSPD-SLAVSLGERA TINCKASQHVGTAVAWYQQKPGQPPKLLIYWAST-RHTGV PDRFSGSGSGTDFTLTISSLQAEDVA-VYYCQQYSSYPFT FGQGTKLEIKRTVAAPSVFIFPPSDEQLKSG-TASVVCLL NNFYPREAKVQWKVDNALQSGNSQESVTEQDSKDS-TYSL SSTLTLSKADYEKHKVYACE-VTHQGLSSPVTKSFNRGEC |
| 36 | LC3 | MVSSAQFLGLLLLCFQGTRCDIQMTQSPFSL-SASVGDRV TITCKASQHVGTAVAWYQQKPGKAPKLLIYWAST-RHTGV PSRFSGSGSGTDFTLTISSLQPEDFA-TYFCQQYSSYPFT FGGGTKLEIKRTVAAPSVFIFPPSDEQLKSG-TASVVCLL NNFYPREAKVQWKVDNALQSGNSQESVTEQDSKDS-TYSL SSTLTLSKADYEKHKVYACE-VTHQGLSSPVTKSFNRGEC |
| 37 | LC4 | MVSSAQFLGLLLLCFQGTRCDIVMTQSPD-SLAVSLGERA |

TABLE 14-continued

| SEQ ID NO: | Name | Amino acid sequence |
|---|---|---|
| | | TINCKASQHVGTAVAWYQQKPEQPPKLLIYWAST-RHTGV PDRFSGSGSGTDFTLTISSLQAEDVA-VYYCQQYSSYPFT FGGGTKVEIKRTVAAPSVFIFPPSDEQLKSG-TASVVCLL NNFYPREAKVQWKVDNALQSGNSQESVTEQDSKDS-TYSL SSTLTLSKADYEKHKVYACE-VTHQGLSSPVTKSFNRGEC |

Target sequences can have at least about 80% homology, at least about 81% homology, at least about 82% homology, at least about 83% homology, at least about 84% homology, at least about 85% homology, at least about 86% homology, at least about 87% homology, at least about 88% homology, at least about 89% homology, at least about 90% homology, at least about 91% homology, at least about 92% homology, at least about 93% homology, at least about 94% homology, at least about 95% homology, at least about 96% homology, at least about 97% homology, at least about 98% homology, at least about 99% homology, at least about 99.1% homology, at least about 99.2% homology, at least about 99.3% homology, at least about 99.4% homology, at least about 99.5% homology, at least about 99.6% homology, at least about 99.7% homology, at least about 99.8% homology, at least about 99.9% homology, at least about 99.91% homology, at least about 99.92% homology, at least about 99.93% homology, at least about 99.94% homology, at least about 99.95% homology, at least about 99.96% homology, at least about 99.97% homology, at least about 99.98% homology, or at least about 99.99% homology to an amino acid sequence provided herein.

Various methods and software programs can be used to determine the homology between two or more peptides or nucleic acids, such as NCBI BLAST, Clustal W, MAFFT, Clustal Omega, AlignMe, Praline, or another suitable method or algorithm.

Pharmaceutical Compositions

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, intramuscular, oral, parenteral, ophthalmic, and topical administration.

A pharmaceutical composition can be administered to the eye via any suitable form or route including, for example, topical, oral, systemic, intravitreal, intracameral, subconjunctival, subtenon, retrobulbar, intraocular, posterior juxtascleral, periocular, subretinal, and suprachoroidal administration. The compositions can be administered by injecting the formulation in any part of the eye including anterior chamber, posterior chamber, vitreous chamber (intravitreal), retina proper, and/or subretinal space. The compositions can be delivered via a non-invasive method. Non-invasive modes of administering the formulation can include using a needleless injection device. Multiple administration routes can be employed for efficient delivery of the pharmaceutical compositions.

A pharmaceutical composition can be targeted to any suitable ocular cell including, for example, endothelial cells such as vascular endothelial cells, cells of the retina such as retinal pigment epilthelium (RPE), corneal cells, fibroblasts, astrocytes, glial cells, pericytes, iris epithelial cells, cells of neural origin, ciliary epithelial cells, Muller cells, muscle cells surrounding and attached to the eye such as cells of the lateral rectus muscle, orbital fat cells, cells of the sclera and episclera, cells of the trabecular meshwork, and connective tissue cells.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

Pharmaceutical formulations for administration can include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, for example, sterile pyrogen-free water, before use.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors.

In some embodiments, the compounds described herein can be used singly or in combination with one or more therapeutic agents as components of mixtures. For example, a VE-PTP (HPP-β) inhibitor of the disclosure can be co-formulated or co-administered with antibodies, for example, anti-VEGF agents. An anti-VEGF agent can be a compound, an antibody, or an antibody fragment, variant, or derivative thereof. Non-limiting examples of an anti-VEGF agent include bevacizumab (Avastin®), ranibizumab (Lucentis®), and aflibercept (Eylea®). In some embodiments, the compounds described herein can be used before, during, or after treatment with an anti-VEGF agent.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising compounds described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers, and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16, or about 24 hours.

The disclosed compositions can optionally comprise pharmaceutically-acceptable preservatives.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

A compound described herein can be conveniently formulated into pharmaceutical compositions composed of one or more pharmaceutically-acceptable carriers. See e.g., Remington's Pharmaceutical Sciences, latest edition, by E. W. Martin Mack Pub. Co., Easton, Pa., incorporated by reference in its entirety, which discloses typical carriers and conventional methods of preparing pharmaceutical compositions. Such carriers can be carriers for administration of compositions to humans and non-humans, including solutions such as sterile water, saline, and buffered solutions at physiological pH. Pharmaceutical compositions can also include one or more additional active ingredients such as antimicrobial agents, anti-inflammatory agents, and anesthetics.

Non-limiting examples of pharmaceutically-acceptable carriers include saline, Ringer's solution, and dextrose solution. In some embodiments, the pH of the solution can be from about 5 to about 8, and can be from about 7 to about 7.5. Further carriers include sustained release preparations such as semipermeable matrices of solid hydrophobic polymers containing the compound. The matrices can be in the form of shaped articles, for example, films, liposomes, microparticles, or microcapsules.

The disclosed methods relate to administering an antibody targeting VE-PTP (HPP-$\beta$) as part of a pharmaceutical composition. Compositions suitable for topical administration can be used. In some embodiments, compositions of the invention can comprise a liquid comprising an active agent in solution, in suspension, or both. Liquid compositions can include gels. A liquid composition can be, for example, aqueous. A composition is an in situ gellable aqueous composition. In iteration, the composition is an in situ gellable aqueous solution. Such a composition can comprise a gelling agent in a concentration effective to promote gelling upon contact with the eye or lacrimal fluid in the exterior of the eye. Aqueous compositions can have ophthalmically-compatible pH and osmolality. The composition can comprise an ophthalmic depot formulation comprising an active agent for subconjunctival administration. Microparticles comprising an active agent can be embedded in a biocompatible, pharmaceutically-acceptable polymer or a lipid encapsulating agent. The depot formulations can be adapted to release all or substantially all the active material over an extended period of time. The polymer or lipid matrix, if present, can be adapted to degrade sufficiently to be transported from the site of administration after release of all or substantially all the active agent. The depot formulation can be a liquid formulation, comprising a pharmaceutical acceptable polymer and a dissolved or dispersed active agent. Upon injection, the polymer forms a depot at the injections site, for example, by gelifying or precipitating. The composition can comprise a solid article that can be inserted in a suitable location in the eye, such as between the eye and eyelid or in the conjuctival sac, where the article releases the active agent. Solid articles suitable for implantation in the eye in such fashion can comprise polymers and can be bioerodible or non-bioerodible.

Pharmaceutical formulations can include additional carriers, as well as thickeners, diluents, buffers, preservatives, and surface active agents in addition to the agents disclosed herein.

The pH of the disclosed composition can range from about 3 to about 12. The pH of the composition can be, for example, from about 3 to about 4, from about 4 to about 5, from about 5 to about 6, from about 6 to about 7, from about 7 to about 8, from about 8 to about 9, from about 9 to about 10, from about 10 to about 11, or from about 11 to about 12 pH units. The pH of the composition can be, for example, about 3, about 4, about 5, about 6, about 7, about 8, about 9, about 10, about 11, or about 12 pH units. The pH of the composition can be, for example, at least 3, at least 4, at least 5, at least 6, at least 7, at least 8, at least 9, at least 10, at least 11 or at least 12 pH units. The pH of the composition can be, for example, at most 3, at most 4, at most 5, at most 6, at most 7, at most 8, at most 9, at most 10, at most 11, or at most 12 pH units. If the pH is outside the range desired by the formulator, the pH can be adjusted by using sufficient pharmaceutically-acceptable acids and bases.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anti-cholinergics/anti-spasmotics, antidiabetic agents, antihypertensive agents, anti-neoplastics, cardiovascular agents, central nervous system agents, coagulation modifiers, hormones, immunologic agents, immunosuppressive agents, and ophthalmic preparations.

In some embodiments, the pharmaceutical composition provided herein comprises a therapeutically effective amount of a compound in admixture with a pharmaceutically-acceptable carrier and/or excipient, for example, saline, phosphate buffered saline, phosphate and amino acids, polymers, polyols, sugar, buffers, preservatives, and other proteins. Illustrative agents include octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene, and glycol.

Methods of Administration and Treatment Methods

Pharmaceutical compositions described herein can be administered for prophylactic and/or therapeutic treatments. In therapeutic applications, the compositions can be administered to a subject already suffering from a disease or condition, in an amount sufficient to cure or at least partially arrest the symptoms of the disease or condition, or to cure, heal, improve, or ameliorate the condition. Compositions can also be administered to lessen a likelihood of developing, contracting, or worsening a condition. Amounts effective for this use can vary based on the severity and course of the disease or condition, previous therapy, the subject's health status, weight, and response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any practical route, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein can be administered in conjunction with other therapies, for example, chemotherapy, radiation, surgery, anti-inflammatory agents, and selected vitamins. The other agents can be administered prior to, after, or concomitantly with the pharmaceutical compositions.

Dosing

The VE-PTP (HPP-β) antibody can be administered at a dosage of about 0.01 mg/kg to about 50 mg/kg, about 0.1 mg/kg to about 10 mg/kg, about 1 mg/kg to about 10 mg/kg, about 5 mg/kg to about 10 mg/kg, about 1 mg/kg to about 5 mg/kg, or about 3 mg/kg to about 7 mg/kg by weight of the subject.

The VE-PTP (HPP-β) antibody can be administered at any interval desired. The administration of the compound can have irregular dosing schedules to accommodate either the person administering the compound or the subject receiving the compound. For example, the compound can be administered once a week, 2 times a week, 3 times a week, 4 times a week, 6 times a week, 6 times a week, 7 times a week, 8 times a week, 9 times a week or 10 times a week. The interval between daily dosing can be any hourly interval, for example, every hour, every 2 hours, every 3 hours, every 4 hours, every 5 hours, every 6 hours, every 7 hours, every 8 hours, every 9 hours, every 10 hours, every 11 hours, or every 12 hours. The dosing schedules for administration of a VE-PTP (HPTP-β) antibody include, but are not limited to, once daily, three-times weekly, twice weekly, once weekly, three times, monthly, twice monthly, once monthly, once every other month, yearly, two-timed yearly, three-times yearly, or four-times yearly. In some embodiments, the VE-PTP (HPTP-β) antibody can be administered every other week.

In addition, the amount of the VE-PTP (HPTP-β) antibody administered can be of the same amount in each dose or the dosage can vary between doses. For example, a first amount dosed in the morning and a second amount administered in the evening. The dosage for administration can vary depending upon the schedule of the anti-VEGF administration.

The anti-VE-PTP antibody can be administered in combination with any anti-VEGF agent in any combination, for example, at the beginning of the treatment, at any time during the treatment or at any time after treatment with the anti-VEGF agent has concluded. In addition, the dosage of the VE-PTP (HPTP-β) inhibitors can be adjusted during treatment. Also, the amount of anti-VEGF agent can be adjusted during treatment.

Further non-limiting examples of VEGF-modulating agents include non-inflammatory agents, for example, dexamethasone, fluocinolone, and triamcinolone. In addition, the disclosed methods can include implants which deliver an anti-VEGF agent. For example, VE-PTP (HPTP-β) inhibitors can be co-administered either before, during or after an implant is provided to a subject suffering from a disease or condition described herein.

Anti-VEGF treatments can be administered, for example, monthly, once every 3 months, once every 6 months, or yearly, wherein the VE-PTP (HPTP-β) inhibitor is administered at any frequency between treatments.

Also disclosed herein are methods for treating a disease or condition as disclosed herein. The method comprises administering to a subject:
a) a therapeutically-effective amount of a VE-PTP (HPTP-β) inhibitor; and
b) a therapeutically-effective amount of an anti-VEGF agent;
wherein the administration of the VE-PTP (HPTP-β) inhibitor and the anti-VEGF agent can be conducted in any manner desired by the administrator, for example, as further described herein.

A VE-PTP (HPTP-β) binding agent or an anti-VEGF agent can be administered in any amount necessary or convenient. For example, a compound described herein can be administered in an amount from about 0.1 mg to about 300 mg, about 0.1 mg to about 200 mg, about 0.1 mg to about 100 mg, about 0.05 mg to about 1.5 mg, 0.1 mg to about 1.5 mg, about 0.05 mg to about 1 mg, or about 0.1 mg to about 1 mg, about 0.05 mg, about 0.06 mg, about 0.07 mg, about 0.08 mg, about 0.09 mg, about 0.1 mg, about 0.11 mg, about 0.12 mg, about 0.13 mg, about 0.14 mg, about 0.15 mg, about 0.16 mg, about 0.17, mg, about 0.18 mg, about 0.19 mg, about 0.2 mg, about 0.21 mg, about 0.22 mg, about 0.23 mg, about 0.24 mg, about 0.25 mg, about 0.26 mg, about 0.27, mg, about 0.28 mg, about 0.29 mg, about 0.3 mg, about 0.31 mg, about 0.32 mg, about 0.33 mg, about 0.34 mg, about 0.35 mg, about 0.36 mg, about 0.37, mg, about 0.38 mg, about 0.39 mg, about 0.4 mg, about 0.41 mg, about 0.42 mg, about 0.43 mg, about 0.44 mg, about 0.45 mg, about 0.46 mg, about 0.47, mg, about 0.48 mg, about 0.49 mg, about 0.5 mg, about 0.51 mg, about 0.52 mg, about 0.53 mg, about 0.54 mg, about 0.55 mg, about 0.56 mg, about 0.57, mg, about 0.58 mg, about 0.59 mg, about 0.6 mg, about 0.61 mg, about 0.62 mg, about 0.63 mg, about 0.64 mg, about 0.65 mg, about 0.66 mg, about 0.67, mg, about 0.68 mg, about 0.69 mg, about 0.7 mg, about 0.71 mg, about 0.72 mg, about 0.73 mg, about 0.74 mg, about 0.75 mg, about 0.76 mg, about 0.77, mg, about 0.78 mg, about 0.79 mg, about 0.8 mg, about 0.81 mg, about 0.82 mg, about 0.83 mg, about 0.84 mg, about 0.85 mg, about 0.86 mg, about 0.87, mg, about 0.88 mg, about 0.89 mg, about 0.9 mg, about 0.91 mg, about 0.92 mg, about 0.93 mg, about 0.94 mg, about 0.95 mg, about 0.96 mg, about 0.97, mg, about 0.98 mg, about 0.99 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg about 200 mg, about 210 mg, about 220 mg, about 230 mg, about 240 mg, about 250 mg, about 260 mg, about 270 mg, about 280 mg, about 290 mg, or about 300 mg per dose for a subject by any route of administration.

Intraocular Delivery

Disclosed herein are methods for intraocular delivery of compositions of the invention to a subject having a disease or condition as disclosed herein. The delivery method can include an invasive method for direct delivery of the composition to ocular cells. In some embodiments, a liquid pharmaceutical composition comprising the antibody is delivered via a subretinal injection. In some embodiments, a liquid pharmaceutical composition comprising the antibody is delivered via intravitreal or subcutaneous injection. In some embodiments, a liquid pharmaceutical composition comprising the antibody is delivered via intracameral injection. In some embodiments, the composition is delivered via multiple administration routes, for example, subretinal and/or intravitreous, to increase efficiency of the antibody delivery. In some embodiments, the subretinal and/or intravitreal injection is preceded by a vitrectomy.

The intraocular injection can be performed over any interval of time to improve efficiency of delivery and/or to minimize or avoid damage to surrounding tissue. The interval of time for the intraocular injection can be from, for example, about 1 minute to about 60 minutes, about 1 minute to about 5 minutes, about 5 minutes to about 10 minutes, about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, or about 55 minutes to about 60 minutes.

The intraocular injection can be performed at any rate. The rate of intraocular injection can be from, for example, about 1 μL/min to about 200 μL/min, about 1 μL/min to about 10 µL/min, about 10 µL/min to about 20 µL/min, about 20 µL/min to about 30 µL/min, about 30 µL/min to about 40 µL/min, about 40 µL/min to about 50 µL/min, about 50 µL/min to about 60 µL/min, about 60 µL/min to about 70 µL/min, about 70 µL/min to about 80 µL/min, about 80 µL/min to about 90 µL/min, about 90 µL/min to about 100 µL/min, about 100 µL/min to about 110 µL/min, about 110 µL/min to about 120 µL/min, about 120 µL/min to about 130 µL/min, about 130 µL/min to about 140 µL/min, about 140 µL/min to about 150 µL/min, about 150 µL/min to about 160 µL/min, about 160 µL/min to about 170 µL/min, about 170 µL/min to about 180 µL/min, about 180 µL/min to about 190 µL/min, or about 190 µL/min to about 200 µL/min.

Kits

The present disclosure further relates to kits containing the composition of the disclosure. A kit can comprise:

A) a composition comprising an antibody targeting VE-PTP (HPP-β); and

B) a carrier for delivering the composition to a subject.

The kits can be modified to fit the dosing regimen prescribed for the subject being treated. The following is a non-limiting example of a kit for use with a subject receiving a composition of the disclosure by an intraocular injection:

A) an aqueous composition containing:
  a) an antibody targeting the VE-PTP (HPP-β) extracellular domain; and
  b) a carrier system, comprising:
    i) a tonicity agent; and
    ii) water
    wherein the tonicity agent is present in an amount such that the such that the re-constituted formula comprises from about 0.5% to about 10% mass to volume of the tonicity agent; and B) a component for delivering the aqueous composition.

In some embodiments, a kit of the invention comprises:

A) a composition for delivering an anti-VE-PTP antibody; and

B) a composition for delivering an anti-VEGF agent.

The kits can be modified to fit the dosing regimen prescribed for the subject being treated. The following is a non-limiting example of a kit for use with a patient receiving an intravenously-delivered composition comprising the disclosed compounds and an intravitreally-administered anti-VEGF agent. This example provides dosing of the disclosed compounds twice daily for 3 months and for an injection of ranibizumab at week 12.

A. 3 packages, each package containing 4 vials. Each vial comprising a sufficient amount of a VE-PTP (HPP-β) inhibitor to provide 2 daily injections of 5 mg of the disclosed compounds for 7 days; and B. a vial of ranibizumab for injection at the end of week 12 which provides 0.5 mg of ranibizumab.

Kits can comprise any combination of elements. In addition, when an anti-VE-PTP antibody disclosed herein is provided orally, a single container with sufficient doses of the disclosed compounds can be supplied with the kit.

A kit can also provide written instructions for use and disposal of the compositions to be delivered. The instructions can be modified from kit to kit to reflect the dosing regimen prescribed. The instructions can describe any therapy, compounds, excipients, or method of administration described herein.

The disclosed compositions can comprise, for example, from about 1.5% to about 90% mass by volume of a carrier system. Non-limiting examples of tonicity agents include dextrose, mannitol, and glycerin. The formulator can utilize more than one tonicity agent.

The kit can further comprise devices for administration, such as a syringe, filter needle, extension tubing, cannula, and subretinal injector. Non-limiting examples of routes of administration include intraocular, parenteral, and topical. Intraocular routes of administration can include, for example, intravitreal, intracameral, subconjunctival, sub-tenon, retrobulbar, intraocular, posterior juxtascleral, periocular, subretinal, and suprachoroidal. Delivery can be by, for example, syringe, needle, infusion pump, or injector. Syringes and injectors can be, for example, single-dose, multi-dose, fixed-dose, or variable-dose. Non-limiting examples of injectors include, pen injectors, auto-injectors, and electronic patch injector systems.

The kits can comprise suitable components for the administration of a composition of the invention to a subject. In some embodiments a composition of the invention is present in the kit as a unit dosage form. As such, the formulator can provide delivery devices having a higher concentration of compound and adjust the delivered volume to provide an amount of compound that is less than the amount in the entire solution.

A set of instructions can be included in any kit described herein. The instructions can relate to the dosing amount, timing of dosing, reconstitution of the composition when the kit contains a dry composition, and methods of disposal of delivery vehicles and unused composition. The instructions can describe any therapy, compounds, excipients, or method of administration described herein.

Methods

The invention provides compositions and methods for the treatment or prevention of diseases or conditions of the eye, for example, ocular edema, diabetic macular edema, vascular leak, age-related macular degeneration (wet form), age-related macular degeneration (dry form), choroidal neovascularization, diabetic retinopathy, ocular ischemia, uveitis, retinal vein occlusion (central or branch), ocular trauma, surgery induced edema, surgery induced neovascularization, cystoid macular edema, ocular ischemia, and uveitis. These diseases or conditions can be characterized by changes in the ocular vasculature, whether progressive or non-progressive, whether a result of an acute disease or condition, or a chronic disease or condition. These diseases can be characterized by an increased level of plasma vascular endothelial growth factor (VEGF).

The disclosure provides a method of treating ocular neovascularization in a subject in need thereof, the method comprising administering to the subject a therapeutically-effective amount of an antibody targeting VE-PTP (HPTP-β).

In some embodiments, the VE-PTP (HPP-β) inhibitor stabilizes the vasculature against leakage and neovascularization.

Improvement of clinical symptoms can be monitored, for example, by indirect ophthalmoscopy, fundus photography, fluorescein angiopathy, electroretinography, external eye examination, slit lamp biomicroscopy, applanation tonometry, pachymetry, optical coherence tomography, or autorefraction. In some embodiments, the disclosed methods relate to the administration of the VE-PTP (HPP-β) antibody, including compositions comprising an anti-VEGF agent.

In some embodiments, the methods of the disclosure include co-administration of a VE-PTP (HPP-β) antibody with one or more anti-VEGF agents, which can stabilize the vasculature against leakage.

In some embodiments, the methods of the disclosure are drawn towards co-administration of an anti-VE-PTP (HPP- β) antibody with one or more anti-VEGF agents, which can stabilize the vasculature against neovascularization.

In some embodiments, the anti-VE-PTP (HPP-β) antibody can stabilize the vasculature against leakage and neovascularization.

In some embodiments, a human subject with at least one visually-impaired eye is treated with from about 0.1 mg to about 100 mg of a VE-PTP (HPP-β) antibody. Improvement of clinical symptoms can be monitored by, for example, indirect ophthalmoscopy, fundus photography, fluorescein angiopathy, electroretinography, external eye examination, slit lamp biomicroscopy, applanation tonometry, pachymetry, optical coherence tomography and autorefraction. As described herein, the dosing can occur at any frequency determined by the administrator. After cessation of the anti-VEGF agent treatment, subsequent doses can be administered, for example, weekly or monthly, e.g., with a frequency of about 2-8 weeks or about 1-12 months apart depending upon the response.

Diseases that are a direct or indirect result of diabetes include, inter alia, diabetic macular edema and diabetic retinopathy. The ocular vasculature of the diabetic becomes unstable over time and leads to conditions such as non-proliferative retinopathy, macular edema, and proliferative retinopathy. As fluid leaks into the center of the macula, the part of the eye where sharp, straight-ahead vision occurs, the buildup of fluid and the associated protein begin to deposit on or under the macula. This deposit results in swelling that causes the subject's central vision gradually to become distorted. This condition is macular edema. Another condition that can occur is non-proliferative retinopathy in which vascular changes, such as microaneurysms, outside the macular region of the eye can be observed.

These conditions can be associated with diabetic proliferative retinopathy, which is characterized by increased neovascularization. The new blood vessels are fragile and are susceptible to bleeding. The result is scarring of the retina and occlusion or total blockage of the light pathway through the eye due to the overformation of new blood vessels. Subjects having diabetic macular edema often suffer from the non-proliferative stage of diabetic retinopathy; however, subjects often only begin to manifest macular edema at the onset of the proliferative stage.

Diabetic retinopathy is the most common cause of vision loss in working-aged Americans. Severe vision loss occurs due to tractional retinal detachments that complicate retinal neovascularization, but the most common cause of moderate vision loss is diabetic macular edema (DME).

VEGF is a hypoxia-regulated gene, and VEGF levels are increased in hypoxic or ischemic retina. Under most circumstances, Ang2 binds Tie2 but does not stimulate phosphorylation, and acts as a Tie2 antagonist. In the eye, Ang2 is upregulated at sites of neovascularization and acts as a permissive factor for VEGF. Increased expression of VEGF in the retina does not stimulate sprouting of neovascularization from the superficial or intermediate capillary beds of the retina or the choriocapillaris, but does stimulate sprouting from the deep capillary bed where constitutive expression of Ang2 occurs. Co-expression of VEGF and Ang2 at the surface of the retina causes sprouting of neovascularization from the superficial retinal capillaries.

Angiogenesis, the process of creating new blood vessels from pre-existing vessels, is essential to a wide range of physiological and pathological events, including embryological development, menstruation, wound healing, and tumor growth. Most, if not all, tumors require angiogenesis to grow and proliferate. VEGF can be a major factor in angiogenesis by increasing vessel permeability and capillary number.

VEGF is a protein that is primarily found in endothelial cells and has functions in vasculogenesis, angiogenesis, and permeabilization of blood vessels. The expression of VEGF is induced by hypoxia, activated oncogenes, and cytokines. VEGF activation can lead to angiogenesis in normal human cells and tissues, but also angiogenesis in tumors and allows for tumor progression and growth. Inhibition of VEGF can inhibit tumor growth leading to tumor regression. A variety of retinopathies are associated with increased levels of VEGF; ischemia in the eye leads to an induction of VEGF production due to lack of oxygen. This increase in VEGF can cause hyperproliferation of blood vessels in the retina and can lead to blindness. The disclosed anti-VE-PTP (HPP-β) antibodies can act to stabilize ocular vasculature and can counteract the stimulation caused by VEGF and other inflammatory agents present in the diseased retina. In some embodiments, administration of an anti-VE-PTP (HPP-β) antibody to a subject can maintain the level of disease reversal after administration of anti-VEGF drugs to the subject has been withdrawn.

Macular degeneration is characterized by a gradual loss or impairment of eyesight due to cell and tissue degeneration of the yellow macular region in the center of the retina. Macular degeneration is often characterized as one of two types, non-exudative (dry form) or exudative (wet form). Although both types are bilateral and progressive, each type can reflect different pathological processes. The wet form of age-related macular degeneration (AMD) is the most common form of choroidal neovascularization and a leading cause of blindness in the elderly. AMD affects millions of Americans over the age of 60, and is the leading cause of new blindness among the elderly.

Choroidal neovascular membrane (CNVM) is a problem that is related to a wide variety of retinal diseases, but is most commonly linked to age-related macular degeneration. With CNVM, abnormal blood vessels stemming from the choroid (the blood vessel-rich tissue layer just beneath the retina) grow up through the retinal layers. These new vessels are very fragile and break easily, and cause blood and fluid to pool within the layers of the retina.

Diabetes (diabetes mellitus) is a metabolic disease caused by the inability of the pancreas to produce or use insulin. The most common types of diabetes are type 1 diabetes (often referred to as Juvenile Onset Diabetes Mellitus) and type 2 diabetes (often referred to as Adult Onset Diabetes Mellitus). Type 1 diabetes results from the body's failure to produce insulin due to loss of insulin producing cells, and presently requires the person to inject insulin. Type 2 diabetes generally results from insulin resistance, a condition in which cells fail to use insulin properly. Diabetes can be correlated to a large number of other conditions, including conditions or diseases of the eye including diabetic retinopathy and diabetic macular edema (DME).

Diabetic retinopathy is a complication of diabetes that results from damage to the blood vessels of the light-sensitive tissue at the back of the eye (retina). At first, diabetic retinopathy can cause no symptoms or only mild vision problems. Eventually diabetic retinopathy can result in blindness. Diabetic retinopathy can develop in anyone who has type 1 diabetes or type 2 diabetes.

At the earliest stage of non-proliferative retinopathy, microaneurysms occur in the retina's tiny blood vessels. As the disease progresses, more of these blood vessels become damaged or blocked and these areas of the retina send signals into the regional tissue to grow new blood vessels for nourishment. This stage is called proliferative retinopathy. The new blood vessels grow along the retina and along the surface of the clear, vitreous gel that fills the inside of the eye. The vessels have thin, fragile walls and without timely treatment, the new blood vessels can leak blood, for example, whole blood or some constituents thereof, and can result in severe vision loss and even blindness. Also, fluid can leak into the center of the macula, the part of the eye where sharp, straight-ahead vision occurs. The fluid and the associated protein begin to deposit on or under the macula swell the subject's central vision becomes distorted. This condition is called macular edema and can occur at any stage of diabetic retinopathy, but is more likely to occur as the disease progresses.

Uveitis is a condition in which the uvea becomes inflamed. The eye is hollow on the inside with three different layers of tissue surrounding a central cavity. The outermost is the sclera (white coat of the eye) and the innermost is the retina. The middle layer between the sclera and the retina is called the uvea. The uvea contains many of the blood vessels that nourish the eye. Complications of uveitis include glaucoma, cataracts, and new blood vessel formation (neovascularization).

Ocular trauma is any sort of physical or chemical injury to the eye. Ocular trauma can affect anyone and major symptoms include redness or pain in the affected eye. The symptoms tend not to occur if tiny projectiles cause the trauma.

Surgery-induced edema is the development of swelling in the eye tissues following surgery on the retina or other part of the eye. Cystoid macular edema (CME) is an example of this phenomenon. CME can occur not only in people who have had cataract surgery, but also those with diabetes, retinitis pigmentosa, AMD, or conditions that cause chronic inflammation in the eye. The major symptoms of CME are blurred or decreased central vision.

Ocular ischemic syndrome (OIS) encompasses the signs and symptoms that result from chronic vascular insufficiency. The condition is caused by ocular hypoperfusion due to occlusion or stenosis of the common or internal carotid arteries. OIS generally affects subjects of age 50-80, who often exhibit systemic diseases, such as hypertension or diabetes. The major symptoms of OIS are orbital pain, vision loss, changes of the visual field, asymmetric cataract, and sluggish reaction to light.

Retinal vein occlusion (RVO) is the most common retinal vascular disease after diabetic retinopathy. Depending on the area of retinal venous drainage effectively occluded, the condition is broadly classified as central retinal vein occlusion (CRVO), hemispheric retinal vein occlusion (HRVO), or branch retinal vein occlusion (BRVO). Presentation of RVO is with variable painless visual loss with any combination of fundal findings consisting of retinal vascular tortuosity, retinal hemorrhages (blot and flame shaped), cotton wool spots, optic disc swelling and macular edema. In a CRVO, retinal hemorrhages can be found in all four quadrants of the fundus, while the hemorrhages are restricted to either the superior or inferior fundal hemisphere in a HRVO. In a BRVO, hemorrhages are largely localized to the area drained by the occluded branch retinal vein. Vision loss occurs secondary to macular edema or ischemia.

Compositions of the disclosure act to stabilize ocular vasculature and, in some embodiments, an agent of the disclosure can counteract the stimulation caused by VEGF and other inflammatory agents that can be present in the diseased retina. In some embodiments, administration of an antibody of the disclosure to a subject can be used to maintain the level of disease reversal after administration of anti-VEGF drugs to the subject has been withdrawn.

Treatment of Subjects

In some embodiments, a single administration of the composition of the disclosure in a subject having a disease or condition as disclosed herein results in sustained intraocular expression of a VE-PTP (HPP-β) inhibitor at a level sufficient for long-term suppression of ocular neovascularization.

For example, the level of VE-PTP (HPP-β) inhibitor produced in a host ocular cell can be at least 100 pg/mL, at least 200 pg/mL, at least 300 pg/mL, at least 400 pg/mL, at least 500 pg/mL, at least 600 pg/mL, at least 00 pg/mL, at least 800 pg/mL, at least 900 pg/mL, at least 1000 pg/mL, at least 2000 pg/mL, at least 3000 pg/mL, at least 4000 pg/mL, at least 5000 pg/mL, at least 6000 pg/mL, at least 7000 pg/mL, at least 8000 pg/mL, at least 9000 pg/mL or at least 10,000 pg/mL. The level of VE-PTP (HPTP-β) inhibitor produced in host ocular cell can be at most 100 pg/mL, at most 200 pg/mL, at most 300 pg/mL, at most 400 pg/mL, at most 500 pg/mL, at most 600 pg/mL, at most 700 pg/mL, at most 800 pg/mL, at most 900 pg/mL, at most 1000 pg/mL, at most 2000 pg/mL, at most 3000 pg/mL, at most 4000 pg/mL, at most 5000 pg/mL, at most 6000 pg/mL, at most 7000 pg/mL, at most 8000 pg/mL, at most 9000 pg/mL, or at most 10,000 pg/mL.

Protein levels can be measured at least about 0.1, at least about 0.2, at least about 0.3, at least about 0.4, at least about 0.5, at least about 0.6, at least about 0.7, at least about 0.8, at least about 0.9, at least about 1, at least about 2, at least about 3, at least about 4, at least about 5, at least about 6, at least about 7, at least about 14, at least about 21, at least about 30, at least about 50, at least about 75, at least about 100, at least about 125, at least about 150, at least about 175, at least about 200, at least about 225, at least about 250, at least about 275, at least about 300, at least about 325, at least about 350, or at least about 365 days after administering a pharmaceutical composition of the disclosure. Protein levels can be measured at most about 0.1, at most about 0.2, at most about 0.3, at most about 0.4, at most about 0.5, at most about 0.6, at most about 0.7, at most about 0.8, at most about 0.9, at most about 1, at most about 2, at most about 3, at most about 4, at most about 5, at most about 6, at most about 7, at most about 14, at most about 21, at most about 30, at most about 50, at most about 75, at most about 100, at most about 125, at most about 150, at most about 175, at most about 200, at most about 225, at most about 250, at most about 275, at most about 300, at most about 325, at most about 350, or at most about 365 days after administering a pharmaceutical composition of the disclosure.

Central Foveal Thickness

Also disclosed herein are methods for decreasing the Central Foveal Thickness (CFT) in a subject having a disease or condition as disclosed herein. The method comprises administering to an eye an antibody targeting VE-PTP (HPP-β), wherein the administration of the antibody can be conducted in any manner.

The level of decrease in Central Foveal Thickness can be for example, from about 50 µm to about 1000 µm. The level of decrease in Central Foveal Thickness can be for example, from about 50 µm to about 500 µm, from about 50 µm to about 750 µm, from about 150 µm to about 500 µrom about 200 µm to about 500 µm, from about 200 µm to about 1000 µm, from about 250 µm to about 650 µm, or from about 400 µm to about 700 µm.

Visual Auity

Further disclosed herein are methods for increasing the visual acuity of a subject having a disease or condition as disclosed herein.

Visual acuity is acuteness or clearness of vision, which depends on the sharpness of the retinal focus within the eye and the sensitivity of the interpretative faculty of the brain. Visual acuity is a measure of the spatial resolution of the visual processing system. Visual acuity is tested by requiring the subject to identify characters, typically numbers or letters, on a chart from a set distance. Chart characters are represented as black symbols against a white background. The distance between the subject's eyes and the testing chart is set at a sufficient distance to approximate infinity in the way the lens attempts to focus. Twenty feet, or six meters, is essentially infinity from an optical perspective. In the present disclosure, an improvement in visual acuity was assessed by an increase in the number of letters that can be read from the chart.

One non-limiting test for measuring visual acuity is the use of the ESV-3000 ETDRS testing device and self-calibrated test lighting. The ESV-3000 device incorporates LED light source technology. The auto-calibration circuitry constantly monitors the LED light source and calibrates the test luminance to 85 $cd/m^2$ or 3 $cd/m^2$.

Although designed for clinical trials, where large-format ETDRS testing (up to 20/200) is performed at 4 meters, the device can be used in a non-research setting, i.e., hospital or clinic where ocular disease monitoring is conducted. To evaluate ETDRS properly, the test should be conducted under standardized lighting conditions, for example, photopic test level of 85 $cd/m^2$. Scoring of visual acuity can be accomplished in any manner chosen by the monitor. After providing a baseline evaluation, the increase or decrease in the number of letters that can be identified by the test subject provides a measure of sight increase or decrease during treatment.

Disclosed herein is a method for increasing visual acuity in a subject having a disease or condition of the eye disclosed herein. This method comprises administering to a subject having the disease or condition of the eye, an antibody targeting VE-PTP (HPP-β), wherein the administration of the antibody can be conducted in any manner described herein. The increase in the number of letters recognized by a treated eye can be, for example, from about 1 to about 30 letters, from about 5 to about 25 letters, from about 5 to about 20 letters, from about 5 to about 15 letters, from about 5 to about 10 letters, from about 10 to about 25 letters, from about 15 to about 25 letters, or from about 20 to about 25 letters. The increase in visual acuity can be about 1 letter, about 5 letters, about 10 letters, about 15 letters, about 20 letters, or about 25 letters.

EXAMPLES

Example 1

Figure 4:
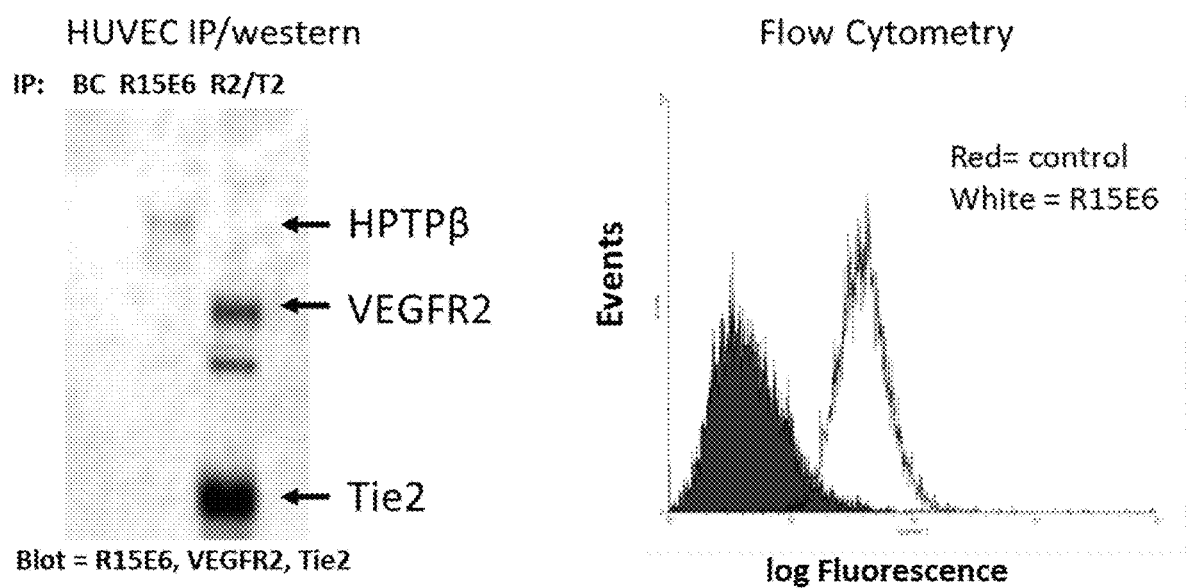
FIG. 4 illustrates an immunoprecipitation western blot (left panel) and flow cytometry results (right panel) of R15E6 bound to endogenous human VE-PTP (HPTP-β) in human endothelial cells.

Generation of Monoclonal Antibodies to the VE-PTP (HPTP-β) Extracellular Domain Using Hybridoma Technology Hybridoma technology was used to generate monoclonal antibodies against the N-terminal extracellular domain (ECD) of human VE-PTP (HPP-β) or mouse VE-PTP as shown in the schematic of FIG. 3. Mice were challenged with human VE-PTP (HPP-β) ECD protein to generate antibodies against the target protein. B-cells were then harvested from the spleen and lymph nodes and fused with myeloma cells to produce the hybridoma cell line. The fused cells were cultured in a medium where only myeloma cells that have genes derived from the antigen exposed mouse can grow. Colonies that were derived from a single myeloma cell were generated by limiting dilution. Antibodies produced by the hybridoma colonies were then screened for binding to human VE-PTP (HPP-β) ECD by ELISA. One hybridoma, R15E6, was selected for further analysis. R15E6 antibody bound to endogenous human VE-PTP (HPP-β) from human umbilical vein endothelial cells (HUVECs) as shown by immunoprecipitation (IP) western blot (left panel) and flow cytometry (right panel) in FIG. 4. No binding of R15E6 to the bead control (protein A/G beads without antibody; BC) or VEGFR2 or Tie2 (R2/T2) was observed.

Example 2

Tie2 Activation in HUVECS with R15E6

Figure 6:
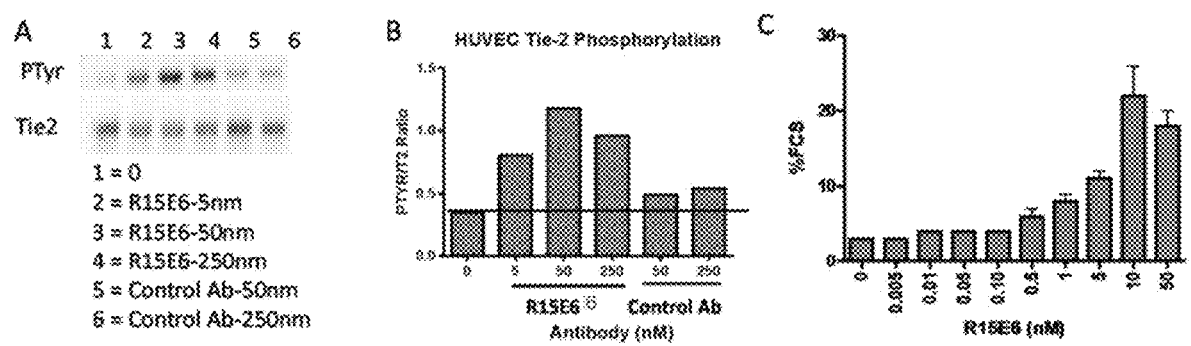
FIG. 6 illustrates a western blot (panel A) and quantification (panel B) of concentration-dependent phosphorylation of Tie2 and enhanced endothelial cell viability (panel C) by R15E6.

R15E6 activated Tie2 in a concentration-dependent manner as demonstrated by IP experiments shown in panels A and B of FIG. 6. The antibody also enhanced the viability of serum starved endothelial cells in a concentration-dependent manner in HUVECs as shown in panel C.

Example 3

Tie2 Activation and Cellular Permeability Experiments with Murine Monoclonal and Polyclonal Anti-Mouse VE-PTP ECD Antibodies To characterize therapeutic effects of a VE-PTP antibody in vitro, Tie2 activation and cellular permeability experiments were performed using anti-mouse VE-PTP antibodies. Monoclonal and polyclonal antibodies against mouse VE-PTP ECD were generated by immunizing rats with a VE-PTP-Fc fusion protein of the N-terminal 8 FN3 repeats of the extracellular domain. Immunization, hybridoma-fusion, and screening were performed as described above. In Example 3, monoclonal antibody 109.1 (mAb 109.1) and polyclonal antibodies (pAbs) against the extracellular fibronectin type III (FN3)-like domains 1-8 of mouse VE-PTP were selected for further analysis.

Figure 7:
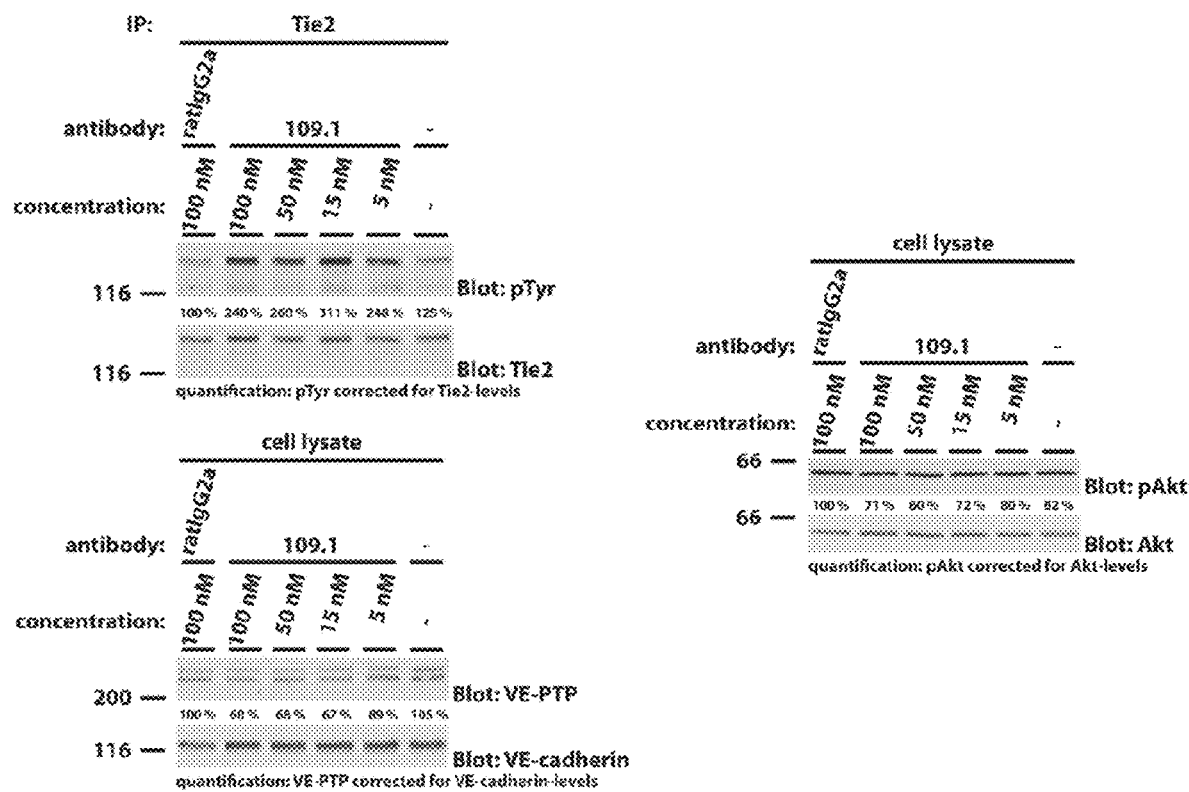
FIG. 7 illustrates effects of rat anti-mouse VE-PTP monoclonal antibody 109.1 on Tie2 (top left panel), mouse VE-PTP expression (bottom left panel), and Akt (right panel) in mouse endothelial cells as determined by western blot.

FIG. 7 illustrates the effect of mAb 109.1 on Tie2 activation (top left panel), mouse VE-PTP protein expression (bottom left panel), and Akt (right panel) in mouse endothelial cells (bEnd) as determined by western blot. Treatment with mAb 109.1 resulted in the activation of Tie2 as indicated by Tie2 phosphorylation (pTyr; top left panel). Akt was constitutively activated in the tested mouse endothelial cells as confirmed by the absence of increased phosphorylation with increasing concentrations of antibody (right panel).

Figure 8:
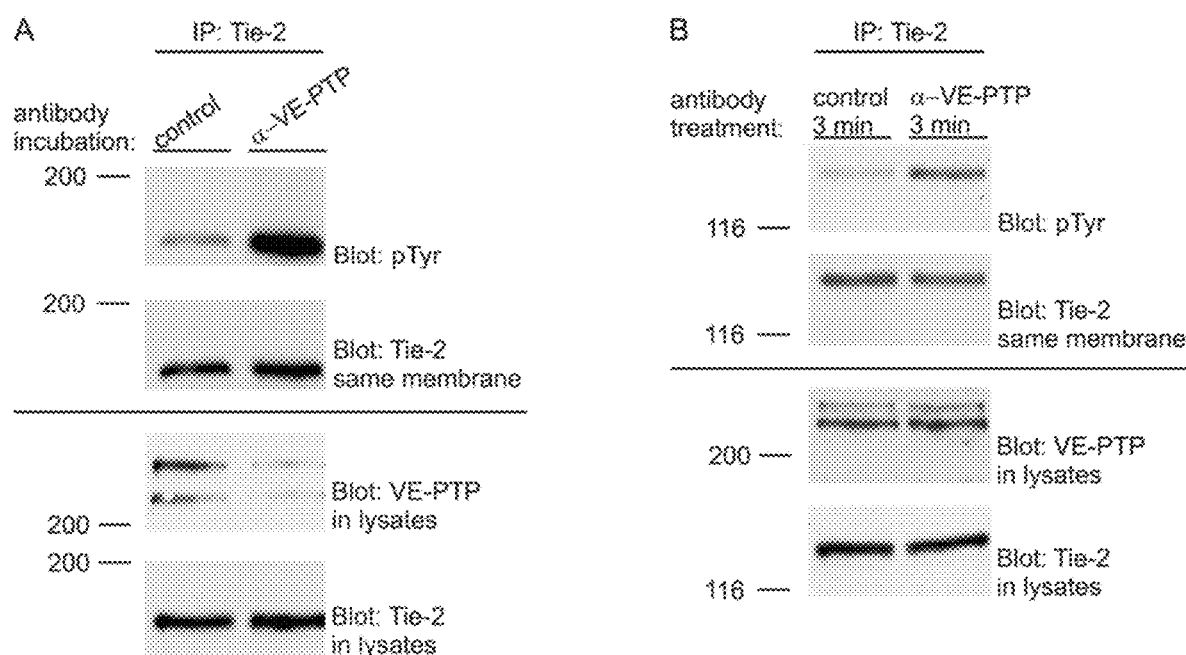
FIG. 8 illustrates Tie2 activation by polyclonal antibodies against mouse VE-PTP ECD after 1 hour of incubation (panel A) and 3 min of incubation (panel B) in mouse endothelial cells.

In vitro experiments with mouse pAb 1-8 also enhanced Tie2 (Tie-2) activation and downstream signaling in endothelial cells. Cultured mouse endothelial (bEnd.5) cells were treated with pAb 1-8 or preimmune (control) antibodies for 1 hr and subsequently immunoprecipitated for Tie2, followed by immunoblotting with anti-phosphotyrosine antibodies (pTyr) and antibodies against Tie2. Aliquots of cell lysates with identical protein content were directly immunoblotted for VE-PTP and Tie2 (bottom panels). FIG. 8 illustrates the immunoprecipitation experiments in which pAbs rapidly induced Tie2 activation in bEnd.5 cells treated with polyclonal antibodies against mouse VE-PTP or preimmune antibodies for 1 h (panel A) and 3 min (panel B).

Figure 9:
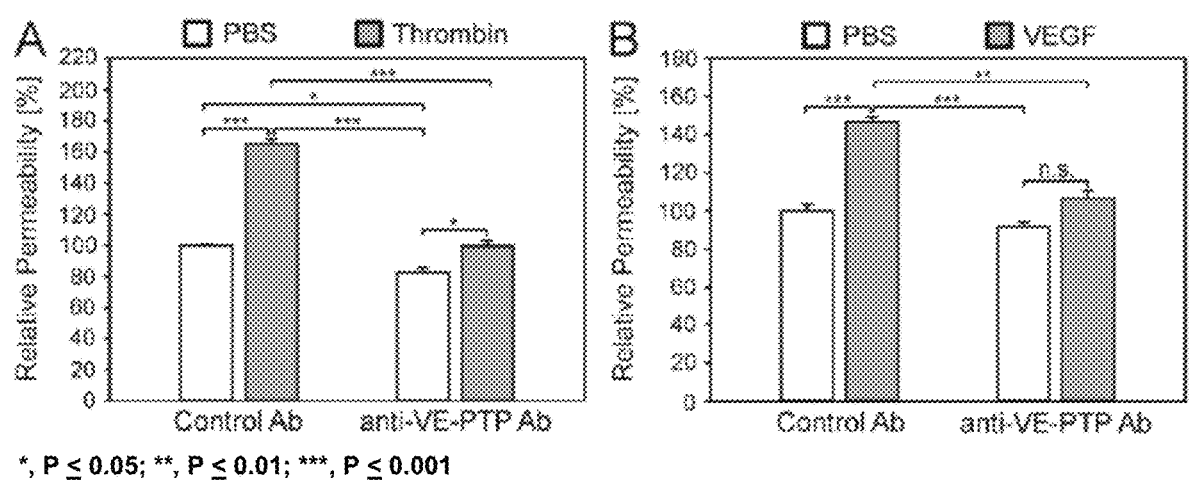
FIG. 9 illustrates in vitro inhibition of thrombin- and VEGF-induced endothelial cell permeability by mouse VE-PTP ECD polyclonal antibodies.

Consistent with the vascular-stabilizing effects of Tie2 activation, VE-PTP ECD antibodies reduced thrombin- and VEGF-induced permeability of endothelial monolayers in vitro as shown in FIG. 9. Paracellular permeability for 250 kD FITC-dextran was determined for cultured HUVEC monolayers grown in transwell filters. Permeability was induced either with thrombin (panel A) or VEGF (panel B). Permeability of PBS-treated cells was set to 100%. For VE-PTP targeting, cells were treated with anti-VE-PTP pAbs. As a control, cells were treated with preimmune antibodies (control Ab). The data represent two independent experiments.

Figure 10:
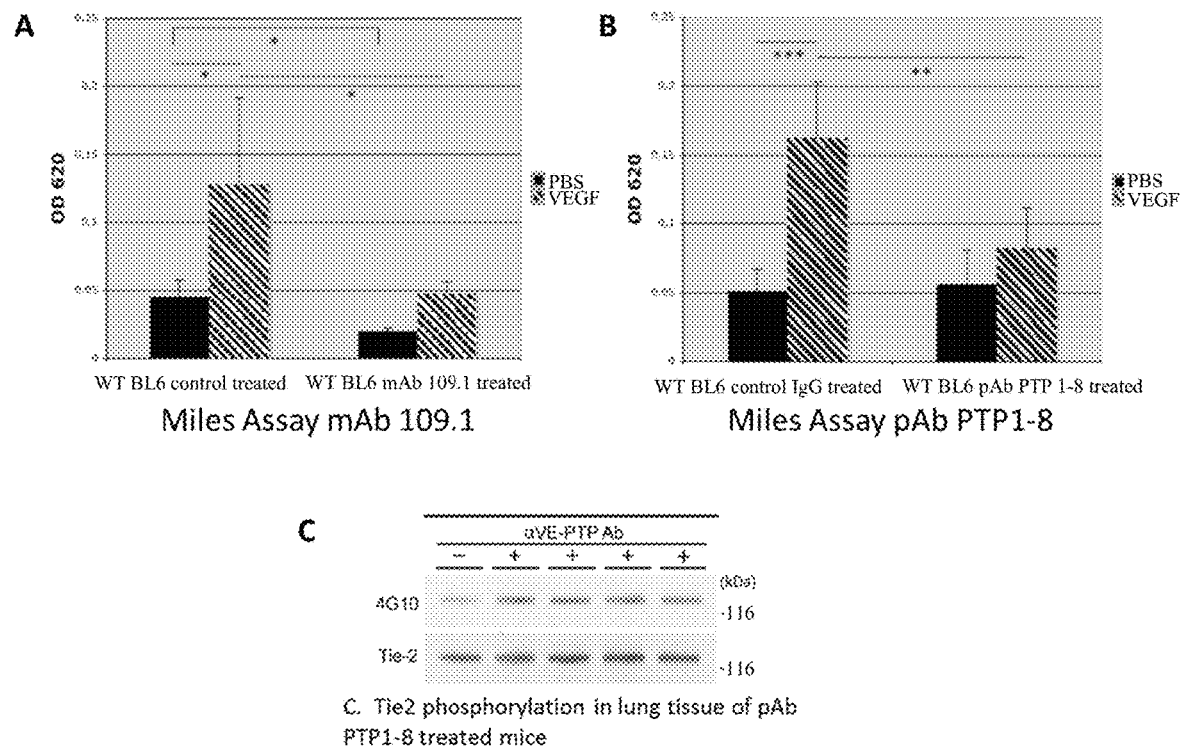
FIG. 10 illustrates in vivo inhibition of VEGF-induced cutaneous vascular permeability by intravenous administration of monoclonal antibody 109.1 (panel A) and mouse VE-PTP ECD polyclonal antibodies (PTP1-8) (panel B), and immunoprecipitation of Tie2 from lung lysates of control IgG (−) or anti-VE-PTP antibody-injected mice (+) (panel C).

Consistent with the vascular-stabilizing effects of Tie2 activation, VE-PTP ECD antibodies also blocked VEGF-induced cutaneous vascular permeability in vivo as shown in FIG. 10. Both monoclonal and polyclonal VE-PTP ECD antibodies, mAb 109.1 (panel A) and pAb PTP 1-8 (panel B), inhibited VEGF-induced cutaneous vascular permeability as demonstrated by the Miles assay. The Miles assay can be used as an in vivo model of vascular permeability, which is characteristic of vascular leakage and neovascularization. Mice were injected intravenously with 100 μg of control IgG or anti-mouse VE-PTP antibodies 30 min before starting the Miles assay. Evan's blue was then injected to the mice intravenously, followed by intradermal injection of VEGF (striped bars) or PBS (solid black bars) after 10 min. After 30 min, the mice were sacrificed and the dye was extracted from the skin samples and quantified. Data sets were checked for normality and equal variance. Values are presented as means±standard error of mean (SEM). As shown in panel C, the blockade of permeability correlates with Tie2 phosphorylation as demonstrated in lung tissue of mice treated with pAb PTP 1-8.

Example 4

Figure 11:
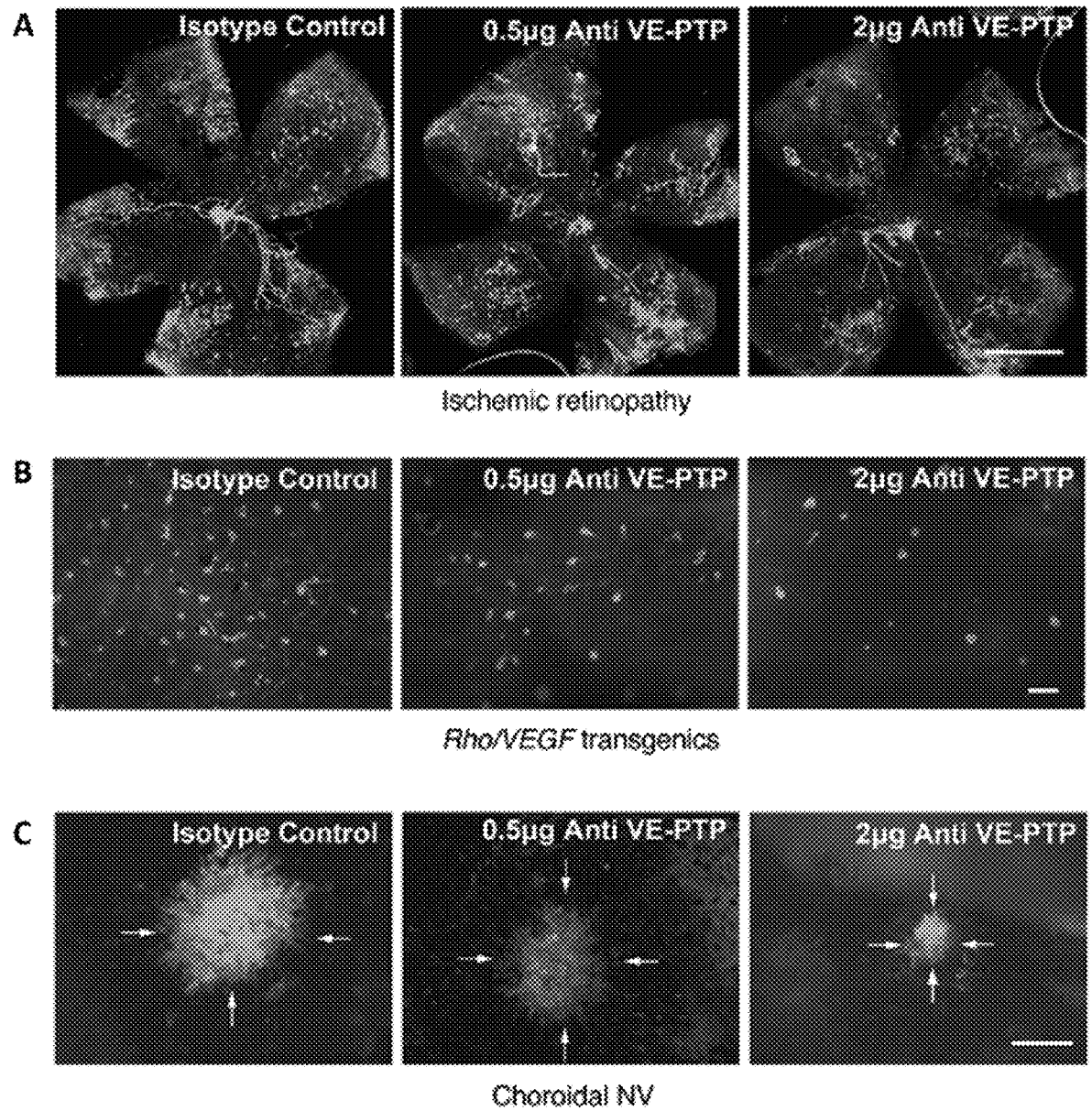
FIG. 11 depicts effects on retinal neovascularization (panels A and B) and choroidal neovascularization (panel C) after intraocular administration of anti-mouse VE-PTP monoclonal antibody 109.1.
Figure 12:
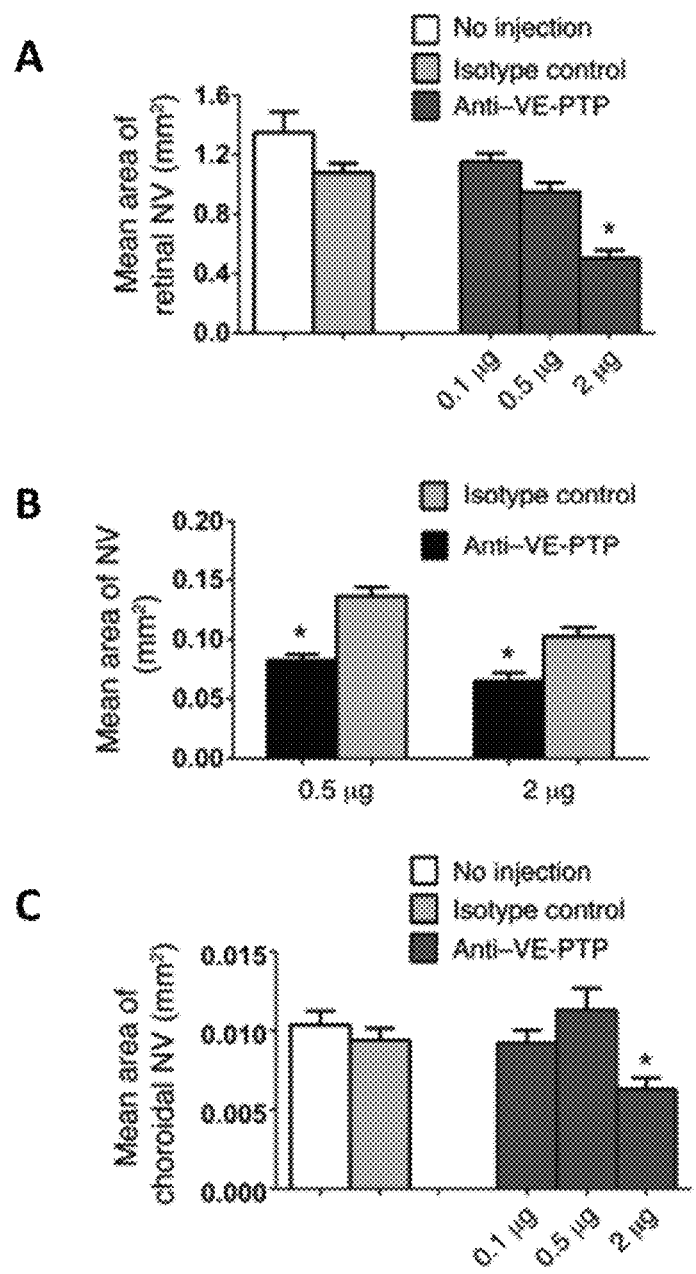
FIG. 12 shows quantification of the mean area of retinal neovascularization (panels A and B) and choroidal neovascularization (panel C) after intraocular administration of an anti-mouse VE-PTP monoclonal antibody 109.1.
Figure 14:
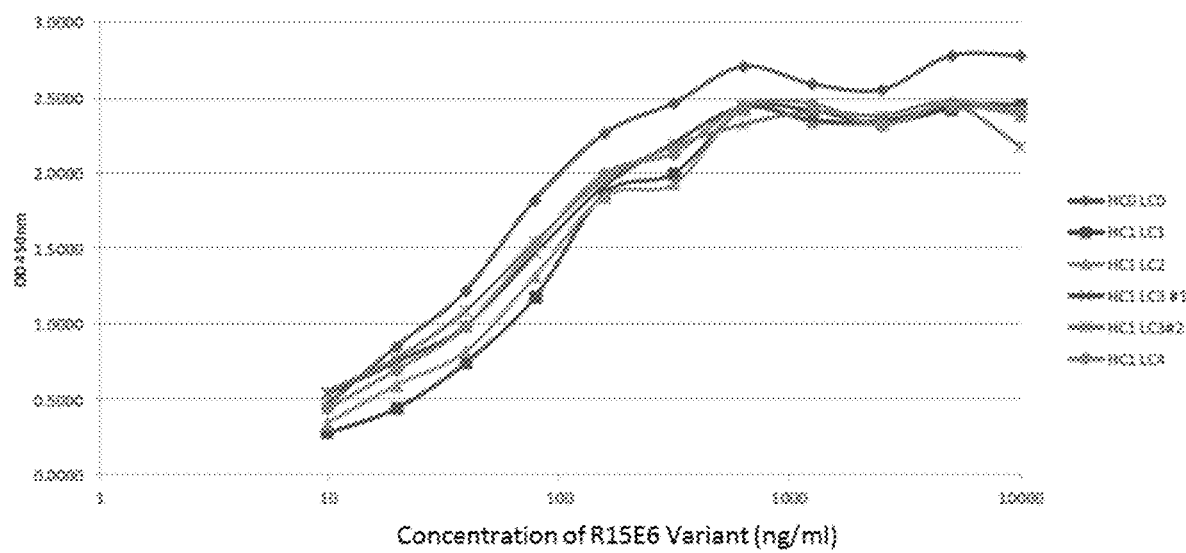
FIG. 14 illustrates binding of HC1 variants of R15E6 and HCOLCO to HPTP-β.
Figure 15:
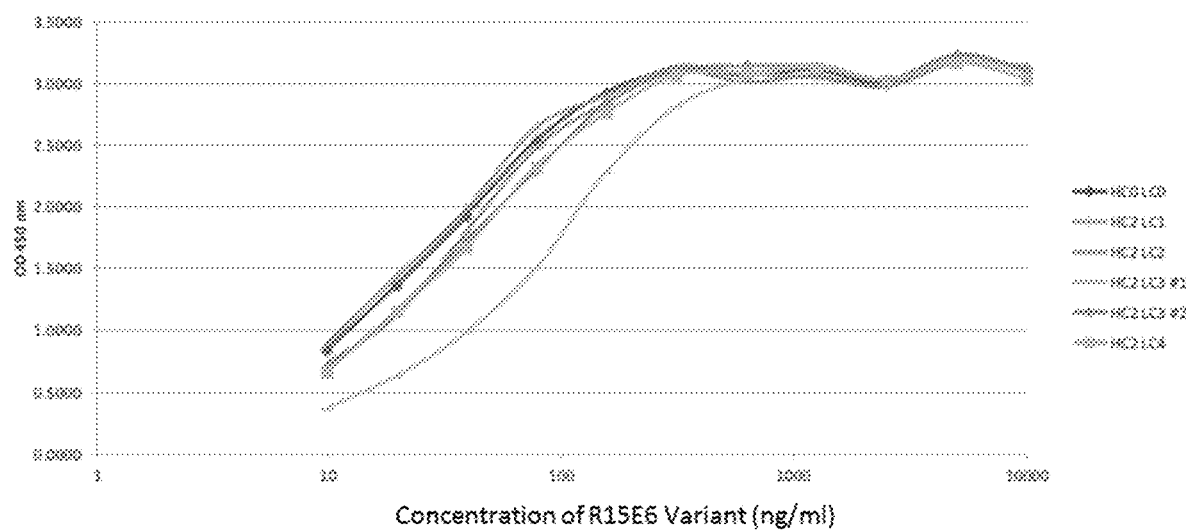
FIG. 15 illustrates binding of HC2 variants of R15E6 and HCOLCO to HPTP-β
Figure 16:
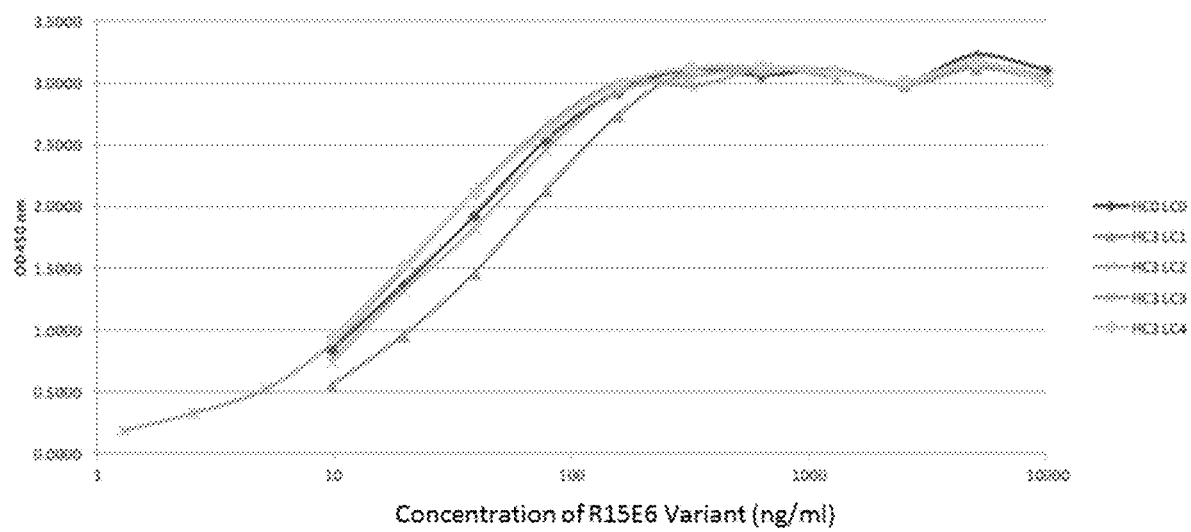
FIG. 16 illustrates binding of HC3 variants of R15E6 and HCOLCO to HPTP-β.

Effects of a Mouse VE-PTP ECD Monoclonal Antibody on Retinal and Choroidal Neovascularization in Mice In an ischemic retinopathy model that mimics the aspects of proliferative diabetic retinopathy, a VE-PTP ECD monoclonal antibody (mAb 109.1) significantly reduced retinal neovascularization after administration of the antibody as shown in FIG. 11 (panel A) and quantified in FIG. 12 (panel A). At P12, mice with ischemic retinopathy were administered an intravitreous injection of 0.1, 0.5, or 2 μg of mAb 109.1 or 2 μg IgG isotype control (n≥12 for each). At P17, extensive GSA-stained retinal neovascularization was observed in control IgG-injected eyes and significantly less retinal neovascularization was observed in eyes injected with 2 μg anti-VE-PTP. *P<0.001.

Similarly, in two models that mimic different aspects of wet age-related macular edema (retinal angiomatous proliferation and choroidal neovascularization), a single 2 μg intravitreal administration of the VE-PTP ECD monoclonal antibody (mAb 109.1) significantly reduced both retinal neovascularization (panel B of FIG. 11 and quantified in panel B of FIG. 12). At P15, six Rho-VEGF transgenic mice were given an intravitreous injection of 0.5 or 2 of mAb 109.1 in one eye and a corresponding dose of control IgG in the fellow eye. At P21, significantly less GSA-stained subretinal neovascularization was observed in the eyes treated with 0.5 or 2 μg of mAb 109.1 than in the control IgG-treated eyes. *P=0.01 by unpaired t-test for comparison with IgG control fellow eyes. Scale bar: 100 μm.

Intravitreous injection of 2 μg of mAb 109.1 significantly reduced the area of choroidal neovascularization at Bruch's membrane rupture sites compared with control IgG (panel C of FIG. 11 and quantified in panel C of FIG. 12). *P<0.001 by 1-way ANOVA with Bonferroni's correction. Scale bar: 100 μm.

Figure 25:
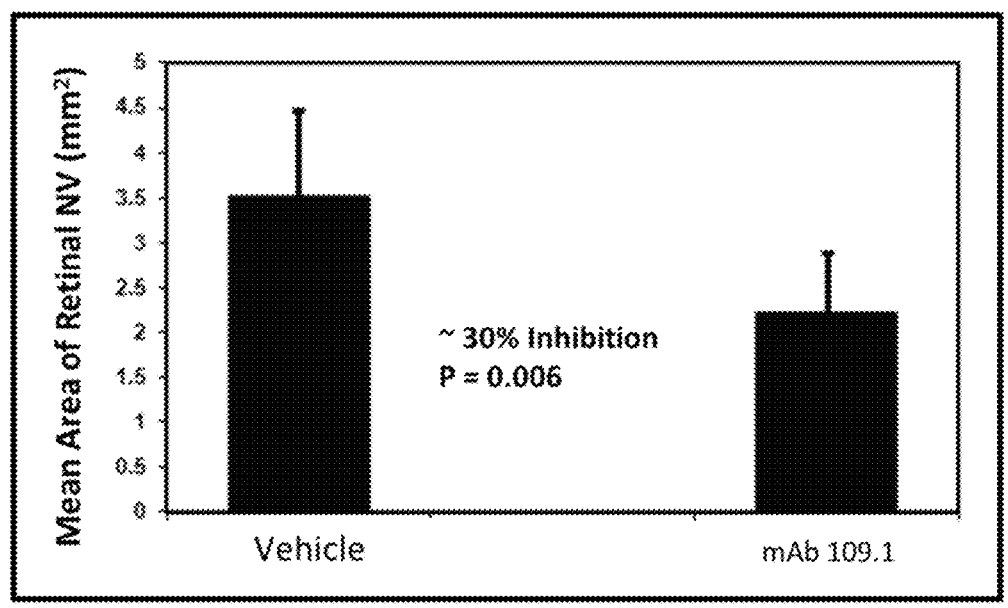
FIG. 25 illustrates that subcutaneous administration of monoclonal antibody 109.1 reduced ischemic neovascularization in mice compared to vehicle.

Subcutaneous administration of mAb 109.1 also reduced ischemic neovascularization in an ischemic retinopathy mouse model. The mean area of retinal neovascularization was reduced by about 30% compared to vehicle, as shown in FIG. 25. Mice with ischemic retinopathy were administered a subcutaneous injection of 2 mg/kg q.o.d. (every other day) x3.

Example 5

Figure 24:
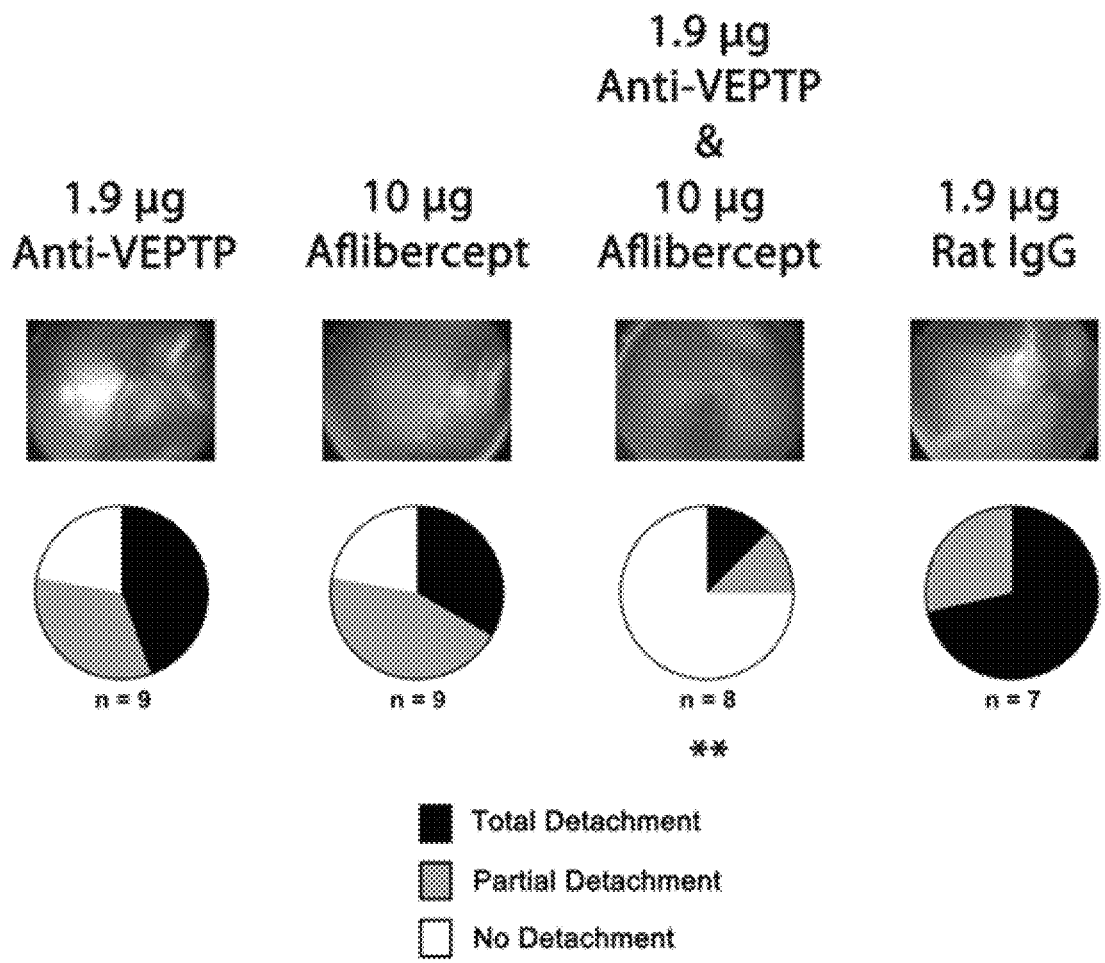
FIG. 24 illustrates enhanced efficacy of an anti-mouse VE-PTP antibody/aflibercept combination therapy for the treatment of retinal detachment in a mouse model.

Effects of a Mouse VE-PTP ECD Monoclonal Antibody in Combination with an Anti-VEGF Agent on Retinal Detachment in Mice To evaluate the effects of combination therapies using an anti-VE-PTP antibody disclosed herein, a Tet/opsin/VEGF mouse model was used. Tet/opsin/VEGF transgenic mice develop severe subretinal neovascularization and vascular leakage, and leads to exudative retinal detachment mediated by inducible retinal overexpression of human VEGF. FIG. 24 shows enhanced efficacy of the combination of an anti-mouse VE-PTP antibody (mAb 109.1) and aflibercept compared to either therapy alone to prevent retinal detachment in the mice, as denoted by the double asterisks. Rat IgG was used as the control.

Example 6

Generation and Purification of Humanized Antibodies from R15E6 Against Human VE-PTP (HPTP-β)

R15E6 is a 150 kDa antibody containing heavy chains and light chains. Sixteen different humanized variations of the antibody were synthesized using different combinations of heavy chain sequence to light chain sequences as shown in TABLE 12.

R15E6 humanized variants, as described in Example 1, were cloned into the pVitro DHFR3 mammalian expression vector. Medium-scale transient transfection expression analysis was carried out to determine expression yield from CHO cells. Suspension-adapted CHO cells were cultivated at $2.0$-$3.0 \times 10^5$ cells/mL with 85% $CO_2$ at 37° C. at 150 rpm in Pro CHO4 serum-free medium supplemented with 8 mM L-glutamine and 10 mL/L hypoxanthine/thymidine in 500 mL vented flasks. Maxi-preps of each construct were prepared using a Nucleobond pc500 kit according to manufacturer instructions. Vector DNA was quantified using a NanoDrop Lite™ spectrophotometer.

100 mL of cells at a final density of $1.0 \times 10^6$ cells/mL were transiently transfected with 1.25 μg/mL of plasmid DNA in Pro CHO5 serum-free medium supplemented with 8 mM L-glutamine and 10 mL/L hypoxanthine/thymidine in 500 mL vented flasks. Transfected cultures were incubated for 8 to 11 days with 85% $CO_2$ at 37° C. at 150 rpm before harvesting by centrifugation at 4,000 rpm at 4° C. for 40 min.

Following centrifugation, the media were filtered through a 0.8 μm cellulose acetate filter. Each batch was purified using an Amersham Biosciences AKTA chromatography system. Expressed humanized antibodies were purified via Protein A affinity chromatography. A 1-mL HiTrap Protein A column was used for all humanized antibody purifications. All purifications were carried out using Fusion Antibodies in-house wash and elution buffers. After loading of the protein into the column, any bound antibody was eluted using a glycine/Tris buffer (pH 3). All eluted 1 mL fractions were neutralized with 100 µL Tris buffer (pH 8.5). Eluted fractions corresponding to the elution peak were selected for overnight dialysis in PBS. Following dialysis, the concentration of the antibody was measured with a NanoDrop Lite™ spectrophotometer.

Example 7

Evaluation of Humanized Antibodies Against Human VE-PTP (HPTP-β)

Samples of the humanized antibodies were analyzed by reducing and non-reducing SDS-PAGE (FIG. 13) to determine the presence of heavy and light chains and the purity of the antibodies. The mouse/human chimeric antibody, HC0LC0, was derived from R15E6 by fusion of the murine heavy and light chain variable regions to the human Fc region. In both SDS-PAGE gels, lane 1: SeeBlue Plus2 pre-stained protein standard; lane 2: HC0LC0 #1; lane 3: HC1LC1 #2; lane 4: HC1LC2 #1; lane 5: HC1LC3 #1; lane 6: HC1LC3 #2; lane 7: HC1LC4 #1; lane 8: HC2LC1 #1; lane 9: HC2LC2 #1; lane 10: HC2LC3 #1; lane 11: HC2LC3 #2; lane 12: HC2LC4 #1; lane 13: HC3LC1 #1; lane 14: HC3LC2 #1; lane 15: HC3LC3 #1; lane 16: HC3LC4 #1; lane 17: HC4LC1 #1; lane 18: HC4LC1 #2; lane 19: HC4LC2 #1; lane 20: HC4LC3 #1; lane 21: HC4LC3 #2; lane 22: HC4LC4 #1; lane 23: HC4LC4 #2; and lane 24: SeeBlue Plus2 pre-stained protein standard. The SDS-PAGE gel analysis showed high purity of all analyzed samples. In the reducing SDS-PAGE, the heavy and light chains are visible and are at the expected molecular weight of 50 kDa for the heavy chain and 25 kDa for the light chain. In the non-reducing SDS-PAGE, no free heavy or light chains were observed at around 50 kDa or 25 kDa, respectively. The gels show a low amount of protein for all HC4 variants and HC1LC3, HC2LC3, and HC3LC3 variants.

Purified R15E6 was quantified using the extinction coefficient of 13.7 as the standard reference for IgG at 280 nm using a NanoDrop Lite™ spectrophotometer. TABLE 16 summarizes the results of the SDS-PAGE analysis. In agreement with the SDS-PAGE analysis, all of the heavy chain 4 variants expressed little to no antibody.

TABLE 16

| R15E6 Variant | Volume | Concentration (mg/ml) | Total yield (mg) | SDS PAGE |
|---|---|---|---|---|
| HC0 LC0 #1 | 100 ml | 0.403 | 0.85 | HC and LC present |
| HC1 LC1 #1 | | 0 | 0 | No antibody purified |
| HC1 LC1 #2 | 160 ml | 0.141 | 0.28 | HC and LC present |
| HC1 LC2 #1 | 100 ml | 0.127 | 0.23 | HC and LC present |
| HC1 LC3 #1 | 100 ml | 0.045 | 0.086 | HC and LC present faint |
| HC1 LC3 #2 | 160 ml | 0.175 | 0.39 | HC and LC present |
| HC1 LC4 #1 | 100 ml | 0.1 | 0.18 | HC and LC present |
| HC2 LC1 #1 | 100 ml | 0.147 | 0.28 | HC and LC present |
| HC2 LC2 #1 | 100 ml | 0.538 | 1.08 | HC and LC present |
| HC2 LC3 #1 | 100 ml | 0.034 | 0.068 | HC and LC present faint |
| HC2 LC3 #2 | 160 ml | 0.591 | 1.18 | HC and LC present |
| HC2 LC4 #1 | 100 ml | 0.165 | 0.39 | HC and LC present |
| HC3 LC1 #1 | 100 ml | 0.078 | 0.16 | HC and LC present |
| HC3 LC2 #1 | 100 ml | 0.264 | 0.53 | HC and LC present |
| HC3 LC3 #1 | 100 ml | 0.043 | 0.07 | HC and LC very faint |
| HC3 LC4 #1 | 100 ml | 0.406 | 0.812 | HC and LC present |
| HC4 LC1 #1 | 100 ml | 0.025 | 0.06 | No bands |
| HC4 LC1 #2 | 160 ml | 0.051 | 0.11 | No bands |
| HC4 LC2 #1 | 100 ml | 0.051 | 0.11 | No bands |
| HC4 LC3 #1 | 100 ml | 0.053 | 0.13 | No bands |
| HC4 LC3 #2 | 160 ml | 0.035 | 0.07 | No bands |
| HC4 LC4 #1 | 100 ml | 0.041 | 0.09 | No bands |
| HC4 LC4 #2s | 160 ml | 0.031 | 0.068 | No bands |

Example 8

Selectivity of R15E6 and Humanized Variants Against Human VE-PTP (HPTP-β), Cynomologus VE-PTP (cyno PTP-β), and Human HPTP-η

Tissue culture supernatants containing the antibodies from hybridomas were tested against targets human VE-PTP (Human Beta ½ ECD), cyno VE-PTP (Cyno Beta), and human HPTP-η (Human Eta) to determine binding affinity by ELISA.

Human HPTP-β, cyno PTPβ, and human HPTP-η were independently produced and purified using HEK293 cells. The HEK293 cells were seeded in a shaker flask for 24 hrs before transfection with plasmids expressing species-specific VE-PTP or HPTP-η. The HEK293 cells were grown using serum-free chemically defined media. The DNA for the species-specific VE-PTP or HPTP-η construct was transiently transfected into a 30 mL suspension of HEK293. After 24 hrs, the cells were counted to assess the viability of the cells and determine the viable cell count. Additional readings were taken throughout the transient transfection process. The cell culture was harvested at day 5 of the transient transfection. The conditioned media supernatant harvested from the transient transfection was clarified by centrifugation. The supernatant was filtered using a 0.2 µm membrane filter. The protein was then purified by anti-His tag affinity chromatography. After purification, buffer exchange of the protein to PBS (pH 7.4) was performed. Then, SDS-Gel Capillary Electrophoresis (CE-SDS) analysis was performed and the protein was purified. The amino acid sequences of the DNA plasmid inserts, the DNA plasmid inserts, and corresponding wildtype sequences are shown in TABLE 15 below. The signal peptide of the protein sequences is underlined.

TABLE 15

| SEQ ID NO: | Name | Sequence |
|---|---|---|
| 38 | Protein sequence of Human VE-PTP (HPTP-β) containing first eight FN3 repeats with C-terminal His$_6$ tag (SEQ ID NO: 52) (Human ½ VE-PTP ECD) | MEWSWVFLFFLSVTTGVHSEPERCNFTL AESKASSHSVSIQWRILGSPCNFSLIYS SDTLGAALCPTFRIDNTTYGCNLQDLQA GTIYNFKIISLDEERTVVLQTDPLPPAR FGVSKEKTTSTGLHVWWTPSSGKVTSYE VQLFDENNQKIQGVQIQESTSWNEYTFF NLTAGSKYNIAITAVSGGKRSFSVYTNG STVPSPVKDIGISTKANSLLISWSHGSG NVERYRLMLMDKGILVHGGVVDKHATSY AFHGLTPGYLYNLTVMTEAAGLQNYRWK LVRTAPMEVSNLKVTNDGSLTSLKVKWQ RPPGNVDSYNITLSHKGTIKESRVLAPW ITETHFKELVPGRLYQVTVSCVSGELSA |

TABLE 15-continued

| SEQ ID NO: | Name | Sequence |
|---|---|---|
| | | QKMAVGRTFPLAVLQLRVKHANETSLSI MWQTPVAEWEKYIISLADRDLLLIHKSL SKDAKEFTFTDLVPGRKYMATVTSISGD LKNSSSVKGRTVPAQVTDLHVANQGMTS SLFTNWTQAQGDVEFYQVLLIHENVVIK NESISSETSRYSFHSLKSGSLYSVVVTT VSGGISSRQVVVEGRTVPSSVSGVTVNN SGRNDYLSVSWLLAPGDVDNYEVTLSHD GKVVQSLVIAKSVRECSFSSLTPGRLYT VTITTRSGKYENHSFSQERTVPDKVQGV SVSNSARSDYLRVSWVHATGDFDHYEVT IKNKNNFIQTKSIPKSENECVFVQLVPG RLYSVTVTTKSGQYEANEQGNGRTIPEK GNSADIQHSGGRSSLEGPRFERTGGGHH HHHH |
| 39 | Wild-type protein sequence of Human VE-PTP (HPTP-β) | MLSHGAGLALWITLSLLQTGLAEPERCN FTLAESKASSHSVSIQWRILGSPCNFSL IYSSDTLGAALCPTFRIDNTTYGCNLQD LQAGTIYNFRIISLDEERTVVLQTDPLP PARFGVSKEKTTSTSLHVWWTPSSGKVT SYEVQLFDENNQKIQGVQIQESTSWNEY TFFNLTAGSKYNIAITAVSGGKRSFSVY TNGSTVPSPVKDIGISTKANSLLISWSH GSGNVERYRLMLDKGILVHGGVVDKHA TSYAFHGLTPGYLNLTVMTEAAGLQNY RWKLVRTAPMEVSNLKVTNDGSLTSLKV KWQRPPGNVDSYNITLSHKGTIKESRVL APWITETHFKELVPGRLYQVTVSCVSGE LSAQKMAVGRTFPDKVANLEANNNGRMR SLVVSWSPPAGDWEQYRILLFNDSVVLL NITVGKEETQYVMDDTGLVPGRQYEVEV IVESGNLKNSERCQGRTVPLAVLQLRVK HANETSLSIMWQTPVAEWEKYIISLADR DLLLIHKSLSKDAKEFTFTDLVPGRKYM ATVTSISGDLKNSSSVKGRTVPAQVTDL HVANQGMTSSLFTNWTQAQGDVEFYQVL LIHENVVIKNESISSETSRYSFHSLKSG SLYSVVVTTVSGGISSRQVVEGRTVPS SVSGVTVNNSGRNDYLSVSWLLAPGDVD NYEVTLSHDGKVVQSLVIAKSVRECSFS SLTPGRLYTVTITTRSGKYENHSFSQER TVPDKVQGVSVSNSARSDYLRVSWVHAT GDFDHYEVTIKNKNNFIQTKSIPKSENE CVFVQLVPGRLYSVTVTTKSGQYEANEQ GNGRTIPEPVKDLTLRNRSTEDLHVTWS GANGDVDQYEIQLLFNDMKVFPPFHLVN TATEYRFTSLTPGRQYKILVLTISGDVQ QSAFIEGFTVPSAVKNIHISPNGATDSL TVNWTPGGGDVDSYTVSAFRHSQKVDSQ TIPKHVFEHTFHRLEAGEQYQIMIASVS GSLKNQINVVGRTVPASVQGVIADNAYS SYSLIVSWQKAAGVAERYDILLLTENGI LLRNTSEPATTKQHKFEDLTPGKKYKIQ ILTVSGGLFSKEAQTEGRTVPAAVTDLR ITENSTRHLSFRWTASEGELSWYNIFLY NPDGNLQERAQVDPLVQSFSFQNLLQGR MYKMVIVTHSGELSNESFIFGRTVPASV SHLRGSNRNTTDSLWFNWSPASGDFDFY ELILYNPNGTKKENWKDKDLTEWRFQGL VPGRKYVLWVVTHSGDLSNKVTAESRTA PSPPSLMSFADIANTSLAITWKGPPDWT DYNDFELQWLPRDALTVFNPYNNRKSEG RIVYGLRPGRSYQFNVKTVSGDSWKTYS KPIFGSVRTKPDKIQNLHCRPQNSTAIA CSWIPPDSDFDGYSIECRKMDTQEVEFS RKLEKEKSLLNIMMLVPHKRYLVSIKVQ SAGMTSEVVEDSTITMIDRPPPPPPHIR VNEKDVLISKSSINFTVNCSWFSDTNGA VKYFTVVREADGSDELKPEQQHPLPSY LEYRHNASIRVYQTNYFASKCAENPNSN SKSFNIKLGAEMESLGGKCDPTQQKFCD GPLKPHTAYRISIRAFTQLFDEDLKEFT KPLYSDTFFSLPITTESEPLFGAIEGVS AGLFLIGMLVAVVALLICRQKVSHGRER PSARLSIRRDRPLSVHLNLGQKGNRKTS CPIKINQFEGHFMKLQADSNYLLSKEYE ELKDVGRNQSCDIALLPENRGKNRYNNI LPYDATRVKLSNVDDDPCSDYINASYIP GNNFRREYIVTQGPLPGTKDDFWKMVWE QNVHNIVMVTQCVEKGRVKCDHYWPADQ DSLYYGDLILQMLSESVLPEWTIREFKI CGEEQLDAHRLIRHFHYTVWPDHGVPET TQSLIQFVRTVRDYINRSPGAGPTVVHC SAGVGRTGTFIALDRILQQLDSKDSVDI YGAVHDLRLHRVHMVQTECQYVYLHQCV RDVLRARKLRSEQENPLFPIYENVNPEY HRDPVYSRH |
| 40 | DNA sequence of Human ½ VE-PTP ECD containing first eight FN3 repeats (SEQ ID NO: 38) | ATGGAATGGAGCTGGGTCTTTCTCTTCT TCCTGTCAGTAACGACTGGTGTCCACTC CGAGCCCGAGAGATGCAACTTCACCCTG GCCAGTCCAAGGCCTCCTCCCACTCCG TGTCTATCCAGTGGCGGATCCTGGGCTC CCCCTGCAACTTCTCTCTGATCTACTCC TCCGACACCCTGGGCGCTGCCCTGTGCC CTACCTTCAGAATCGACAACACCACCTA CGGCTGCAACCTGCAGGATCTGCAGGCC GGCACCATCTACAACTTCAGGATCATCT CCCTGGACGAGGAACGGACCGTGGTGCT GCAGACCGATCCTCTGCCTCCTGCCAGA TTCGGCGTGTCCAAAGAAAAGACCACCT CCACCGGACTGCACGTGTGGTGGACCCC TTCCAGCGGCAAAGTGACCTCCTACGAG GTGCAGCTGTTCGACGAGAACAACCAGA AAATCCAGGGCGTGCAGATCCAGGAATC CACCTCCTGGAACGAGTACACCTTCTTC AACCTGACCGCCGGCTCCAAGTACAATA TCGCCATCACCGCCGTGTCCGGCGGCAA GAGATCCTTCTCCGTGTACACCAACGGC TCCACCGTGCCCAGCCCCGTGAAGGACA TCGGCATCTCCACC AAGGCCAACTCCCTGCTGATCTCCTGGT CCCACGGCTCCGGCAACGTGGAACGGTA CAGACTGATGCTGATGGACAAGGGCATC CTGGTGCACGGCGGCGTGGTGGATAAGC ACGCCACCTCTTACGCCTTCCACGGCCT GACCCCTGGCTACCTGTACAATCTGACC GTGATGACCGAGGCCGCTGGACTGCAGA ACTACCGGTGGAAGCTCGTGCGGACCGC CCCCATGGAAGTGTCCAACCTGAAAGTG ACCAACGACGGCTCCCTGACCTCTCTGA AAGTGAAGTGGCAGAGGCCCCCTGGCAA TGTGGACTCCTACAACATCACCCTGTCC CACAAGGGCACCATCAAAGAATCCCGGG TGCTGGCCCCTTGGATCACCGAGACACA CTTCAAGGAACTGGTGCCTGGCCGGCTG TACCAAGTGACCGTGTCCTGTGTGTCTG GCGAGCTGTCCGCCCAGAAAATGGCCGT GGGCAGAACCTTCCCTCTGGCCGTGCTG CAGCTGAGAGTGAAGCACGCTAACGAGA CATCCCTGTCCATCATGTGGCAGACCCC CGTGGCCGAGTGGGAGAAGTACATCATC AGCCTGGCCGACCGGGACCTGCTGCTGA TCCACAAGTCCCTGAGCAAGGACGCCAA AGAGTTCACCTTCACCGACCTGGTGCCC GGCAGAAAGTACATGGCCACCGTGACCT CCATCTCCGGCGACCTGAAGAACTCCTC CAGCGTGAAGGGCAGGACCGTGCCTGCC CAAGTGACAGACCTGCACGTGGCCAACC AGGGCATGACCTCCTCCCTGTTCACCAA CTGGACCCAGGCTCAGGGCGACGTGGAA TTCTACCAGGTGCTGCTGATTCATGAGA ACGTCGTGATCAAGAACGAGTCCATCTC CTCCGAGACAAGCCGGTACTCCTTCCAC TCCCTGAAGTCCGGCAGCCTGTACTCCG TGGTCGTGACCACAGTGTCCGGGGGCAT CTCCTCTAGACAGGTGGTGGAAGGCA GCACCGTGCCTAGTTCAGTGTCAGGCGT GACCGTGAACAACAGCGGCCGGAACGA CTACCTGTCCGTGTCTTGGCTGCTGGCT CCTGGGGACGTGGACAACTACGAAGTGA |

TABLE 15-continued

| SEQ ID NO: | Name | Sequence |
|---|---|---|
| | | CCCTGAGCCACGACGGCAAGGTGGTGCA GTCTCTCGTGATCGCCAAGTCCGTGCGC GAGTGCTCCTTCAGCTCTCTGACACCTG GCAGACTGTATACCGTGACCATCACCAC CAGATCCGGGAAGTACGAGAACCACAGC TTCTCCCAGGAACGCACAGTGCCCGACA AGGTGCAGGGCGTGTCAGTGTCTAACTC CGCCAGATCTGACTACCTGCGGGTGTCC TGGGTGCACGCTACCGGCGACTTCGACC ATTATGAAGTGACAATCAAGAACAAGAA CAACTTCATCCAGACCAAGTCCATCCCC AAGTCCGAGAACGAGTGCGTGTTCGTGC AGCTGGTGCCAGGCAGACTGTACTCTGT GACAGTGACCACCAAGTCCGGCCAGTAC GAGGCCAACGAGCAGGGCAACGGCAGGA CCATCCCTGAGAAGGGCAACTCCGCCGA CATCCAGCACTCTGGCCGCAGATCCTCT CTGGAAGGCCCCAGATTCGAGAGAACCG GCGGAGGCCACCACCATCATCACCATTG A |
| 41 | Protein sequence of *Cynomolgus* VE-PTP (Cyno PTP-β) containing first eight FN3 repeats with C-terminal His₁₀ tag (SEQ ID NO: 53) (Cyno Beta ½ VE-PTP ECD) | MEWSWVFLFFLSVTTGVHSERCNFTLAE SKASSHSVSIRWRIWGSPCNFNLTYSSD TLGAASCPPFRLDNTTYGCNLQDLQAGT IYNFRIVSLDGEERTVVLQTDPLPPARF GVSKEKTTSTSLHVVWTPSPGKVTSYEV QLFDENNQKIQGVQIQESTSWNKYTFFN LTAGSKYNITITAVSGGKRSSSVYTNGS TVPSPVKDIGISTKANSLLVSWSHGSGN VERYRLMLMDKGILVHGSVVDRQATSYT FNGLTPGYLYNLTVVTEAAGLQNYKWKL VRTAPMEVSNLKVTNDGSLTSLKVKWQR PPGNVDSYNITLSHKGTIKESRVLAPRV TETHFKELTPGRLYQVTVSCVSGELSAQ RMAVGRTFPLPVLQLRVKHANETSLSII WQPPVAEWEEYIISLADRDLRLIHKSLS KDAKEFTFTDLVPGRKYMATVTSISGDL KNSSSVKGRTVPAQVTDLHVANQGMTSS LFTNWTQAQGDVEFYQVLLIHENVVIKN ESIPSETSGYNFHFLKSGSLYSVVVTTV SGGISSRQVVEGRTVPSSVSGVTVNNS GRNDYLSVSWLPAPGDVDNYEVTLSHDG RVVQSLVIAKSVRECSFSSLTPGRLYTV TITTTRSGKYENHSFSQERTVPDKVQGVS VSNSARSDYLRVSWVHATGDFDHYEVTI KNKNNFIETKSIPKSENECVFVQLVPGR LYSVTVTTKSGQYEASEQGNGRTGGGHH HHHHHHHH |
| 42 | DNA sequence of Cyno Beta ½ VE-PTP ECD containing first eight FN3 repeats (SEQ ID NO: 41) | ATGGAATGGAGCTGGGTCTTTCTCTTCT TCCTGTCAGTAACGACTGGTGTCCACTC CGAGCGGTGCAACTTTACCCTGGCCGAG TCCAAGGCCTCCTCCCACTCCGTGTCTA TCCGGTGGCGGATCTGGGGCTCCCCCTG CAACTTCAACCTGACCTACTCCTCCGAT ACCCTGGGCGCTGCCTCCTGTCCTCCTT TCCGGCTGGACAACACCACCTACGGCTG CAACCTGCAGGATCTGCAGGCCGGCACC ATCTACAACTTCCGGATCGTGTCCCTGG ACGGCGAGGAACGGACAGTGGTGCTGCA GACCGATCCTCTGCCCCCTGCCAGATTC GGCGTGTCCAAAGAAAAGACCACCTCCA CCTCCCTGCACGTGTGGTGGACCCCTAG CCCTGGCAAAGTGACCTCCTACGAGGTG CAGCTGTTCGACGAGAACAACCAGAAAA TCCAGGGCGTGCAGATCCAGGAATCCAC CTCCTGGAACAAGTACACCTTCTTCAAT CTGACCGCCGGCTCCAAGTACAACATCA CCATCACCGCCGTGTCCGGCGGCAAGAG ATCCTCCTCCGTGTACACCAACGGCTCC ACCGTGCCCAGCCCCGTGAAGGACATCG GCATCTCCACCAAGGCCAACTCCCTGCT GGTGTCCTGGTCCCACGGCTCCGGCAAC GTGGAACGGTACAGACTGATGCTGATGG ACAAGGGCATCCTGGTGCACGGCAGCGT GGTGGATAGACAGGCCACCTCCTACACC TTCAACGGCCTGACCCCCGGCTACCTGT ATAACCTGACCGTCGTGACCGAGGCCGC TGGACTGCAGAACTACAAGTGGAAGCTC GTGCGGACCGCCCCCATGGAAGTGTCCA ACCTGAAAGTGACCAACGACGGCTCCCT GACCTCTCTGAAAGTGAAGTGGCAGAGG CCCCCTGGCAATGTGGACAGCTACAATA TCACCCTGTCCCACAAGGGCACCATCAA AGAATCCCGGGTGCTGGCCCCCAGAGTG ACCGAGACACACTTCAAAGAGCTGACCC CTGGCCGGCTGTACCAAGTGACCGTGTC CTGTGTGTCTGGCGAGCTGTCTGCCCAG AGAATGGCCGTGGGCAGAACCTTCCCTC TGCCCGTGCTGCAGCTGAGAGTGAAGCA CGCCAACGAGACATCCCTGTCCATCATC TGGCAGCCCCTGTGGCCGAGTGGGAAG AGTACATCATCAGCCTGGCCGACCGGGA CCTGCGGCTGATCCACAAGTCCCTGAGC AAGGACGCCAAAGAGTTCACCTTCACCG ACCTGGTGCCTGGCCGGAAGTACATGGC CACCGTGACCTCCATCTCCGGCGACCTG AAGAACTCCTCCAGCGTGAAGGGCAGGA CCGTGCCTGCCCAAGTGACAGACCTGCA TGTGGCCAACCAGGGCATGACCTCCAGC CTGTTCACCAACTGGACCCAGGCTCAGG GCGACGTGGAATTCTACCAGGTGCTGCT GATCCATGAGAACGTCGTGATCAAGAAC GAGTCCATCCCCTCCGAGACAAGCGGCT ACAACTTTCACTTCCTGAAGTCCGGCAG CCTGTACTCCGTGGTCGTGACCACAGTG TCCGGGGGCATCTCCTCTAGAAGGTGG GGTGGAAGGCCGCACCGTGCCTAGTTCA GTGTCAGGCGTGACCGTGAACAACAGCG GCCGGAACGACTACCTGTCCGTGTCTTG GCTGCCTGCCCCTGGGGACGTGGACAAC TACGAAGTGACCCTGTCTCACGACGGCC GGGTGGTGCAGTCTCGTGATCGCTAA GTCCGTGCGCGAGTGCTCCTTCAGCAGC CTGACACCTGGCAGACTGTATACCGTGA CCATCACCACCAGATCCGGGAAGTACGA GAACCACAGCTTCTCCCAGGAACGAACC GTGCCCGACAAGGTGCAGGGCGTGTCAG TGTCTAACTCCGCCAGATCTGACTACCT GAGAGTGTCCTGGGTGCACGCCACCGGC GACTTCGACCATTATGAAGTGACAATCA AGAACAAGAACAACTTCATCGAGACAAA GAGCATCCCCAAGTCCGAGAACGAGTGC GTGTTCGTGCAGCTGGTGCCAGGCAGGC TGTATTCTGTGACAGTGACCACCAAGTC CGGCCAGTACGAGGCCTCTGAGCAGGGC AATGGCAGAACCGGCGGTGGACACCACC ATCATCACCATCACCACCATCACTAG |
| 43 | Protein sequence of Human HPTP-η with C-terminal His₁₀ tag (SEQ ID NO: 53) (Human HPTP-η ECD) | MEWSWVFLFFLSVTTGVHSAGGTPSPIP DPSVATVATGENGITQISSTAESFHKQN GTGTPQVETNTSEDGESSGANDSLRTPE QGSNGTDGASQKTPSSTGPSPVFDIKAV SISPTNVILTWKSNDTAASEYKYVVKHK MENEKTIVVHQPWCNITGLRPATSYVF SITPGIGNETWGDPRVIKVITEPIPVSD LRVALTGVRKAALSWSNGNGTASCRVLL ESIGSHEELTQDSRLQVNISGLKPGVQY NINPYLLQSNKTKGDPLGTEGGLDASNT ERSRAGSPTAPVHDESLVGPVDPSSGQQ SRDTEVLLVGLEPGTRYNATVYSQAANG TEGQPQAIEFRTNAIQVFDVTAVNISAT SLTLIWKVSDNESSSNYTYKIHVAGETD SSNLNVSEPRAVIPGLRSSTFYNITVCP VLGDIEGTPGFLQVHTPPVPVSDFRVTV VSTTEIGLAWSSHDAESFQMHITQEGAG NSRVEITTNQSIIIGGLFPGTKYCFEIV PKGPNGTEGASRTVCNRTVPSAVFDIHV VYVTTTEMWLDWKSPDGASEYVYHLVIE SKHGSNHTSYDKAITLQGLIPGTLYNI TISPEVDHVWGDPNSTAQYTRPSNVSNI DVSTNTTAATLSWQNFDDASPTYSYCLL |

TABLE 15-continued

| SEQ ID NO: | Name | Sequence |
|---|---|---|
| | | IEKAGNSSNATQVVTDIGITDATVTELI PGSSYTVEIFAQVGDGIKSLEPGRKSFC TDPASMASFDCEVVPKEPALVLKWTCPP GANAGFELEVSSGAWNNATHLESCSSEN GTEYRTEVTYLNFSTSYNISITTVSCGK MAAPTRNTCTTGITDPPPPDGSPNITSV SHNSVKVKFSGFEASHGPIKAYAVILTT GEAGHPSADVLKYTYEDFKKGASDTYVT YLIRTEEKGRSQSLSEVLKYEIDVGNES TTLGYYNGKLEPLGSYRACVAGFTNITF HPQNKGLIDGAESYVSFSRYSDAVSLPQ DPGVICGGGHHHHHHHHHH |
| 44 | DNA sequence of Human HPTP-η with C-terminal His₁₀ tag (SEQ ID NO: 43) ("His₁₀" disclosed as SEQ ID NO: 53) | ATGGAATGGAGCTGGGTCTTTCTCTTCT TCCTGTCAGTAACGACTGGTGTCCACTC CGCAGGTGGCACCCCTAGTCCAATTCCT GACCCTTCAGTAGCAACTGTTGCCACAG GGGAAAATGGCATAACGCAGATCAGCAG TACAGCAGAATCCTTTCATAAACAGAAT GGAACTGGAACACCTCAGGTGGAAACAA ACACCAGTGAGGATGGTGAAAGCTCTGG AGCCAACGATAGTTTAAGAACACCTGAA CAAGGATCTAATGGGACTGATGGGGCAT CTCAAAAAACTCCCAGTAGCACTGGGCC CAGTCCTGTGTTTGACATTAAAGCTGTT TCCATCAGTCCAACCAATGTGATCTTAA CTTGGAAAAGTAATGACACAGCTGCTTC TGAGTACAAGTATGTAGTAAAGCATAAG ATGGAAAATGGAAGACAATTACTGTTG TGCATCAACCATGGTGTAACATCACAGG CTTACGTCCAGCGACTTCATATGTATTC TCCATCACTCCAGGAATAGGCAATGAGA CTTGGGGAGATCCCAGAGTCATAAAAGT CATCACAGAGCCGATCCCAGTTTCTGAT CTCCGTGTTGCCCTCACGGGTGTGAGGA AGGCTGCTCTCTCCTGGAGCAATGGCAA TGGCACTGCCTCCTGCCGGGTTCTTCTT GAAAGCATTGGAAGCCATGAGGAGTTGA CTCAAGACTCAAGACTTCAGGTCAATAT CTCGGGCCTGAAGCCAGGGGTTCAATAC AACATCAACCCGTATCTTCTACAATCAA ATAAGACAAAGGGAGACCCCTTGGGCAC AGAAGGTGGCTTGGATGCCAGCAATACA GAGAGAAGCCGGGCAGGGAGCCCCACCG CCCCTGTGCATGATGAGTCCCTCGTGGG ACCTGTGGACCCATCCTCCGGCCAGCAG TCCCGAGACACGGAAGTCCTGCTTGTCG GGTTAGAGCCTGGCACCCGATACAATGC CACCGTTTATTCCCAAGCAGCGAATGGC ACAGAAGGACAGCCCCAGGCCATAGAGT TCAGGACAAATGCTATTCAGGTTTTTGA CGTCACCGCTGTGAACATCAGTGCCACA AGCCTGACCCTGATCTGGAAAGTCAGCG ATAACGAGTCGTCATCTAACTATACCTA CAAGATACATGTGGCGGGGGAGACAGAT TCTTCCAATCTCAACGTCAGTGAGCCTC GCGCTGTCATCCCCGGACTCCGCTCCAG CACCTTCTACAACATCACAGTGTGTCCT GTCCTAGGTGACATCGAGGGCACGCCGG GCTTCCTCCAAGTGCACACCCCCCCTGT TCCAGTTTCTGACTTCCGAGTGACAGTG GTCAGCACGACGGAGATCGGCTTAGCAT GGAGCAGCCATGATGCAGAATCATTTCA GATGCATATCACACAGGAGGGAGCTGGC AATTCTCGGGTAGAAATAACCACCAACC AAAGTATTATCATTGGTGGCTTGTTCCC TGGAACCAAGTATTGCTTTGAAATAGTT CCAAAAGGACCAAATGGGACTGAAGGGG CATCTCGGACAGTTTGCAATAGAACTGT TCCCAGTGCAGTGTTTGACATCCACGTG GTCTACGTCACCACCACGGAGATGTGGC TGGACTGGAAGAGCCCTGACGGTGCTTC CGAGTATGTCTACCATTTAGTCATAGAG TCCAAGCATGGCTCTAACCACACAAGCA CGTATGACAAAGCGATTACTCTCCAGGG CCTGATTCCGGGCACCTTATATAACATC ACCATCTCTCCAGAAGTGGACCACGTCT GGGGGGGACCCCAACTCCACTGCACAGTA CACACGGCCCAGCAATGTGTCCAACATT GATGTAAGTACCAACACCACAGCAGCAA CTTTAAGTTGGCAGAACTTTGATGACGC CTCTCCCACGTACTCCTACTGCCTTCTT ATTGAGAAGGCTGGAAATTCCAGCAACG CAACACAAGTAGTCACGGACATTGGAAT TACTGACGCTACAGTCACTGAATTAATA CCTGGCTCATCATACACAGTGGAGATCT TTGCACAAGTAGGGGATGGGATCAAGTC ACTGGAACCTGGCCGGAAGTCATTCTGT ACAGATCCTGCGTCCATGGCCTCCTTCG ACTGCGAAGTGGTCCCCAAAGAGCCAGC CCTGGTTCTCAAATGGACCTGCCCTCCT GGCGCCAATGCAGGCTTTGAGCTGGAGG TCAGCAGTGGAGCCTGGAACAATGCGAC CCACCTGGAGAGCTGCTCCTCTGAGAAT GGCACTGAGTATAGAACGGAAGTCACGT ATTTGAATTTTTCTACCTCGTACAACAT CAGCATCACCACTGTGTCCTGTGGAAAG ATGGCAGCCCCCACCCGGAACACCTGCA CTACTGGCATCACAGATCCCCTCCTCC AAGATGGATCCCCTATATTACATCTGTC AGTCACAATTCAGTAAAGGTCAAGTTCA GTGGATTTGAAGCCAGCCACGGACCCAT CAAAGCCTATGCTGTCATTCTCACCACC GGGGAAGCTGGTCACCCTTCTGCAGATG TCCTGAAATACACGTATGAGGATTTCAA AAAGGGAGCCTCAGATACTTATGTGACA TACCTCATAAGAACAGAAGAAAAGGGAC GTTCTCAGAGCTTGTCTGAAGTTTTGAA ATATGAAATTGACGTTGGGAATGAGTCA ACCACACTTGGTTATTACAATGGGAAGC TGGAACCTCTGGGCTCCTACCGGGCTTG TGTGGCTGGCTTCACCAACATTACCTTC CACCCTCAAAACAAGGGGCTCATTGATG GGGCTGAGAGCTATGTGTCCTTCAGTCG CTACTCAGATGCTGTTTCCTTGCCCCAG GATCCAGGTGTCATCTGTGGCGGTGGAC ACCACCATCATCACCATCACCACCATCA CTAG |

HPTP-β, cyno PTP-β, and HPTP-η proteins were coated onto ELISA plates in coating buffer (pH 9.4). Each protein was prepared as a 1 μg/mL protein stock in 50 mM carbonate-bicarbonate. The coated proteins were aliquoted at a volume of 100 μL/well into sterile, clear, polystyrene, flat bottom 96-well plates. The plates were incubated overnight at 4° C. After overnight incubation, the plates were washed 3× with 200 μL/well of 1× PBS-T (PBS with 0.05% Tween 20). The immunizing protein was human VE-PTP (HPP-β). The plates were then blocked with 200 μL/well of 5% blotting grade blocker non-fat dry milk in PBS-T and incubated for 1 hr at room temperature.

Primary antibody samples were prepared for the humanized variants and the negative control, anti-hCD20-hIgG4S228P, using 1 pg/well in 5% blotting grade blocker non-fat dry milk in PBS. Samples were tested in triplicates. The Fab antibody fragments were treated as the IgG antibodies. The plates were then washed 3× with PBS-T and 100 μL of primary antibody preparation was added in each well. The plates were then incubated for 1 hr at room temperature.

Secondary antibody samples were prepared by diluting peroxidase-conjugated affinity purified donkey anti-human IgG specific secondary antibody at 1:2,000 dilution in blotting grade blocker non-fat dry milk in PBS. The plates were then washed 3× with PBS-T and 100 μL of the secondary antibody preparation was added in each well. The plates were then incubated for 1 hr at room temperature. After incubation, the plates were washed 3× with PBS-T.

Then, 75 μg/1-Step™ Ultra TMB-ELISA was added in each well, and the plate was allowed to develop for 5 min at room temperature. After 5 min, 50 μL of 2 M sulfuric acid was added to each well to stop the reaction. The plates were then analyzed on a plate reader at an absorbance wavelength of 450 nm.

Figure 5:
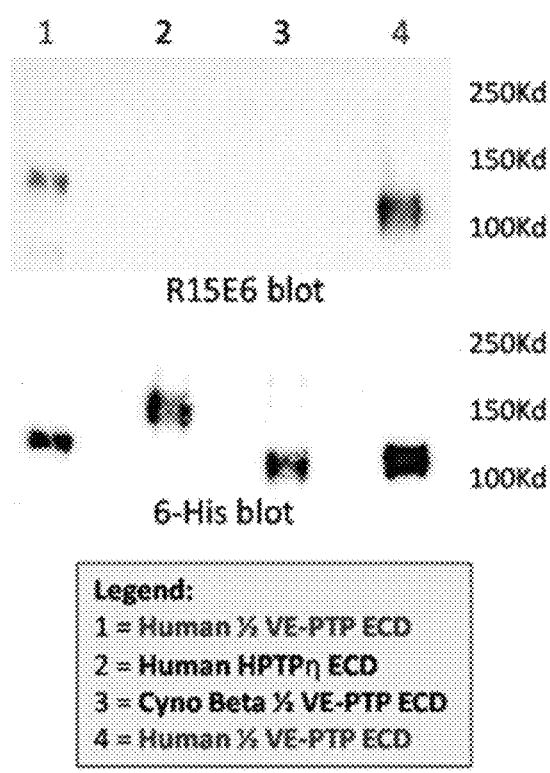
FIG. 5 illustrates the binding specificity of R15E6 to recombinant, 6-His tagged human VE-PTP (HPTP-β) (The "6-His" disclosed in FIG. 5 is SEQ ID NO: 52), cynomolgus PTP-β, and human PTP-η extracellular domain proteins by western blot.

FIG. 5 illustrates western blots of R15E6 screened against species-specific VE-PTP and HPTP-η. R15E6 was highly selective for human VE-PTP (HPTP-β; lanes 1 and 4). No significant binding to human PTP-η or cyno VE-PTP (cyno PTP-β) was observed. The indicated recombinant hexahistidine-tagged proteins (6-His) (SEQ ID NO: 52) were probed sequentially with R15E6 and a commercially-available 6-His antibody ("6-His" is SEQ ID NO: 52). The commercially-available 6-His antibody ("6-His" is SEQ ID NO: 52) exhibited binding to all protein targets, and showed poor selectivity for human VE-PTP (HPP-β).

Figure 17:
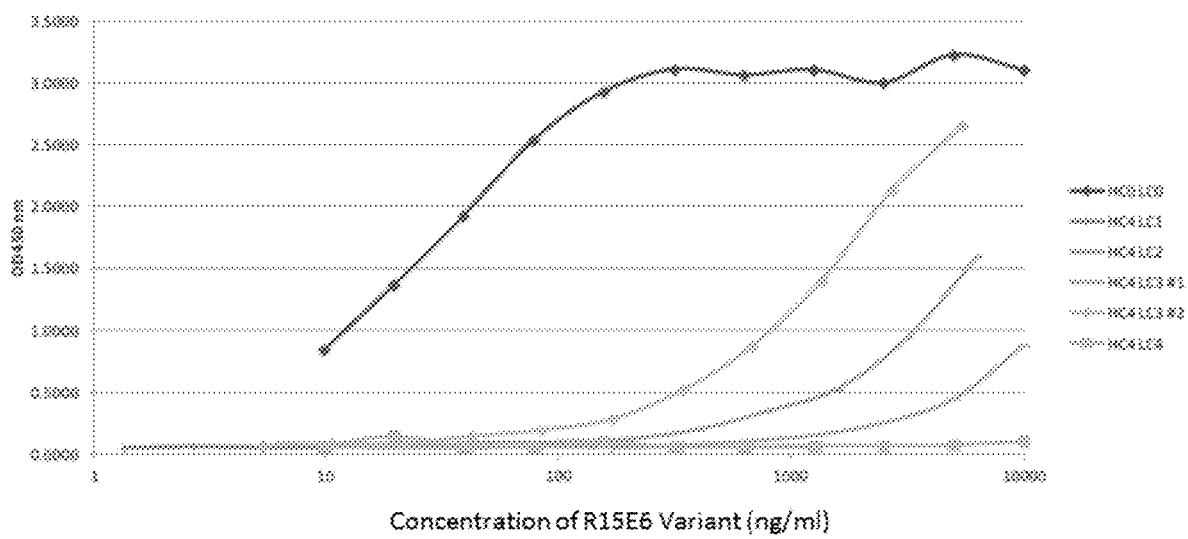
FIG. 17 illustrates binding of HC4 variants of R15E6 and HCOLCO to HPTP-β.

Each humanized variant was measured for affinity to the antigen, human VE-PTP (HPTP-β), using ELISA. 100 mg/well of the VE-PTP (HPP-β) antigen were immobilized onto 96-well Maxisorp plates in coating buffer (0.5 mM NaHCO$_3$ brought to pH 9.6 by the addition of 0.5 mM Na$_2$CO$_3$) overnight at 4° C. The coating buffer was then removed and 200 μL/well of block solution (3% w/v semi-skimmed milk powder, PBS) was added and agitated for 2 hrs at room temperature. The plate was washed four times with PBS-T (1% v/v Tween 20). 100 μL/well was added of purified R15E6 variants serially diluted from 10,000 ng/mL to 9.765 ng/mL in PBS-TB (0.05% v/v Tween 20, 0.5% w/v BSA). Following agitation for 2 hrs at room temperature, the plate was washed 4×with PBS-T. 100 μL/well goat anti-human HRP (Fc specific) at a ratio of 1:60,000 PBS was then added and the plates were incubated for an additional hour with agitation at room temperature. The plate was then washed 6× with PBS-T and once in PBS. Next, 100 μL/well of TMB substrate solution was added and incubated at 37° C. for 10 min. 50 μL 1 M HCl was added per well and the plate immediately read at 450 nm on a Tecan Sunrise plate reader. The ELISA results are shown in FIGS. 14-17. The HC1, HC2 and HC3 variants generally displayed similar binding characteristics compared to the chimeric HCOLCO antibody. The binding of the HC4 variants was much lower than with the other heavy chains variants compared to HCOLCO (FIG. 17).

Samples of each variant were further assessed by Biacore analysis to determine the binding affinity. Antibody binding experiments were performed on Biacore 3000™ at 25° C. Assay buffer: 10 mM HEPES buffer (pH 7.4), 150 mM NaCl, 3 mM EDTA, 0.05% P20 (polyoxyethylenesorbitan). Regeneration buffer: 10 mM glycine HCl (pH 1.75). Conjugation buffer: 10 mM sodium acetate buffer (pH 5). The flow rate used for capturing the ligand was 5 μL/min. The flow rate for the kinetic analysis was 50 μL/min. Flow cell 1 and 2 of the CMS chip were coated with maximum amounts of goat anti-human IgG. Approximately 150 RU of the test antibody was captured on flow cell 2, 3, and 4 as indicated. The antigen was flowed over the chip. Binding of the antigen to the antibodies was monitored in real time. The $K_D$ was determined from the observed $k_{on}$ and $k_{off}$ values.

A scouting analysis was performed using single analyte concentrations as indicated. At these concentrations, binding can be observed even if the ligand binding is weak. Flow cell 1 response was used for reference subtraction.

A full kinetic analysis was performed for the control antibody with a 2-fold serial dilution with the range of concentrations the analyte as indicated: 50, 25, 12.5, 6.25, 3.125, and 0 nM.

TABLE 17 shows the binding kinetic parameters of the binding of each humanized antibody to VE-PTP (HPP-β) ECD, including the association rate ($k_a$), dissociation rate ($k_d$), maximum binding capacity ($R_{max}$), the association constant ($K_A$), and the dissociation constant ($K_D$) as determined by Biacore binding assays. $R_{max}$ was measured as the relative response (RU). All of the humanized candidates exhibited similar binding affinities as the mouse/human chimeric antibody, HC0LC0.

TABLE 17

| Ligand | Analyte | $k_a$ (1/Ms) | $k_d$ (1/s) | $R_{max}$ (RU) | Conc. Of Analyte | $K_A$ (1/M) | $K_D$ (M) |
| --- | --- | --- | --- | --- | --- | --- | --- |
| HC0:LC0 (150RU) | ½ VE-PTP ECD | $2.09 \times 10^5$ $6.71 \times 10^4$ | $6.56 \times 10^{-4}$ $4.17 \times 10^{-4}$ | 27.2 69.6 | 50-0 nM 100 nM | $3.18 \times 10^8$ $1.61 \times 10^8$ | $3.14 \times 10^{-9}$ $6.22 \times 10^{-9}$ |
| HC2:LC4 (145RU) | ½ VE-PTP ECD | $9.86 \times 10^5$ $5.15 \times 10^4$ | $4.29 \times 10^{-4}$ $6.68 \times 10^{-4}$ | 13.9 67.3 | 50-0 nM 100 nM | $2.30 \times 10^9$ $7.72 \times 10^7$ | $4.36 \times 10^{-10}$ $1.30 \times 10^{-8}$ |
| HC2:LC1 (140RU) | ½ VE-PTP ECD | $1.08 \times 10^6$ $4.98 \times 10^4$ | $7.23 \times 10^{-5}$ $6.88 \times 10^{-4}$ | 8.38 54.2 | 50-0 nM 100 nM | $1.5 \times 10^{10}$ $7.24 \times 10^7$ | $6.68 \times 10^{-11}$ $1.38 \times 10^{-8}$ |
| HC1:LC2 (150RU) | ½ VE-PTP ECD | $4.10 \times 10^5$ $2.51 \times 10^5$ | $9.47 \times 10^{-4}$ $7.69 \times 10^{-4}$ | 29.6 52.4 | 50-0 nM 100 nM | $4.33 \times 10^8$ $3.27 \times 10^8$ | $2.31 \times 10^{-9}$ $3.06 \times 10^{-9}$ |
| HC2:LC3 (145RU) | ½ VE-PTP ECD | $8.90 \times 10^5$ $2.22 \times 10^5$ | $1.23 \times 10^{-3}$ $6.62 \times 10^{-4}$ | 22.6 38.8 | 25-0 nM 100 nM | $6.75 \times 10^8$ $3.36 \times 10^8$ | $1.48 \times 10^{-9}$ $2.98 \times 10^{-9}$ |
| HC3:LC2 (140RU) | ½ VE-PTP ECD | $5.39 \times 10^4$ $2.05 \times 10^5$ | $1.23 \times 10^{-3}$ $9.93 \times 10^{-4}$ | 104 36.8 | 25-0 nM 100 nM | $4.30 \times 10^7$ $2.06 \times 10^8$ | $2.32 \times 10^{-8}$ $4.84 \times 10^{-9}$ |
| HC1:LC4 (150RU) | ½ VE-PTP ECD | $5.96 \times 10^5$ $1.79 \times 10^5$ | $1.34 \times 10^{-3}$ $7.92 \times 10^{-4}$ | 24.6 49 | 50-0 nM 100 nM | $4.44 \times 10^8$ $2.26 \times 10^8$ | $2.25 \times 10^{-9}$ $4.42 \times 10^{-9}$ |
| HC2:LC2 (145RU) | ½ VE-PTP ECD | $4.25 \times 10^4$ $1.49 \times 10^5$ | $2.15 \times 10^{-3}$ $5.24 \times 10^{-4}$ | 313 40.8 | 25-0 nM 100 nM | $1.98 \times 10^7$ $2.85 \times 10^8$ | $5.06 \times 10^{-8}$ $3.51 \times 10^{-9}$ |
| HC3:LC4 (140RU) | ½ VE-PTP ECD | $1.34 \times 10^5$ $1.39 \times 10^5$ | $1.09 \times 10^{-3}$ $8.87 \times 10^{-4}$ | 42.8 44.7 | 25-0 nM 100 nM | $1.23 \times 10^8$ $1.59 \times 10^8$ | $8.14 \times 10^{-9}$ $6.29 \times 10^{-9}$ |

TABLE 18 shows the binding selectivity of the humanized antibodies compared to the parental antibody (R15E6) and the inactive control (IgG4) as determined by ELISA. A value that is less than or equal to 0.2 signifies no binding. The humanized antibody candidates, the parental R15E6, and the mouse/human chimeric antibody (HC0:LC0) all exhibited high selectivity for human VE-PTP (HPP-β) as indicated by no significant binding to human PTP-η and cyno PTP-β.

TABLE 18

| Clone (1 µg/well) | Human VE-PTP | Human PTPη | Cyno VE-PTP |
|---|---|---|---|
| HC0:LC0 | 1.8 | 0.16 | 0.12 |
| HC1:LC2 | 1.75 | 0.12 | 0.13 |
| HC1:LC4 | 1.74 | 0.12 | 0.19 |
| HC2:LC1 | 1.81 | 0.13 | 0.18 |
| HC2:LC2 | 1.92 | 0.12 | 0.12 |
| HC2:LC3 | 1.55 | 0.12 | 0.13 |
| HC2:LC4 | 1.65 | 0.11 | 0.13 |
| HC3:LC4 | 2.00 | 0.11 | 0.14 |
| Parental | 2.43 | 0.14 | 0.17 |
| IgG4 | 0.20 | 0.13 | 0.16 |

Figure 18:
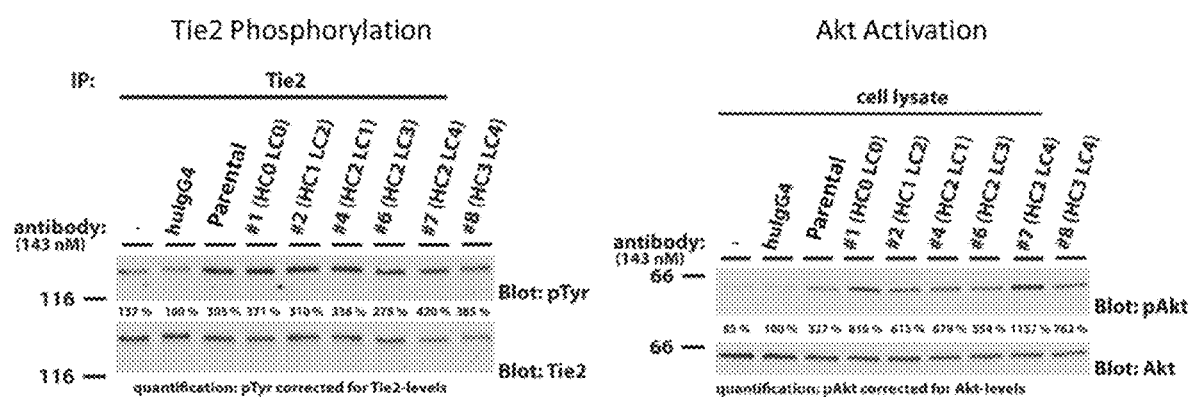
FIG. 18 illustrates Tie2 phosphorylation (left panel) and Akt activation (right panel) in the absence of Ang1 by the various humanized antibodies as determined by western blot.

The humanized antibodies used for targeting human VE-PTP (HPP-β) can restore Tie2 activity by autophosphorylation and initiate downstream effectors including, for example, proteins in the PI3K—Akt pathway. In addition to assessing binding of the antibodies to human VE-PTP (HPP-β), the ability of the antibodies to activate these effector proteins was measured. FIG. 18 illustrates the activation of Tie2 (left panel) and Akt (right panel) in the absence of Tie2 ligands (e.g., Ang1 or Ang2) by the humanized variants as determined by western blot. The activities of the humanized variants were similar to that of the parental murine antibody R15E6 and the chimeric antibody HC0LC0. Human IgG4 was used as a control. All antibodies were tested at 50 nM. The top panel of each blot shows phosphorylation of either Tie2 or Akt, indicating Tie2 or Akt activation. Tie2 and Akt exhibited greater phosphorylation in samples treated with the humanized antibodies than those samples treated with the control antibodies, and indicated that the humanized antibodies were effective in activating Tie2 and Akt even in the absence of ligands.

FIG. 19 illustrates concentration-dependent activation of Tie2 (top panel) and Akt (bottom panel) in the absence of Tie2 ligands (e.g., Ang1 or Ang2) by humanized antibodies, HC2LC4 and HC1LC1 as determined by western blot. Tie2 and Akt signaling activity was observed at low nanomolar concentrations of the humanized variants. The upper panel of each blot shows phosphorylation of either Tie2 or Akt, indicating Tie2 or Akt activation. Tie2 and Akt exhibited greater phosphorylation in the samples treated with the humanized antibodies than exhibited in samples treated with the control antibodies. This result indicates that the humanized antibodies were effective in activating Tie2 and Akt even in the absence of Ang1.

Figure 20:
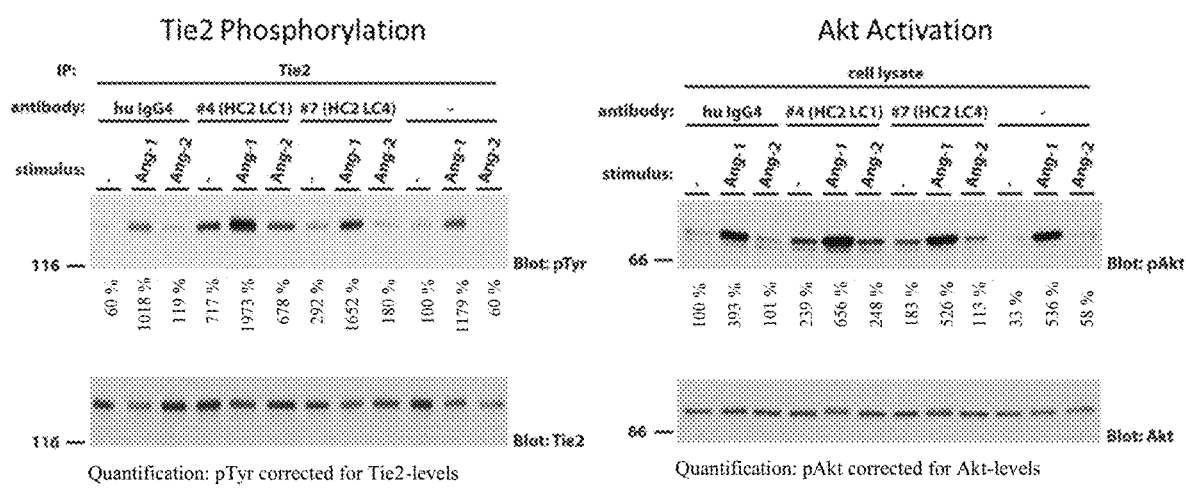
FIG. 20 illustrates Tie2 phosphorylation (left panel) and Akt activation (right panel) in the presence of Ang1 and Ang2 by HC2LC4 and HC2LC1 as determined by western blot.

FIG. 20 illustrates the activation of Tie2 (left panel) and Akt (right panel) in the presence of Ang1 and Ang2 by the humanized antibody candidates, HC2LC4 and HC1LC1, as determined by western blot. HC2LC4 and HC1LC1 activated both Tie2 and Akt in the presence of Ang2, and enhanced Ang1-mediated Tie2 and Akt activation, as indicated by the increase in Tie2 and Akt phosphorylation, respectively. All antibodies were tested at 10 nM.

Figure 21:
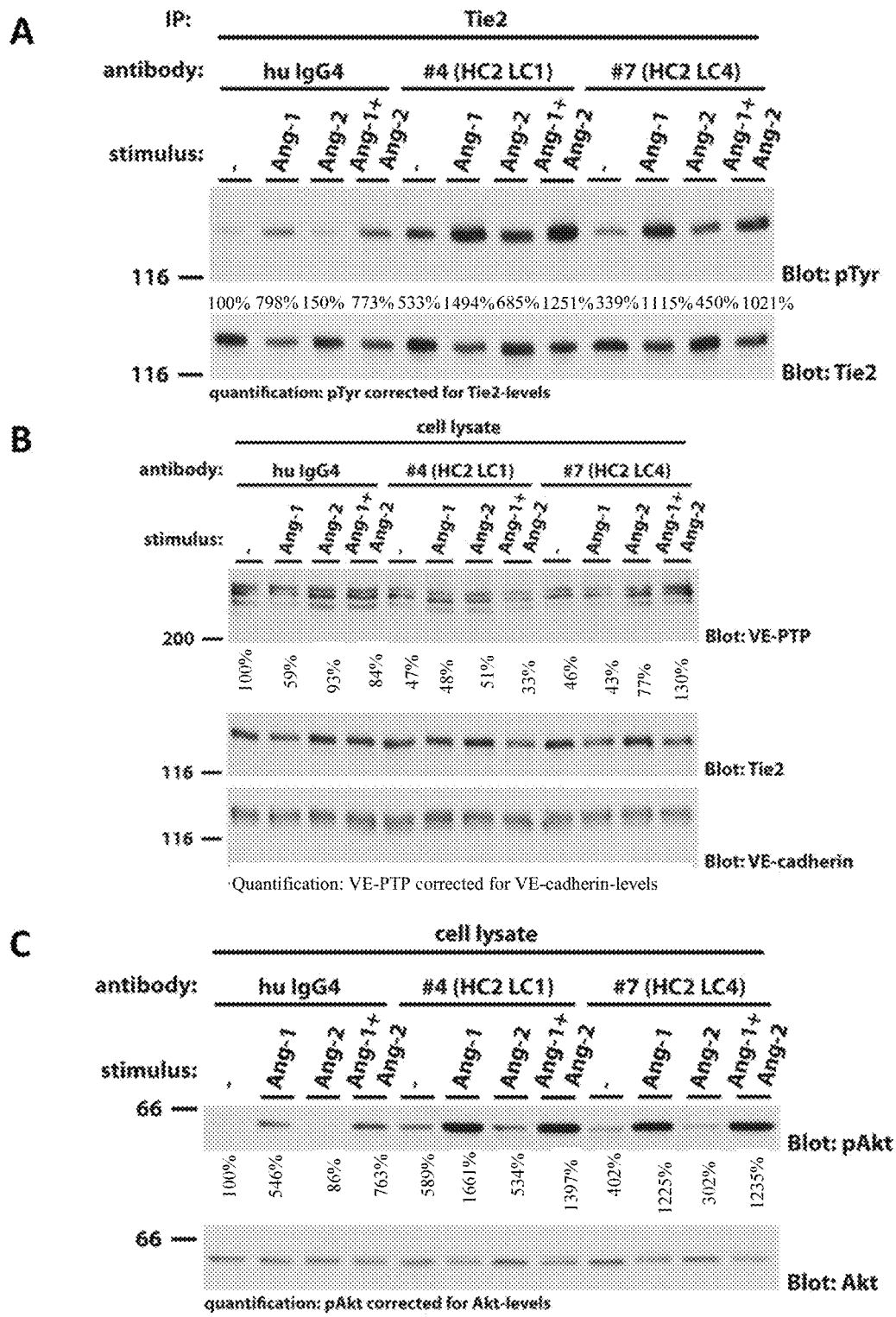
FIG. 21 illustrates Tie2 phosphorylation (panel A), human VE-PTP (HPTP-β) expression (panel B), and Akt activation (panel C) in the presence of Ang1 and/or Ang2 by HC2LC1 and HC2LC4 as determined by western blot.

FIG. 21 illustrates the activation of Tie2 (panel A), human VE-PTP (HPP-β) expression (panel B), and Akt (panel C) in the presence of Ang1 or Ang2 by the humanized antibody candidates, HC2LC1 and HC2LC4, as determined by western blot. HC2LC1 and HC2LC4 activated Tie2 in the presence of Ang1 alone, Ang2 alone, and in the presence of both Ang1 and Ang2. The antibodies were pre-incubated for 15 min and then stimulated by Ang1 or Ang2 for 10 min at a concentration of 600 ng/mL. All antibodies were tested at 10 nM.

Figure 22:
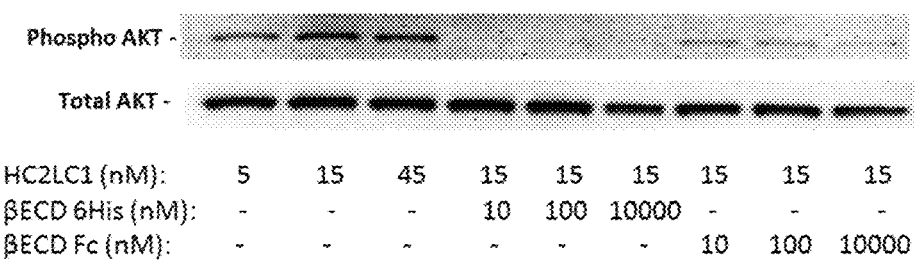
FIG. 22 illustrates Akt activation by HC2LC1 alone and with excess recombinant human VE-PTP extracellular domain protein (βECD 6His (The "6-His" disclosed in FIG. 22 is SEQ ID NO: 52) or βECD Fc) as determined by western blot.

FIG. 22 illustrates the activation of Akt in HUVECs using the humanized antibody candidate, HC2LC1. The upper panel of the first 3 blots shows phosphorylation of Akt, indicating Akt activation, at increasing concentrations of HC2LC1. Consistent with the binding affinity study, HC2LC1 activated Akt at nanomolar concentrations of antibody. Akt activation by HC2LC1 was blocked by pre-incubation of the antibody with the human VE-PTP (HPP-β) extracellular domain (βECD 6His ("6-His" is SEQ ID NO: 52) and βECD Fc). This result indicates that HC2LC1-mediated Akt activation occurs through HC2LC1 binding to the human VE-PTP (HPP-β) extracellular domain.

Figure 23:
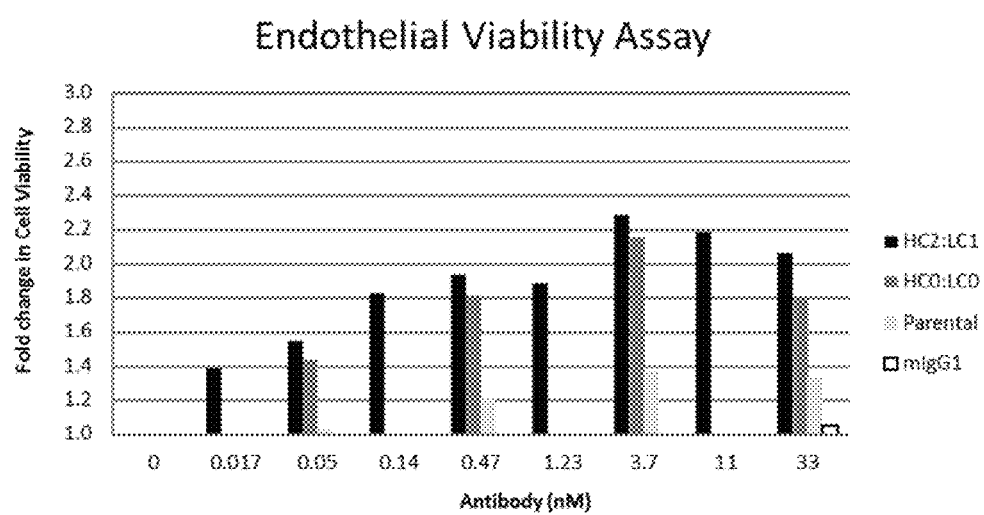
FIG. 23 illustrates enhanced endothelial cell viability by HC2LC1 and HCOLCO as compared to the parenteral antibody (R15E6) and a mouse IgG1 control.

FIG. 23 illustrates the enhanced viability in serum-starved HUVECs using humanized antibody candidates HC2LC1 and HC0LC0, as compared to the parental antibody, R15E6, and the mIgG1 control.

EMBODIMENTS

Embodiment 1. A compound comprising a sequence that is at least 80% identical to SEQ ID NO: 9, SEQ ID NO: 10, SEQ ID NO: 11, or SEQ ID NO: 12.

Embodiment 2. The compound of embodiment 1, wherein the sequence is at least 85% identical to SEQ ID NO: 9, SEQ ID NO: 10, SEQ ID NO: 11, or SEQ ID NO: 12.

Embodiment 3. The compound of any one of embodiments 1-2, wherein the sequence is at least 90% identical to SEQ ID NO: 9, SEQ ID NO: 10, SEQ ID NO: 11, or SEQ ID NO: 12.

Embodiment 4. The compound of any one of embodiments 1-3, wherein the sequence is at least 95% identical to SEQ ID NO: 9, SEQ ID NO: 10, SEQ ID NO: 11, or SEQ ID NO: 12.

Embodiment 5. The compound of embodiment 1, wherein the sequence is at least 80% identical to SEQ ID NO: 9.

Embodiment 6. The compound of any one of embodiments 1-5, wherein the sequence is SEQ ID NO: 9.

Embodiment 7. The compound of embodiment 1, wherein the sequence is at least 80% identical to SEQ ID NO: 10.

Embodiment 8. The compound of any one of embodiments 1-4 and 7, wherein the sequence is SEQ ID NO: 10.

Embodiment 9. The compound of embodiment 1, wherein the sequence is at least 80% identical to SEQ ID NO: 11.

Embodiment 10. The compound of any one of embodiments 1-4 and 9, wherein the sequence is SEQ ID NO: 11.

Embodiment 11. The compound of embodiment 1, wherein the sequence is at least 80% identical to SEQ ID NO: 12.

Embodiment 12. The compound of any one of embodiments 1-4 and 11, wherein the sequence is SEQ ID NO: 12.

Embodiment 13. The compound of embodiment 1, wherein the sequence is at least 80% identical to SEQ ID NO: 29.

Embodiment 14. The compound of embodiment 1, wherein the sequence is SEQ ID NO: 29.

Embodiment 15. The compound of embodiment 1, wherein the sequence is at least 80% identical to SEQ ID NO: 30.

Embodiment 16. The compound of embodiment 1, wherein the sequence is SEQ ID NO: 30.

Embodiment 17. The compound of embodiment 1, wherein the sequence is at least 80% identical to SEQ ID NO: 31.

Embodiment 18. The compound of embodiment 1, wherein the sequence is SEQ ID NO:

Embodiment 19. The compound of embodiment 1, wherein the sequence is at least 80% identical to SEQ ID NO: 32.

Embodiment 20. The compound of embodiment 1, wherein the sequence is SEQ ID NO: 32.

Embodiment 21. The compound of any one of embodiments 1-20, wherein the compound inhibits a tyrosine phosphatase.

Embodiment 22. The compound of any one of embodiments 1-21, wherein the compound inhibits HPTP-β.

Embodiment 23. The compound of any one of embodiments 1-22, wherein the compound inhibits VE-PTP.

Embodiment 24. The compound of any one of embodiments 1-23, wherein the compound activates Tie2.

Embodiment 25. The compound of any one of embodiments 1-24, wherein the compound activates Akt.

Embodiment 26. The compound of any one of embodiments 1-25, wherein the compound binds an extracellular domain of HPTP-β.

Embodiment 27. The compound of any one of embodiments 1-26, wherein the compound binds the first FN3 repeat of an extracellular domain of HPTP-β.

Embodiment 28. The compound of any one of embodiments 1-27, wherein a binding affinity ($K_D$) of the compound to the extracellular domain of HPTP-β is about 70 pM to about 70 nM.

Embodiment 29. A compound comprising a sequence that is at least 80% identical to SEQ ID NO: 20, SEQ ID NO: 21, SEQ ID NO: 22, or SEQ ID NO: 23.

Embodiment 30. The compound of embodiment 29, wherein the sequence is at least 85% identical to SEQ ID NO: 20, SEQ ID NO: 21, SEQ ID NO: 22, or SEQ ID NO: 23.

Embodiment 31. The compound of any one of embodiments 29-30, wherein the sequence is at least 90% identical to SEQ ID NO: 20, SEQ ID NO: 21, SEQ ID NO: 22, or SEQ ID NO: 23.

Embodiment 32. The compound of any one of embodiments 29-31, wherein the sequence is at least 95% identical to SEQ ID NO: 20, SEQ ID NO: 21, SEQ ID NO: 22, or SEQ ID NO: 23.

Embodiment 33. The compound of embodiment 29, wherein the sequence is at least 80% identical to SEQ ID NO: 20.

Embodiment 34. The compound of any one of embodiments 29-33, wherein the sequence is SEQ ID NO: 20.

Embodiment 35. The compound of embodiment 29, wherein the sequence is at least 80% identical to SEQ ID NO: 21.

Embodiment 36. The compound of any one of embodiments 29-32 and 35, wherein the sequence is SEQ ID NO: 21.

Embodiment 37. The compound of embodiment 29, wherein the sequence is at least 80% identical to SEQ ID NO: 22.

Embodiment 38. The compound of any one of embodiments 29-32 and 37, wherein the sequence is SEQ ID NO: 22.

Embodiment 39. The compound of embodiment 29, wherein the sequence is at least 80% identical to SEQ ID NO: 23.

Embodiment 40. The compound of any one of embodiments 29-32 and 39, wherein the sequence is SEQ ID NO: 23.

Embodiment 41. The compound of embodiment 29, wherein the sequence is at least 80% identical to SEQ ID NO: 34.

Embodiment 42. The compound of embodiment 29, wherein the sequence is SEQ ID NO: 34.

Embodiment 43. The compound of embodiment 29, wherein the sequence is at least 80% identical to SEQ ID NO: 35.

Embodiment 44. The compound of embodiment 29, wherein the sequence is SEQ ID NO: 35.

Embodiment 45. The compound of embodiment 29, wherein the sequence is at least 80% identical to SEQ ID NO: 36.

Embodiment 46. The compound of embodiment 29, wherein the sequence is SEQ ID NO: 36.

Embodiment 47. The compound of embodiment 29, wherein the sequence is at least 80% identical to SEQ ID NO: 37.

Embodiment 48. The compound of embodiment 29, wherein the sequence is SEQ ID NO: 37.

Embodiment 49. The compound of any one of embodiments 29-48, wherein the compound inhibits a tyrosine phosphatase.

Embodiment 50. The compound of any one of embodiments 29-49, wherein the compound inhibits HPTP-β.

Embodiment 51. The compound of any one of embodiments 29-50, wherein the compound inhibits VE-PTP.

Embodiment 52. The compound of any one of embodiments 29-51, wherein the compound activates Tie2.

Embodiment 53. The compound of any one of embodiments 29-52, wherein the compound activates Akt.

Embodiment 54. The compound of any one of embodiments 29-53, wherein the compound binds an extracellular domain of HPTP-β.

Embodiment 55. The compound of any one of embodiments 29-54, wherein the compound binds the first FN3 repeat of an extracellular domain of HPTP-β.

Embodiment 56. The compound of any one of embodiments 29-55, wherein a binding affinity ($K_D$) of the compound to the extracellular domain of HPTP-β is about 70 pM to about 70 nM.

Embodiment 57. A compound comprising: a) a heavy chain that comprises a sequence that is at least 80% identical to SEQ ID NO: 30; and b) a light chain that comprises a sequence that is at least 80% identical to SEQ ID NO: 34.

Embodiment 58. The compound of embodiment 57, wherein the heavy chain is at least 85% identical to SEQ ID NO: 30; and the light chain is at least 85% identical to SEQ ID NO: 34.

Embodiment 59. The compound of any one of embodiments 57-58, wherein the heavy chain is at least 90% identical to SEQ ID NO: 30; and the light chain is at least 90% identical to SEQ ID NO: 34.

Embodiment 60. The compound of any one of embodiments 57-59, wherein the heavy chain is at least 95% identical to SEQ ID NO: 30; and the light chain is at least 95% identical to SEQ ID NO: 34.

Embodiment 61. The compound of any one of embodiments 57-60, wherein the heavy chain is SEQ ID NO: 30 and the light chain is SEQ ID NO: 34.

Embodiment 62. The compound of any one of embodiments 57-61, wherein the compound inhibits a tyrosine phosphatase.

Embodiment 63. The compound of any one of embodiments 57-62, wherein the compound inhibits HPTP-β.

Embodiment 64. The compound of any one of embodiments 57-63, wherein the compound inhibits VE-PTP.

Embodiment 65. The compound of any one of embodiments 57-64, wherein the compound activates Tie2.

Embodiment 66. The compound of any one of embodiments 57-65, wherein the compound activates Akt.

Embodiment 67. The compound of any one of embodiments 57-66, wherein the compound binds an extracellular domain of HPTP-β.

Embodiment 68. The compound of any one of embodiments 57-67, wherein the compound binds the first FN3 repeat of an extracellular domain of HPTP-β.

Embodiment 69. The compound of any one of embodiments 57-68, wherein a binding affinity ($K_D$) of the compound to the extracellular domain of HPTP-β is about 70 pM to about 70 nM.

Embodiment 70. A compound comprising: a) a heavy chain that comprises a sequence that is at least 80% identical to SEQ ID NO: 29; and b) a light chain that comprises a sequence that is at least 80% identical to SEQ ID NO: 35.

Embodiment 71. The compound of embodiment 70, wherein the heavy chain is at least 85% identical to SEQ ID NO: 29; and the light chain is at least 85% identical to SEQ ID NO: 35.

Embodiment 72. The compound of any one of embodiments 70-71, wherein the heavy chain is at least 90% identical to SEQ ID NO: 29; and the light chain is at least 90% identical to SEQ ID NO: 35.

Embodiment 73. The compound of any one of embodiments 70-72, wherein the heavy chain is at least 95% identical to SEQ ID NO: 29; and the light chain is at least 95% identical to SEQ ID NO: 35.

Embodiment 74. The compound of any one of embodiments 70-73, wherein the heavy chain is SEQ ID NO: 29 and the light chain is SEQ ID NO: 35.

Embodiment 75. The compound of any one of embodiments 70-74, wherein the compound inhibits a tyrosine phosphatase.

Embodiment 76. The compound of any one of embodiments 70-75, wherein the compound inhibits HPTP-β.

Embodiment 77. The compound of any one of embodiments 70-76, wherein the compound inhibits VE-PTP.

Embodiment 78. The compound of any one of embodiments 70-77, wherein the compound activates Tie2.

Embodiment 79. The compound of any one of embodiments 70-78, wherein the compound activates Akt.

Embodiment 80. The compound of any one of embodiments 70-79, wherein the compound binds an extracellular domain of HPTP-β.

Embodiment 81. The compound of any one of embodiments 70-80, wherein the compound binds the first FN3 repeat of an extracellular domain of HPTP-β.

Embodiment 82. The compound of any one of embodiments 70-81, wherein a binding affinity ($K_D$) of the compound to the extracellular domain of HPTP-β is about 70 pM to about 70 nM.

Embodiment 83. A compound comprising: a) a heavy chain that comprises a sequence that is at least 80% identical to SEQ ID NO: 30; and b) a light chain that comprises a sequence that is at least 80% identical to SEQ ID NO: 37.

Embodiment 84. The compound of embodiment 83, wherein the heavy chain is at least 85% identical to SEQ ID NO: 30; and the light chain is at least 85% identical to SEQ ID NO: 37.

Embodiment 85. The compound of any one of embodiments 83-84, wherein the heavy chain is at least 90% identical to SEQ ID NO: 30; and the light chain is at least 90% identical to SEQ ID NO: 37.

Embodiment 86. The compound of any one of embodiments 83-85, wherein the heavy chain is at least 95% identical to SEQ ID NO: 30; and the light chain is at least 95% identical to SEQ ID NO: 37.

Embodiment 87. The compound of any one of embodiments 83-86, wherein the heavy chain is SEQ ID NO: 30 and the light chain is SEQ ID NO: 37.

Embodiment 88. The compound of any one of embodiments 83-87, wherein the compound inhibits a tyrosine phosphatase.

Embodiment 89. The compound of any one of embodiments 83-88, wherein the compound inhibits HPTP-β.

Embodiment 90. The compound of any one of embodiments 83-89, wherein the compound inhibits VE-PTP.

Embodiment 91. The compound of any one of embodiments 83-90, wherein the compound activates Tie2.

Embodiment 92. The compound of any one of embodiments 83-91, wherein the compound activates Akt.

Embodiment 93. The compound of any one of embodiments 83-92, wherein the compound binds an extracellular domain of HPTP-β.

Embodiment 94. The compound of any one of embodiments 83-93, wherein the compound binds the first FN3 repeat of an extracellular domain of HPTP-β.

Embodiment 95. The compound of any one of embodiments 83-94, wherein a binding affinity ($K_D$) of the compound to the extracellular domain of HPTP-β is about 70 pM to about 70 nM.

Embodiment 96. A method of treating a condition in a subject in need thereof, the method comprising administering to the subject a therapeutically-effective amount of the compound of any one of embodiments 1-95.

Embodiment 97. The method of embodiment 96, wherein the condition is an ocular condition.

Embodiment 98. The method of embodiment 96 or 97, wherein the condition is diabetic retinopathy.

Embodiment 99. The method of any one of embodiments 96-97, wherein the condition is neovascularization.

Embodiment 100. The method of any one of embodiments 96-97, wherein the condition is vascular leak.

Embodiment 101. The method of any one of embodiments 96-97, wherein the condition is increased intraocular pressure.

Embodiment 102. The method of any one of embodiments 96-97, wherein the condition is ocular edema.

Embodiment 103. The method of embodiment 96 or 97, wherein the condition is diabetic macular edema.

Embodiment 104. The method of any one of embodiment 96 or 97, wherein the condition is ocular hypertension.

Embodiment 105. The method of embodiment 96 or 97, wherein the condition is ocular inflammation.

Embodiment 106. The method of any one of embodiments 96-105, wherein the administration is to an eye of the subject.

Embodiment 107. The method of any one of embodiments 96-106, wherein the administration is intravitreal.

Embodiment 108. The method of any one of embodiments 96-105, wherein the administration is subcutaneous.

Embodiment 109. The method of any one of embodiments 96-106, wherein the administration is topical.

Embodiment 110. The method of any one of embodiments 96-109, wherein the subject is a human.

Embodiment 111. The method of any one of embodiments 96-110, wherein the therapeutically-effective amount of the compound is from about 0.25 mg to about 200 mg.

Embodiment 112. The method of any one of embodiments 96-110, wherein the therapeutically-effective amount of the compound is from about 1 mg/kg to about 10 mg/kg.

Embodiment 113. The method of any one of embodiments 96-110, wherein the therapeutically-effective amount of the compound is from about 1 mg to about 50 mg.

Embodiment 114. The method of any one of embodiments 96-110, wherein the therapeutically-effective amount of the compound is from about 50 mg to about 200 mg.

What is claimed is:

1. An antibody comprising:
   a light chain variable domain sequence that is any one of SEQ ID NOs: 20-23,
   wherein the light chain variable domain sequence comprises complementarity-determining region (CDR) sequences that are SEQ ID NO: 57, SEQ ID NO: 58, and SEQ ID NO: 59,
   wherein the light chain variable domain sequence is contained within a light chain sequence that is any one of SEQ ID NOs: 34-37.

2. The antibody of claim 1, wherein the antibody binds human protein tyrosine phosphatase-beta (HPTP-β).

3. The antibody of claim 1, wherein the antibody binds an extracellular domain of HPTP-β.

4. The antibody of claim 1, wherein a binding affinity ($K_D$) of the antibody to the extracellular domain of HPTP-β is about 70 pM to about 70 nM.

5. The antibody of claim 1, wherein the antibody binds a first FN3 repeat of an extracellular domain of HPTP-β.

6. The antibody of claim 1, wherein the antibody inhibits HPTP-β.

7. The antibody of claim 1, wherein the antibody activates tyrosine kinase with immunoglobulin and epidermal growth factor homology domains 2 (Tie-2).

8. The antibody of claim 1, wherein the antibody activates Protein kinase B (Akt).

9. The antibody of claim 1, wherein the antibody is humanized.

10. The antibody of claim 1, wherein the light chain variable domain sequence is SEQ ID NO: 20.

11. The antibody of claim 1, wherein the light chain variable domain sequence is SEQ ID NO: 21.

12. The antibody of claim 1, wherein the light chain variable domain sequence is SEQ ID NO: 22.

13. The antibody of claim 1, wherein the light chain variable domain sequence is SEQ ID NO: 23.

14. The antibody of claim 1, wherein the light chain sequence is SEQ ID NO: 34.

15. The antibody of claim 1, wherein the light chain sequence is SEQ ID NO: 35.

16. The antibody of claim 1, wherein the light chain sequence is SEQ ID NO: 36.

17. The antibody of claim 1, wherein the light chain sequence is SEQ ID NO: 37.

18. A pharmaceutical composition comprising a therapeutically effective amount of an antibody comprising:
   a light chain variable domain sequence that is any one of SEQ ID NOs: 20-23,
   wherein the light chain variable domain sequence comprises complementarity-determining region (CDR) sequences that are SEQ ID NO: 57, SEQ ID NO: 58, and SEQ ID NO: 59,
   wherein the light chain variable domain sequence is contained within a light chain sequence that is any one of SEQ ID NOs: 34-37; and
   a pharmaceutically acceptable carrier.

19. The composition of claim 18, wherein the therapeutically effective amount of the antibody is from about 0.25 mg to about 200 mg.

20. The composition of claim 18, wherein the therapeutically effective amount of the antibody is from about 1 mg/kg to about 10 mg/kg.

21. The composition of claim 18, wherein the therapeutically effective amount of the antibody is from about 1 mg to about 50 mg.

22. The composition of claim 18, wherein the therapeutically effective amount of the antibody is from about 50 mg to about 200 mg.

23. The composition of claim 18, wherein the composition is formulated for intravitreal administration.

24. The composition of claim 18, wherein the composition is formulated for intravenous administration.

25. The composition of claim 18, wherein the composition is formulated for subcutaneous administration.

26. The composition of claim 18, wherein the composition is formulated for topical administration.

27. The composition of claim 18, wherein the light chain variable domain sequence is SEQ ID NO: 20.

28. The composition of claim 18, wherein the light chain variable domain sequence is SEQ ID NO: 21.

29. The composition of claim 18, wherein the light chain variable domain sequence is SEQ ID NO: 22.

30. The composition of claim 18, wherein the light chain variable domain sequence is SEQ ID NO: 23.

31. The composition of claim 18, wherein the light chain sequence is SEQ ID NO: 34.

32. The composition of claim 18, wherein the light chain sequence is SEQ ID NO: 35.

33. The composition of claim 18, wherein the light chain sequence is SEQ ID NO: 36.

34. The composition of claim 18, wherein the light chain sequence is SEQ ID NO: 37.

* * * * *

UNITED STATES PATENT AND TRADEMARK OFFICE
CERTIFICATE OF CORRECTION

| | |
|---|---|
| PATENT NO. | : 11,180,551 B2 |
| APPLICATION NO. | : 16/851420 |
| DATED | : November 23, 2021 |
| INVENTOR(S) | : Peters et al. |

It is certified that error appears in the above-identified patent and that said Letters Patent is hereby corrected as shown below:

On the Title Page

Item (71), please replace: "Cincinnati, OH (US)" with --Watertown, MA (US)--.

Signed and Sealed this
Twenty-fourth Day of May, 2022

*Katherine Kelly Vidal*

Katherine Kelly Vidal
*Director of the United States Patent and Trademark Office*